U.S. Patent No.: US 10,494,363 B2
Date of Patent: Dec. 3, 2019

(12) United States Patent
Johnson et al.

(54) NON-STEROIDAL GLUCOCORTICOID RECEPTOR MODULATORS FOR LOCAL DRUG DELIVERY

(71) Applicant: LEO PHARMA A/S, Ballerup (DK)

(72) Inventors: Patrick Stephen Johnson, Ballerup (DK); Kevin Neil Dack, Ballerup (DK); Krister Henriksson, Ballerup (DK)

(73) Assignee: Leo Pharma A/S, Ballerup (DK)

( * ) Notice: Subject to any disclaimer, the term of this patent is extended or adjusted under 35 U.S.C. 154(b) by 0 days.

(21) Appl. No.: 15/759,622

(22) PCT Filed: Sep. 13, 2016

(86) PCT No.: PCT/EP2016/071580
§ 371 (c)(1),
(2) Date: Mar. 13, 2018

(87) PCT Pub. No.: WO2017/046096
PCT Pub. Date: Mar. 23, 2017

(65) Prior Publication Data
US 2018/0258080 A1    Sep. 13, 2018

(30) Foreign Application Priority Data
Sep. 15, 2015  (EP) .................... 15185283

(51) Int. Cl.
C07D 405/06  (2006.01)
C07D 405/14  (2006.01)
C07D 413/14  (2006.01)
C07D 417/14  (2006.01)
A61K 31/4525  (2006.01)
A61K 31/454  (2006.01)
A61K 31/4545  (2006.01)

(52) U.S. Cl.
CPC .......... *C07D 405/06* (2013.01); *A61K 31/454* (2013.01); *A61K 31/4525* (2013.01); *A61K 31/4545* (2013.01); *C07D 405/14* (2013.01); *C07D 413/14* (2013.01); *C07D 417/14* (2013.01)

(58) Field of Classification Search
CPC .................................. C07D 405/06
See application file for complete search history.

(56) References Cited

FOREIGN PATENT DOCUMENTS

WO  WO 2008/076048 A1  6/2008
WO  WO 2009/142569 A1  11/2009
WO  WO 2009/142571 A1  11/2009

OTHER PUBLICATIONS

Psoriasis[online]; retrieved from the internet on Dec. 21, 2018 URL; https://www.webmd.com/skin-problems-and-treatments/psoriasis/understanding-psoriasis.*
Schäcke, Heike et al., "Mechanisms involved in the side effects of glucocorticoids," Pharmacology & Therapeutics, vol. 96, pp. 23-43 (2002).
International Search Report for International Application No. PCT/EP2016/071580, dated Nov. 2, 2016 (2 pages).
Written Opinion of the International Search Authority for International Application No. PCT/EP2016/071580, dated Nov. 2, 2016 (5 pages).

* cited by examiner

Primary Examiner — Shawquia Jackson
(74) Attorney, Agent, or Firm — Finnegan, Henderson, Farabow, Garrett & Dunner LLP

(57) ABSTRACT

The present invention relates to a compound according to formula (I)

(I)

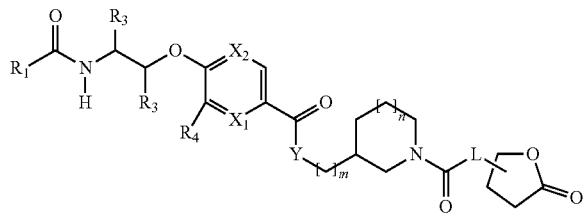

wherein $R_1$ is selected from the group consisting of 5- and 6-membered heteroaryl, $(C_1-C_6)$alkyl, $(C_3-C_6)$cycloalkyl, (4-6)-membered heterocycloalkyl and phenyl; $R_2$ is selected from $(C_1-C_3)$alkyl and halo$(C_1-C_3)$alkyl; $R_3$ is selected from phenyl, 5-membered heteroaryl and 6-membered heteroaryl; $R_4$ is selected from hydrogen, halogen, $(C_1-C_4)$alkyl and halo$(C_1-C_4)$alkyl; $X_1$ is selected from CH, C($R_b$) and N, $X_2$ is selected from CH and N; Y is selected from —NH— and —O—; m is 0 or 1; n is 0 or 1; L represents a bond, —O—, —NH— or —N($R_c$)—; or pharmaceutically acceptable salts, hydrates, or solvates thereof. The invention relates further to intermediates for the preparation of said compounds, to said compounds for use in therapy, to pharmaceutical compositions comprising said compounds, to methods of treating diseases with said compounds, and to the use of said compounds in the manufacture of medicaments.

17 Claims, 3 Drawing Sheets

NON-STEROIDAL GLUCOCORTICOID RECEPTOR MODULATORS FOR LOCAL DRUG DELIVERY

This application is a national stage filing under 35 U.S.C. § 371 of International Application No, PCT/EP2016/071580, filed on Sep. 13, 2016, which claims priority of European Patent Application No. 15185283.7, filed Sep. 15, 2015. The contents of these applications are each incorporated herein by reference.

FIELD OF THE INVENTION

This invention relates to novel non-steroidal compounds which are effective modulators of the glucocorticoid receptor and intermediates for the preparation thereof, to said compounds for use in therapy, to pharmaceutical compositions comprising said compounds, to methods of treating diseases with said compounds, and to the use of said compounds in the manufacture of medicaments.

BACKGROUND OF THE INVENTION

The glucocorticoid receptor (GR) is a member of the nuclear hormone receptor family of transcription factors, and a member of the steroid hormone family of transcription factors that when bound to a ligand promotes or suppresses the transcription of genes. Glucocorticoid receptor agonists occur naturally or may be prepared synthetically. Glucocorticoids (GC) which interact with GR are potent anti-inflammatory agents and have been used as such in controlling a wide range of allergic and inflammatory conditions, such as asthma, rheumatoid arthritis, eczema and psoriasis. Glucocorticoids have also been used for their immunosuppressive properties and for their anti-tumor effects.

Glucocorticoids have been applied locally to treat dermatitis, asthma, conjunctivitis, and other ophthalmological disorders.

However the use of glucocorticoids is limited by both topical and systemic side-effects, these effects include skin and muscle atrophy, osteoporosis, diabetes, impaired wound healing, susceptibility to infection, HPA dysfunction, adrenal atrophy, cataracts, peptic ulcers, hypertension, metabolic syndrome, and electrolyte imbalance [Shacke et al., Pharmacology and Therapeutics (2002), vol. 96(1), 23-43].

Side effects are usually more severe after systemic rather than topical application. However, even topical therapy can induce systemic adverse effects, as observed after cutaneous therapy for inflammatory dermatitis and pulmonary therapy for asthma. The side effects occur with different prevalence, in different organs, and after different durations of therapy. The severity ranges from more cosmetic aspects, for example teleangiectasia and hypertrichosis, to serious disabling and even life threatening situations (e.g. gastric hemorrhage). [Shacke et al., Pharmacology and Therapeutics (2002), vol. 96(1), 23-43].

The glucocorticoid receptor is activated by binding of the glucocorticoid hormone cortisol and its synthetic derivatives as well as by non-steroidal agonists. Thus steroid-based and non-steroidal-based glucocorticoid analogues are well known in the art.

WO2008/076048 discloses indazolyl ester and amide derivatives for the treatment of glucocorticoid receptor mediated disorders.

WO2009/142571 discloses phenyl and benzodioxinyl substituted indazoles derivatives as modulators of the glucocorticoid receptor.

WO2009/142569 discloses phenyl and pyridinyl substituted indazoles derivatives as modulators of the glucocorticoid receptor.

There is a continuous need for developing novel non-steroidal glucocorticoid receptor modulators (for example agonists, antagonists, partial agonists or partial antagonists). Particularly, development of non-steroidal glucocorticoids that retain the anti-inflammatory efficacy of glucocorticoids while minimizing the side-effects would be of great benefit to a large number of patients with inflammatory diseases. Development of topical non-steroidal glucocorticoids with high systemic clearance and/or short half-life may provide compounds having reduced side-effects while retaining the topical anti-inflammatory efficacy. For topical use the development of non-steroidal glucocorticoids with reduced photo toxicity would be beneficial.

SUMMARY OF THE INVENTION

It is an object of the present invention to provide novel non-steroidal compounds which are modulators, particularly agonists or partial agonists, of the glucocorticoid receptor and that have potent anti-inflammatory activity and which possess advantages with respect to side-effects, efficacy, toxicity and/or metabolism.

More particularly, the present invention provides novel compounds which are modulators, particularly agonists or partial agonists, of the glucocorticoid receptor; the compounds having anti-inflammatory effect and having a stability profile in biological tissue that implies that only a very low systemic exposure of the compounds will be observed upon e.g. topical administration. A particular advantage of some of the compounds of the present invention is that they have high clearance in human liver microsomes.

Furthermore, some of the compounds of the present invention are rapidly hydrolysed in human whole blood and some of the compounds of the present invention at the same time display stability towards enzymatic hydrolyses in human keratinocytes. Furthermore, some compounds of the present invention exhibit reduced photo toxicity.

Accordingly, the present invention relates to a compound according to formula (I)

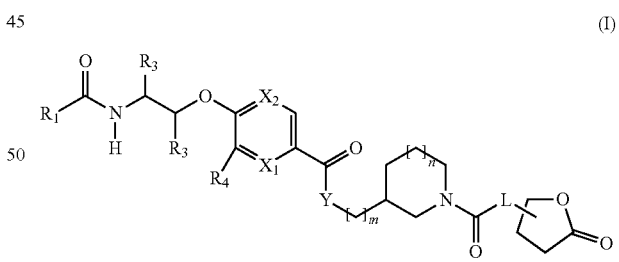

(I)

wherein
$R_1$ is selected from the group consisting of 5- and 6-membered heteroaryl, $(C_1-C_6)$alkyl, $(C_3-C_6)$cycloalkyl, (4-6)-membered heterocycloalkyl and phenyl, wherein said 5- and 6-membered heteroaryl, $(C_1-C_6)$alkyl, $(C_3-C_6)$cycloalkyl, (4-6)-membered heterocycloalkyl and phenyl is optionally substituted with one or more substituents independently selected from $(C_1-C_4)$alkyl, $(C_1-C_4)$alkoxy, halogen, hydroxyl and cyano;
$R_2$ is selected from $(C_1-C_3)$alkyl and halo$(C_1-C_3)$alkyl;
$R_3$ is selected from phenyl, 5-membered heteroaryl and 6-membered heteroaryl, wherein said phenyl, 5-membered heteroaryl and 6-membered heteroaryl are optionally substituted with one or more substituents independently selected from $R_5$;

$R_4$ is selected from hydrogen, halogen, $(C_1-C_4)$alkyl and halo$(C_1-C_4)$alkyl;

$R_5$ is selected from halogen, cyano, $(C_1-C_6)$alkyl, $(C_3-C_6)$cycloalkyl, $(C_1-C_6)$alkoxy, halo$(C_1-C_6)$alkyl, halo$(C_1-C_6)$alkoxy, hydroxy$(C_1-C_6)$alkyl, phenyl, 5-membered heteroaryl, 6-membered heteroaryl and —S(O)$_2$R$_a$, wherein R$_a$ represents $(C_1-C_4)$alkyl;

$X_1$ is selected from CH, C(R$_b$) and N, wherein R$_b$ represents halogen, $(C_1-C_4)$alkyl or halo$(C_1-C_4)$alkyl;

$X_2$ is selected from CH and N;

Y is selected from —NH— and —O—;

m is 0 or 1; n is 0 or 1;

L represents a bond, —O—, —NH— or —N(R$_c$)—, wherein R$_c$ represents $(C_1-C_4)$alkyl;

or pharmaceutically acceptable salts, hydrates or solvates thereof.

Furthermore, the present invention relates to a compound according to formula (I) for use in therapy.

Also, the present invention relates to a compound according to formula (I) for use in the prophylaxis, treatment or amelioration of inflammatory, allergic or proliferative dermatological diseases or conditions.

DETAILED DESCRIPTION OF THE INVENTION

Definitions

Figure 1:
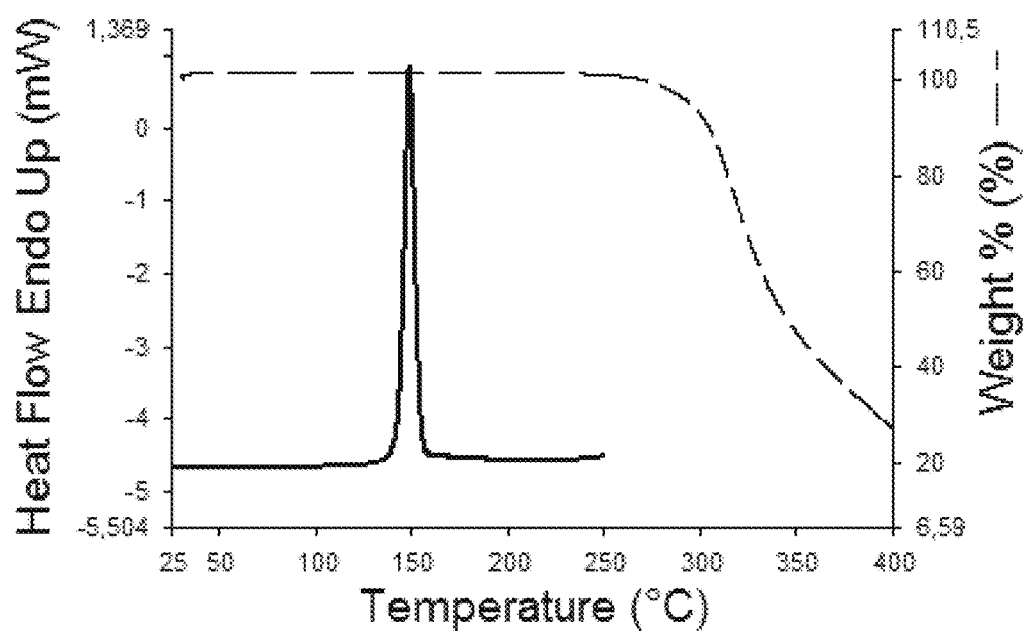
FIG. 1 is a graph showing the DSC (Differential scanning calorimetry) (solid) and the TGA (Thermo gravimetric analysis) (dash) curve of polymorph F of compound 37.

The term "alkyl" is intended to indicate a radical obtained when one hydrogen atom is removed from a branched or linear hydrocarbon. Said alkyl comprises 1-6, preferably 1-4, such as 1-3, such as 2-3 or such as 1-2 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, n-pentyl, isopentyl, neopentyl, n-hexyl and isohexyl.

The term "alkylene" is intended to indicate a divalent saturated aliphatic hydrocarbyl group preferably having from 1 to 6 and more preferably 1 to 3 carbon atoms that are either straight-chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)—) or (—CH(CH$_3$)CH$_2$—), and the like.

The terms "alkyloxy" and "alkoxy" are intended to indicate a radical of the formula —OR', wherein R' is alkyl as indicated herein, wherein the alkyl group is appended to the parent molecular moiety through an oxygen atom, e.g. methoxy (—OCH$_3$), ethoxy (—OCH$_2$CH$_3$), n-propoxy, iso-propoxy, butoxy, tert-butoxy, and the like. Thus the term "$(C_1-C_4)$alkoxy" is intended to indicate a radical of the formula —O$(C_1-C_4)$alkyl, e.g. methoxy (—OCH$_3$), ethoxy (—OCH$_2$CH$_3$), n-propoxy, isopropoxy, n-butoxy, iso-butoxy or tert-butoxy.

The term "alkylthio" is intended to indicate a radical of the formula —S—R', wherein R' is alkyl as indicated herein, wherein the alkyl group is appended to the parent molecular moiety through a sulphur atom, e.g. —S—CH$_3$ (methylthio) or —S—CH$_2$CH$_3$ (ethylthio).

The term "aryl" is intended to indicate a radical of aromatic carbocyclic rings comprising 6-13 carbon atoms, such as 6-9 carbon atoms, such as 6 carbon atoms, in particular 5- or 6-membered rings, including fused carbocyclic rings with at least one aromatic ring. If the aryl group is a fused carbocyclic ring, the point of attachment of the aryl group to the parent molecular moiety may be through an aromatic or through an alifatic carbon atom within the aryl group. Representative examples of aryl include, but are not limited to phenyl, naphthyl, indenyl, indanyl, dihydronaphtyl, tetrahydronaphtyl and fluorenyl.

The term "cyano" is intended to indicate a —CN group attached to the parent molecular moiety through the carbon atom.

The term "cycloalkyl" is intended to indicate a saturated cycloalkane hydrocarbon radical, comprising 3-6 carbon atoms, preferably 3-5 carbon atoms, such as 3-4 carbon atoms, e.g. cyclopropyl, cyclobutyl, cyclopentyl and cyclohexyl. Likewise the term "$(C_3-C_6)$cycloalkyl" is intended to indicate a saturated cycloalkane hydrocarbon radical, comprising 3-6 carbon atoms, e.g. cyclopropyl, cyclobutyl, cyclopentyl and cyclohexyl.

The term "haloalkyl" is intended to indicate an alkyl group as defined herein substituted with one or more halogen atoms as defined herein, e.g. fluoro or chloro, such as fluoromethyl, difluoromethyl or trifluoromethyl. Thus the term "halo$(C_1-C_3)$alkyl" is intended to indicate a $(C_1-C_3)$ alkyl group as defined herein substituted with one or more halogen atoms as defined herein, such as for example fluoromethyl, difluoromethyl, trifluoromethyl, difluoroethyl, trifluoroethyl or fluoropropyl. Likewise the term "halo$(C_1-C_6)$alkyl" is intended to indicate a $(C_1-C_6)$alkyl group as defined herein substituted with one or more halogen atoms as defined herein.

The terms "haloalkyloxy" and "haloalkoxy" are intended to indicate a haloalkyl group as defined herein which is appended to the parent molecular moiety through an oxygen atom, such as difluoromethoxy or trifluoromethoxy. Thus the term "halo$(C_1-C_6)$alkyloxy" is intended to indicate a halo $(C_1-C_6)$alkyl group as defined herein which is appended to the parent molecular moiety through an oxygen atom.

The term "halogen" is intended to indicate a substituent from the 7$^{th}$ main group of the periodic table, such as fluoro, chloro and bromo.

The term "heteroaryl" is intended to indicate radicals of monocyclic heteroaromatic rings comprising 5- or 6-membered ring which contains from 1-5 carbon atoms and from 1-5 heteroatoms selected from oxygen, sulphur and nitrogen, such as 1-3 carbon atoms and 2-4 heteroatoms selected from O, N and S, such as 2-3 carbon atoms and 2-3 heteroatoms selected from O, N and S, such as 1 carbon atom and 4 heteroatoms selected from O, N and S, such as 2 carbons atom and 3 heteroatoms selected from O, N and S, such as 3 carbon atoms and 2 heteroatoms selected from O, N and S, such as 4 carbon atoms and 1 heteroatom selected from O, N and S, such as 3 carbons atom and 3 heteroatoms selected from N, such as 4 carbons atom and 2 heteroatoms selected from N, such as 5 carbons atom and 1 heteroatom selected from N. The heteroaryl radical may be connected to the parent molecular moiety through a carbon atom or a nitrogen atom contained anywhere within the heteroaryl group. Representative examples of heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, tetrazolyl, thiadiazolyl, thiazolyl, thienyl, triazolyl.

The term "5-membered heteroaryl" is intended to indicate a heteroaryl as defined herein which comprise 5 ring-atoms, which contains from 1-4 carbon atoms and from 1-4 heteroatoms selected from oxygen, sulphur and nitrogen, such as 1-3 carbon atoms and 2-4 heteroatoms selected from O, N and S, such as 2-3 carbon atoms and 2-3 heteroatoms selected from O, N and S, such as 1 carbon atom and 4 heteroatoms selected from O, N and S, such as 2 carbons atom and 3 heteroatoms selected from O, N and S, such as 3 carbon atoms and 2 heteroatoms selected from O, N and S, such as 4 carbon atoms and 1 heteroatom selected from O, N and S. Representative examples of 5-membered heteroaryl groups include, but are not limited to, furanyl, imidazolyl, isothiazolyl, isoxazolyl, oxadiazolyl, oxazolyl, pyrazolyl, pyrrolyl, tetrazolyl, thiadiazolyl, thiazolyl, thienyl, triazolyl.

The term "6-membered heteroaryl" is intended to indicate a heteroaryl as defined herein which comprise 6 ring-atoms, which contains from 1-5 carbon atoms and from 1-5 heteroatoms selected from oxygen, sulphur and nitrogen, such as 2-4 carbon atoms and 2-4 heteroatoms selected from O, N and S, such as 2-3 carbon atoms and 3-4 heteroatoms selected from O, N and S, such as 3 carbons atom and 3 heteroatoms selected from N, such as 4 carbons atom and 2 heteroatoms selected from N, such as 5 carbons atom and 1 heteroatom selected from N. Representative examples of heteroaryl groups include, but are not limited to, pyrazinyl, pyridazinyl, pyridyl, pyrimidinyl.

The term "heterocycloalkyl" is intended to indicate a cycloalkane radical as described herein, wherein one or more carbon atoms are replaced by heteroatoms, comprising 1-6 carbon atoms, e.g. 2-5 or 2-4 carbon atoms, further comprising 1-3 heteroatoms, preferably 1 to 2 heteroatoms, selected from O, N, or S. The heterocycloalkyl radical may be connected to the parent molecular moiety through a carbon atom or a nitrogen atom contained anywhere within the heterocycloalkyl group. Representative examples of heterocycloalkyl groups include, but are not limited to azepanyl, azetidinyl, aziridinyl, dioxolanyl, dioxolyl, imidazolidinyl, morpholinyl, oxetanyl, piperazinyl, piperidinyl, pyrrolidinyl, tetrahydrofuranyl, tetrahydropyranyl, tetrahydrothiophenyl, tetrahydrothiopyranyl.

The term "(4-6) membered heterocycloalkyl" is intended to indicate a heterocyloalkyl as defined herein, comprising 4-6 ring-atoms, and comprising 1-5 carbon atoms, e.g. 2-5, 3-5, 4-5 or 2-4 carbon atoms, further comprising 1-5, 1-4 or 1-3 heteroatoms, preferably 1 to 2 heteroatoms, selected from O, N, or S. Representative examples of (4-6) membered heterocycloalkyl groups include azetidinyl, dioxanyl, dioxolanyl, imidazolidinyl, morpholinyl, oxetanyl, piperazinyl, piperidinyl, pyrrolidinyl, tetrahydrofuranyl, tetrahydropyranyl, tetrahydrothiopyranyl, tetrahydrothiophenyl, thietanyl.

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-6 carbon atoms, and preferably comprises 1-5, e.g. 1-4, e.g. 1-3, e.g. 1-2 carbon atoms. The term includes alkyl, cycloalkyl and aryl, as indicated herein.

The term "hydroxy" or "hydroxyl" is intended to indicate an —OH group attached to the parent molecular moiety through the oxygen atom.

The term "hydroxy($C_1$-$C_6$)alkyl" is intended to indicate a ($C_1$-$C_6$)alkyl group as defined herein substituted with one or more hydroxyl groups as defined herein (—OH), such as for example hydroxymethyl, hydroxyethyl, hydroxypropyl or dihydroxypropyl.

In some instances, the number of carbon atoms in a hydrocarbon radical (e.g. alkyl, cycloalkyl and aryl) is indicated by the prefix "($C_a$-$C_b$)", wherein a is the minimum number and b is the maximum number of carbons in the hydrocarbon radical. Thus, for example ($C_1$-$C_4$)alkyl is intended to indicate an alkyl radical comprising from 1 to 4 carbon atoms, ($C_1$-$C_6$)alkyl is intended to indicate an alkyl radical comprising from 1 to 6 carbon atoms and ($C_3$-$C_6$) cycloalkyl is intended to indicate a cycloalkyl radical comprising from 3 to 6 carbon ring atoms.

The term "hydroxyalkyl" is intended to indicate an alkyl group as defined above substituted with one or more hydroxy, e.g. hydroxymethyl, hydroxyethyl, hydroxypropyl.

The term "oxo" is intended to indicate an oxygen atom which is connected to the parent molecular moiety via a double bond (=O).

The term "thioxo" is intended to indicate a sulfur atom which is connected to the parent molecular moiety via a double bond (=S).

The group C(O) is intended to represent a carbonyl group (C=O) The term "pharmaceutically acceptable salt" is intended to indicate salts prepared by reacting a compound of formula I, which comprise a basic moiety, with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I comprising an acidic moiety may also be prepared by reaction with a suitable base such as sodium hydroxide, potassium hydroxide, magnesium hydroxide, calcium hydroxide, silver hydroxide, ammonia or the like, or suitable non-toxic amines, such as lower alkylamines, hydroxy-lower alkylamines, cycloalkylamines, or benzylamines, or L-arginine or L-lysine. Further examples of pharmaceutical acceptable salts are listed in Berge, S. M.; J. Pharm. Sci.; (1977), 66(1), 1-19, which is incorporated herein by reference.

The term "solvate" is intended to indicate a species formed by interaction between a compound, e.g. a compound of formula I, and a solvent, e.g. alcohol, glycerol or water, wherein said species are in a crystalline or a non-crystalline form. When water is the solvent, said species is referred to as a hydrate.

The term "treatment" as used herein means the management and care of a patient for the purpose of combating a disease, disorder or condition. The term is intended to include the delaying of the progression of the disease, disorder or condition, the amelioration, alleviation or relief of symptoms and complications, and/or the cure or elimination of the disease, disorder or condition. The term may also include prevention of the condition, wherein prevention is to be understood as the management and care of a patient for the purpose of combating the disease, condition or disorder and includes the administration of the active compounds to prevent the onset of the symptoms or complications. Nonetheless, prophylactic (preventive) and therapeutic (curative) treatments are two separate aspects.

All references, including publications, patent applications and patents, cited herein are hereby incorporated by reference in their entirety and to the same extent as if each reference were individually and specifically indicated to be incorporated by reference, regardless of any separately provided incorporation of particular documents made elsewhere herein.

Embodiments of the Invention

An embodiment of the present invention provides a compound of formula (I) wherein $R_1$ is selected from the group consisting of 5-membered heteroaryl, $(C_1-C_6)$alkyl, $(C_3-C_6)$cycloalkyl and (4-6)-membered heterocycloalkyl, wherein said 5-membered heteroaryl, $(C_1-C_6)$alkyl, $(C_3-C_6)$cycloalkyl and (4-6)-membered heterocycloalkyl is optionally substituted with one or more substituents independently selected from $(C_1-C_4)$alkyl, $(C_1-C_4)$alkoxy, halogen and hydroxyl.

An embodiment of the invention provides a compound of formula (I) wherein $R_2$ is methyl.

An embodiment of the invention provides a compound of formula (I) wherein $R_3$ is phenyl which is substituted with one or more substituents independently selected from $R_5$.

An embodiment of the invention provides a compound of formula (I) wherein $R_5$ is selected from halogen, $(C_1-C_6)$alkyl, $(C_3-C_6)$cycloalkyl and phenyl.

An embodiment of the invention provides a compound of formula (I) wherein $R_5$ is selected from bromo, methyl, ethyl, cyclopropyl and phenyl.

An embodiment of the invention provides a compound of formula (I) wherein $R_4$ is hydrogen.

An embodiment of the invention provides a compound of formula (I) wherein $X_1$ is selected from CH and N.

An embodiment of the invention provides a compound of formula (I) wherein $X_2$ is CH.

An embodiment of the invention provides a compound of formula (I) wherein $X_1$ is N, $X_2$ is CH and Y is —NH—.

An embodiment of the invention provides a compound of formula (I) wherein $X_1$ is CH, $X_2$ is CH and Y is —O—.

An embodiment of the invention provides a compound of formula (I) wherein m is 0 and n is 1.

An embodiment of the invention provides a compound of formula (I) wherein L represents a bond, —O— or —NH—.

An embodiment of the invention provides a compound of formula (I), wherein said compound is selected from N-[(3S)-1-[(3R)-5-oxotetrahydrofuran-3-carbonyl]-3-piperidyl]-5-[(1R,2S)-1-(p-tolyl)-2-[(2,2,2-trifluoroacetyl) amino]propoxy]pyridine-2-carboxamide, 5-[(1R,2S)-1-(4-cyclopropylphenyl)-2-[(2,2,2-trifluoroacetyl)amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-(2,2-difluoropropanoylamino)propoxy]-N-[(3S)-1-[(3R)-5-oxotetrahydrofuran-3-carbonyl]-3-piperidyl]pyridine-2-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isothiazole-3-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isothiazole-5-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]oxazole-2-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]thiazole-4-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]-3-methylisoxazole-5-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]oxazole-5-carboxamide, 5-[(1R,2S)-1-(4-cyclopropylphenyl)-2-[[(2S)-2-hydroxybutanoyl]amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[[(2R)-2-hydroxypropanoyl]amino]propoxy]-N-[(3S)-1-[(3R)-5-oxotetrahydrofuran-3-carbonyl]-3-piperidyl]pyridine-2-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isoxazole-5-carboxamide, 5-[(1R,2S)-1-(4-cyclopropylphenyl)-2-[[(2R)-2-hydroxybutanoyl]amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[(2-methoxyacetyl) amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[(2-hydroxy-2-methyl-propanoyl)amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-(3-hydroxypropanoylamino)propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[(1-hydroxycyclobutanecarbonyl)amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[(1-hydroxycyclopropanecarbonyl)amino]propoxy]-N-[(3S)-1-[(3R)-5-oxotetrahydrofuran-3-carbonyl]-3-piperidyl]pyridine-2-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]oxazole-4-carboxamide, 5-[(1R,2S)-1-(4-cyclopropylphenyl)-2-[[(2S)-tetrahydrofuran-2-carbonyl]amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[(2-hydroxyacetyl) amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[[(2R)-tetrahydrofuran-2-carbonyl]amino]propoxy]-N-[(3S)-1-[(3R)-5-oxotetrahydrofuran-3-carbonyl]-3-piperidyl]pyridine-2-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isoxazole-3-carboxamide,

[(3S)-1-[(3R)-5-oxotetrahydrofuran-3-carbonyl]-3-piperidyl] 4-[(1R,2S)-1-(4-cyclopropylphenyl)-2-[(2,2,2-trifluoroacetyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-(1,2,5-thiadiazole-3-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-[(5-methylthiazole-2-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-(thiazole-5-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-[(4-methyl-1,2,5-oxadiazole-3-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(5-methylthiazole-4-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(4-methylthiazole-5-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(5-methyl-1,3,4-oxadiazole-2-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(4-methylthiadiazole-5-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(4-methyloxazole-5-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(2-methoxyacetyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(2-methylpyrazole-3-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(2-methylthiazole-5-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[[(2R)-tetrahydrofuran-2-carbonyl]amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(3-methyltriazole-4-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-(1,2,4-oxadiazole-3-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-[(1-methylimidazole-2-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(3-methylisoxazole-5-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(5-methyl-1,2,4-oxadiazole-3-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(1-methylimidazole-4-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-(isothiazole-3-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-[(3-methylisoxazole-4-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-(thiazole-2-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-(isothiazole-5-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-[(5-methylisothiazole-4-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-(oxazole-2-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-(oxazole-5-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-(isoxazole-3-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-(thiadiazole-4-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-[(5-methylisoxazole-3-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-(isoxazole-5-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-(thiazole-4-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-[(3-methyl-1,2,4-oxadiazole-5-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(1-methylpyrazole-3-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-(2,2-difluoropropanoylamino)propoxy]benzoate, N-[(3R)-1-[(3R)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide, N-[(3R)-1-[(3S)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide, N-[(3R)-1-[(2S)-5-oxotetrahydrofuran-2-carbonyl]-3-piperidyl]-5-[(1R,2S)-1-(p-tolyl)-2-[(2,2,2-trifluoroacetyl)amino]propoxy]pyridine-2-carboxamide, N-[(3R)-1-[(2R)-5-oxotetrahydrofuran-2-carbonyl]-3-piperidyl]-5-[(1R,2S)-1-(p-tolyl)-2-[(2,2,2-trifluoroacetyl)amino]propoxy]pyridine-2-carboxamide, N-[(3S)-1-[(3S)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide, N-[(3S)-1-[(2S)-5-oxotetrahydrofuran-2-carbonyl]-3-piperidyl]-5-[(1R,2S)-1-(p-tolyl)-2-[(2,2,2-trifluoroacetyl)amino]propoxy]pyridine-2-carboxamide, N-[(3R)-1-[(3R)-5-oxotetrahydrofuran-3-carbonyl]pyrrolidin-3-yl]-5-[(1R,2S)-1-(p-tolyl)-2-[(2,2,2-trifluoroacetyl)amino]propoxy]pyridine-2-carboxamide, 5-[(1R,2S)-1-(4-ethylphenyl)-2-[(2,2,2-trifluoroacetyl)amino]propoxy]-N-[(3S)-1-[(3R)-5-oxotetrahydrofuran-3-carbonyl]-3-piperidyl]pyridine-2-carboxamide, 5-[(1R,2S)-1-(4-bromophenyl)-2-[(2,2,2-trifluoroacetyl)amino]propoxy]-N-[(3S)-1-[(3R)-5-oxotetrahydrofuran-3-carbonyl]-3-piperidyl]pyridine-2-carboxamide, N-[(3S)-1-[(3R)-5-oxotetrahydrofuran-3-carbonyl]-3-piperidyl]-5-[(1R,2S)-1-(4-phenylphenyl)-2-[(2,2,2-trifluoroacetyl)amino]propoxy]pyridine-2-carboxamide, N-[(3S)-1-[(3R)-5-oxotetrahydrofuran-3-carbonyl]-3-piperidyl]-4-[(1R,2S)-1-(p-tolyl)-2-[(2,2,2-trifluoroacetyl)amino]propoxy]benzamide,

[(3S)-1-[(3R)-5-oxotetrahydrofuran-3-carbonyl]-3-piperidyl] 4-[(1R,2S)-1-(p-tolyl)-2-[(2,2,2-trifluoroacetyl)amino]propoxy]benzoate, N-[(3S)-1-[[(3S)-5-oxotetrahydrofuran-3-yl]carbamoyl]-3-piperidyl]-5-[(1R,2S)-1-(p-tolyl)-2-[(2,2,2-trifluoroacetyl)amino]propoxy]pyridine-2-carboxamide, N-[(3S)-1-[[(3R)-5-oxotetrahydrofuran-3-yl]carbamoyl]-3-piperidyl]-5-[(1R,2S)-1-(p-tolyl)-2-[(2,2,2-trifluoroacetyl)amino]propoxy]pyridine-2-carboxamide,

[(3S)-2-oxotetrahydrofuran-3-yl] (3S)-3-[[5-[(1R,2S)-1-(p-tolyl)-2-[(2,2,2-trifluoroacetyl)amino]propoxy]pyridine-2-carbonyl]amino]piperidine-1-carboxylate,

[(3R)-2-oxotetrahydrofuran-3-yl] (3S)-3-[[5-[(1R,2S)-1-(p-tolyl)-2-[(2,2,2-trifluoroacetyl)amino]propoxy]pyridine-2-carbonyl]amino]piperidine-1-carboxylate,

[(3S)-5-oxotetrahydrofuran-3-yl] (3S)-3-[[5-[(1R,2S)-1-(p-tolyl)-2-[(2,2,2-trifluoroacetyl)amino]propoxy]pyridine-2-carbonyl]amino]piperidine-1-carboxylate or

[(34)-5-oxotetrahydrofuran-3-yl] (3S)-3-[[5-[(1R,2S)-1-(p-tolyl)-2-[(2,2,2-trifluoroacetyl)amino]propoxy]pyridine-2-carbonyl]amino]piperidine-1-carboxylate or pharmaceutically acceptable salts, hydrates or solvates thereof.

Any combination of two or more embodiments described herein is considered within the scope of the present invention.

The present invention includes all embodiments wherein $R_1$, $R_2$, $R_3$, $R_4$, $R_5$, $X_1$, $X_2$, Y, m, n and L are combined in any combination as anywhere described herein.

An embodiment of the present invention provides a compound of formula (Ia).

(Ia)

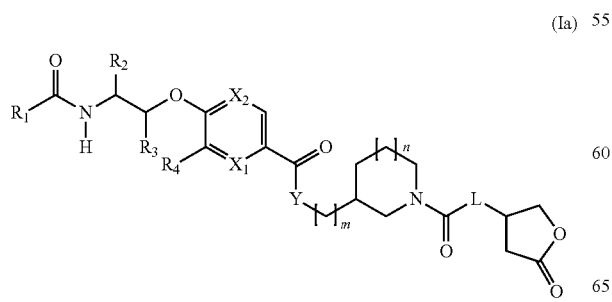

An embodiment of the present invention provides a compound of formula (Ib).

(Ib)

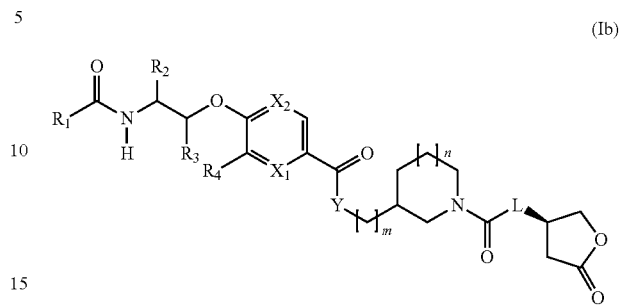

An embodiment of the present invention provides a compound of formula (Ic).

(Ic)

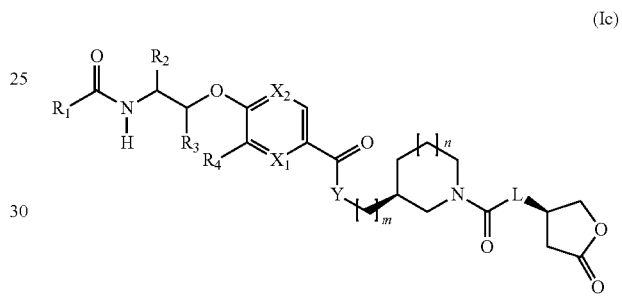

An embodiment of the present invention provides a compound of formula (Id).

(Id)

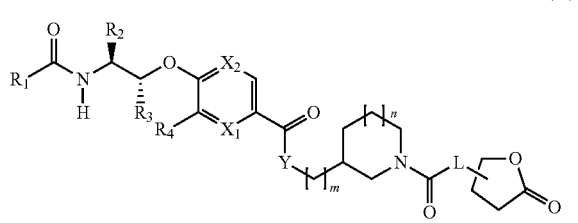

An embodiment of the present invention provides a compound of formula (Ie).

(Ie)

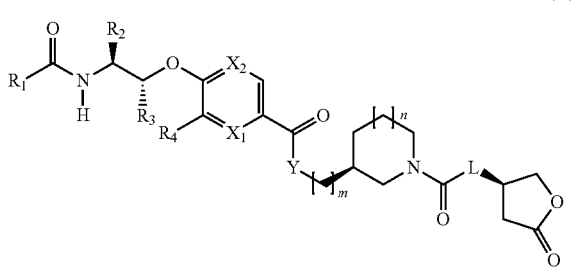

An embodiment of the present invention provides a compound of formula (If), wherein m is 0 and n is 1.

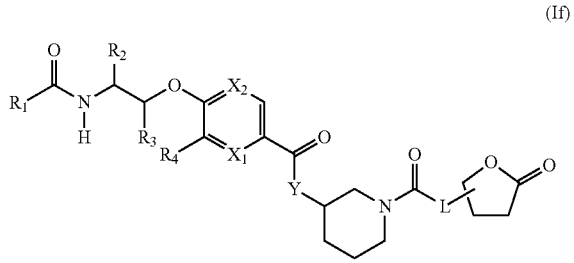

(If)

An embodiment of the present invention provides a compound of formula (Ig), wherein m is 0 and n is 1.

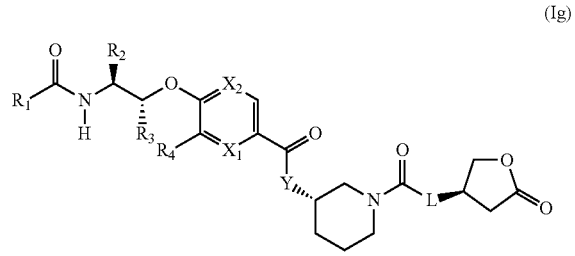

(Ig)

An embodiment of the present invention provides a compound of formula (Ih),

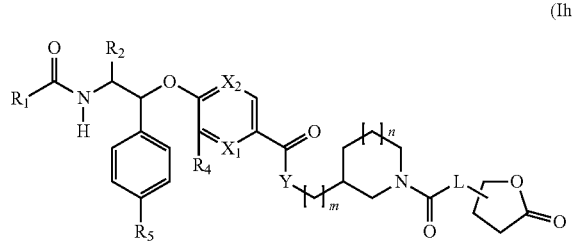

(Ih)

An embodiment of the invention provides a compound of formula I, said compound being [(3S)-1-[(3R)-5-oxotetrahydrofuran-3-carbonyl]-3-piperidyl] 4-[(1R,2S)-1-(4-cyclopropylphenyl)-2-[[(2R)-tetra hydrofuran-2-carbonyl]amino]propoxy]benzoate (Compound 37)

An embodiment of the invention provides a compound of formula I, said compound being N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isoxazole-3-carboxamide (Compound 23)

An embodiment of the invention provides a compound of formula I, said compound being N-[(3S)-1-[(3R)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide (Compound 1)

An embodiment of the present invention provides a compound of formula (I) wherein $R_2$ is methyl; $R_3$ is phenyl wherein said phenyl is substituted with one or more substituents independently selected from $R_5$; $R_4$ is hydrogen and $X_2$ is CH.

An embodiment of the present invention provides a compound of formula (I) wherein $R_3$ is phenyl which is substituted in the para-position with a substituent selected from $R_5$.

An embodiment of the present invention provides a compound of formula (I) wherein $R_1$ is 5-membered heteroaryl optionally substituted with one or more substituents independently selected from $(C_1-C_4)$alkyl, $(C_1-C_4)$alkoxy, halogen, hydroxyl and cyano; $R_2$ is methyl; $R_3$ is phenyl wherein said phenyl is substituted with one or more substituents independently selected from $R_5$; $R_4$ is hydrogen and $X_2$ is CH.

An embodiment of the present invention provides a compound of formula (I) wherein $R_1$ is $(C_1-C_6)$alkyl, optionally substituted with one or more substituents independently selected from $(C_1-C_4)$alkyl, $(C_1-C_4)$alkoxy, halogen, hydroxyl and cyano; $R_2$ is methyl; $R_3$ is phenyl wherein said phenyl is substituted with one or more substituents independently selected from $R_5$; $R_4$ is hydrogen and $X_2$ is CH.

An embodiment of the present invention provides a compound of formula (I) wherein $R_2$ is methyl; $R_3$ is phenyl wherein said phenyl is substituted with one or more substituents independently selected from $R_5$; $R_4$ is hydrogen; $X_2$ is CH; m is 0; n is 1 and L represents a bond.

An embodiment of the present invention provides a compound of formula (I) wherein $R_2$ is methyl; $R_3$ is phenyl wherein said phenyl is substituted with one or more substituents independently selected from $R_5$; $R_4$ is hydrogen; $X_1$ is CH; $X_2$ is CH; Y is —O—; m is 0; n is 1 and L represents a bond.

An embodiment of the present invention provides a compound of formula (I) wherein $R_2$ is methyl; $R_3$ is phenyl wherein said phenyl is substituted with one or more substituents independently selected from $R_5$; $R_4$ is hydrogen; $X_1$ is N; $X_2$ is CH; Y is —NH—; m is 0; n is 1 and L represents a bond.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline forms, such as polymorphs and pseudopolymorphs, and also mixtures thereof.

Compounds of formula I comprise asymmetrically substituted (chiral) carbon atoms which give rise to the existence of isomeric forms, e.g. enantiomers and possibly diastereomers. The present invention relates to all such isomers, either in optically pure form or as mixtures thereof (e.g. racemic mixtures or partially purified optical mixtures). Pure stereoisomeric forms of the compounds and the intermediates of this invention may be obtained by the application of procedures known in the art. The various isomeric forms may be separated by physical separation methods such as selective crystallization and chromatographic techniques, e.g. high pressure liquid chromatography using chiral stationary phases. Enantiomers may be separated from each other by selective crystallization of their diastereomeric salts which may be formed with optically active amines, such as l-ephedrine, or with optically active acids. Optically purified compounds may subsequently be liberated from said purified diastereomeric salts. Enantiomers may also be resolved by the formation of diastereomeric derivatives. Alternatively, enantiomers may be separated by chromatographic techniques using chiral stationary phases. Pure stereoisomeric forms may also be derived from the corresponding pure stereoisomeric forms of the appropriate starting materials, provided that the reaction occur stereoselectively or stereospecifically. Preferably, if a specific stereoisomer is desired, said compound will be synthesized by stereoselective or stereospecific methods of preparation. These methods will advantageously employ chiral pure starting materials.

The present invention includes pharmaceutically acceptable isotopically-labelled compounds of formula I wherein one or more atoms are replaced by atoms having the same atomic number, but an atomic mass or mass number different from the atomic mass number which predominates in nature. Examples of isotopes suitable for inclusion in the compounds includes isotopes of hydrogen, such as $^2$H and $^3$H, isotopes of carbon, such as $^{11}$C, $^{13}$C and $^{14}$C, isotopes of nitrogen, such as $^{13}$N and $^{15}$N isotopes of oxygen, such as $^{15}$O, $^{17}$O and $^{18}$O and isotopes of fluorine, such as $^{18}$F.

An embodiment of the invention provides the intermediates
5-[(1R,2S)-1-(p-Tolyl)-2-[(2,2,2-trifluoroacetyl)amino] propoxy]pyridine-2-carboxylic acid,
5-[(1R,2S)-1-(4-Ethylphenyl)-2-[(2,2,2-trifluoroacetyl) amino]propoxy]pyridine-2-carboxylic acid,
4-[(1R,2S)-1-(p-tolyl)-2-[(2,2,2-trifluoroacetyl)amino] propoxy]benzoic acid,
5-[(1R,2S)-1-(4-bromophenyl)-2-[(2,2,2-trifluoroacetyl) amino]propoxy]pyridine-2-carboxylic acid,
4-[(1R,2S)-1-(4-bromophenyl)-2-[(2,2,2-trifluoroacetyl) amino]propoxy]benzoic acid.

An embodiment of the invention provides the intermediates
N-[(3S)-3-piperidyl]-5-[(1R,2S)-1-(p-tolyl)-2-[(2,2,2-trifluoroacetyl)amino]propoxy]pyridine-2-carboxamide,
N-[(3R)-3-piperidyl]-5-[(1R,2S)-1-(p-tolyl)-2-[(2,2,2-trifluoroacetyl)amino]propoxy]pyridine-2-carboxamide,
5-[(1R,2S)-1-(4-ethylphenyl)-2-[(2,2,2-trifluoroacetyl) amino]propoxy]-N-[(3S)-3-piperidyl]pyridine-2-carboxamide,
5-[(1R,2S)-1-(4-cyclopropylphenyl)-2-[(2,2,2-trifluoroacetyl)amino]propoxy]-N-[(3S)-3-piperidyl]pyridine-2-carboxamide,
5-[(1R,2S)-1-(4-cyclopropylphenyl)-2-[[(2R)-tetra hydrofuran-2-carbonyl]amino]propoxy]-N-[(3S)-3-piperidyl] pyridine-2-carboxamide,
N-[(1S,2R)-2-(4-cyclopropylphenyl)-1-methyl-2-[[6-[[(3S)-3-piperidyl]carbamoyl]-3-pyridyl]oxy]ethyl]isoxazole-3-carboxamide,
5-[(1R,2S)-1-(p-tolyl)-2-[(2,2,2-trifluoroacetyl)amino] propoxy]-N-[(3R)-pyrrolidin-3-yl]pyridine-2-carboxamide,
5-[(1R,2S)-1-(4-bromophenyl)-2-[(2,2,2-trifluoroacetyl) amino]propoxy]-N-[(3S)-3-piperidyl]pyridine-2-carboxamide,
N-[(3S)-3-piperidyl]-4-[(1R,2S)-1-(p-tolyl)-2-[(2,2,2-trifluoroacetyl)amino]propoxy]benzamide,
[(3S)-3-piperidyl] 4-[(1R,2S)-1-(p-tolyl)-2-[(2,2,2-trifluoroacetyl)amino]propoxy]benzoate.

An embodiment of the invention provides the intermediates
Tert-butyl (3S)-3-[[5-[(1R,2S)-1-(p-tolyl)-2-[(2,2,2-trifluoroacetyl)amino]propoxy]pyridine-2-carbonyl]amino]piperidine-1-carboxylate,
tert-butyl (3S)-3-[[5-[(1R,2S)-1-(4-bromophenyl)-2-[(2,2,2-trifluoroacetyl)amino]propoxy]pyridine-2-carbonyl] amino]piperidine-1-carboxylate,
tert-butyl (3S)-3-[[5-[(1R,2S)-1-(4-cyclopropylphenyl)-2-[(2,2,2-trifluoroacetyl)amino]propoxy]pyridine-2-carbonyl]amino]piperidine-1-carboxylate,
tert-butyl (3S)-3-[[5-[(1R,2S)-1-(4-cyclopropylphenyl)-2-[[(2R)-tetrahydrofuran-2-carbonyl]amino]propoxy]pyridine-2-carbonyl]amino]piperidine-1-carboxylate,
tert-butyl (3S)-3-[[5-[(1R,2S)-1-(4-cyclopropylphenyl)-2-(isoxazole-3-carbonylamino)propoxy]pyridine-2-carbonyl]amino]piperidine-1-carboxylate,
tert-butyl (3S)-3-[4-[(1R,2S)-1-(4-bromophenyl)-2-[(2,2,2-trifluoroacetyl)amino]propoxy]benzoyl]oxypiperidine-1-carboxylate,
tert-butyl (3S)-3-[4-[(1R,2S)-1-(4-cyclopropylphenyl)-2-[(2,2,2-trifluoroacetyl)amino]propoxy]benzoyl]oxypiperidine-1-carboxylate,
tert-butyl (3R)-3-[[5-[(1R,2S)-1-(p-tolyl)-2-[(2,2,2-trifluoroacetyl)amino]propoxy]pyridine-2-carbonyl]amino]pyrrolidine-1-carboxylate,
tert-butyl (3S)-3-[[4-[(1R,2S)-1-(p-tolyl)-2-[(2,2,2-trifluoroacetyl)amino]propoxy]benzoyl]amino]piperidine-1-carboxylate and
tert-butyl (3S)-3-[4-[(1R,2S)-1-(p-tolyl)-2-[(2,2,2-trifluoroacetyl)amino]propoxy]benzoyl]oxypiperidine-1-carboxylate and
tert-butyl (3S)-3-[[5-[(1S,2S)-1-(p-tolyl)-2-[(2,2,2-trifluoroacetyl)amino]propoxy]pyridine-2-carbonyl]amino]piperidine-1-carboxylate In one or more embodiments of the present invention, the compounds of formula (I) as defined above are useful in therapy and in particular useful for treatment of atopic dermatitis, psoriasis or eczema.

Compounds of the present invention, optionally in combination with other active compounds, would be useful for the treatment of inflammatory, allergic or proliferative dermatological diseases or conditions, in particular for the treatment of atopic dermatitis, psoriasis or eczema.

An embodiment of the invention provides a compound according to general formula (I) for use in treatment of a disease, disorder or condition, which disease, disorder or condition is responsive of modulation of the glucocorticoid receptor.

An embodiment of the invention provides use of a compound according to formula (I) in the manufacture of a medicament for the prophylaxis, treatment or amelioration of inflammatory, allergic or proliferative dermatological diseases or conditions.

An embodiment of the invention provides the use of a compound according to general formula (I) in the manufacture of a medicament for the prophylaxis, treatment or amelioration of atopic dermatitis, psoriasis or eczema.

An embodiment of the invention provides a method of preventing, treating or ameliorating inflammatory, allergic or proliferative dermatological diseases or conditions, the method comprising administering to a person suffering from at least one of said diseases or disorders an effective amount of one or more compounds according to according to general formula (I), optionally together with a pharmaceutically acceptable carrier or one or more excipients, optionally in combination with other therapeutically active compounds.

An embodiment of the invention provides a method of preventing, treating or ameliorating inflammatory, allergic or proliferative atopic dermatitis, psoriasis or eczema, the method comprising administering to a person suffering from at least one of said diseases or disorders an effective amount of one or more compounds according to according to general formula (I).

Besides being useful for human treatment, the compounds of the present invention may also be useful for veterinary treatment of animals including mammals such as horses, cattle, sheep, pigs, dogs, and cats.

Pharmaceutical Compositions of the Invention

For use in therapy, compounds of the present invention are typically in the form of a pharmaceutical composition. The invention therefore relates to a pharmaceutical composition comprising a compound of formula I, optionally together with one or more other therapeutically active compound(s), together with a pharmaceutically acceptable excipient, vehicle or carrier(s). The excipient must be "acceptable" in the sense of being compatible with the other ingredients of the composition and not deleterious to the recipient thereof.

Conveniently, the active ingredient comprises from 0.0001-99.9% by weight of the formulation.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.001 mg and 1000 mg, preferably between 0.01 mg and 100 mg, such as 0.1-50 mg of a compound of formula I.

A suitable dosage of the compound of the invention will depend, inter alia, on the age and condition of the patient, the severity of the disease to be treated and other factors well known to the practising physician. The compound may be administered either orally, parenterally, topically, transdermally or interdermally+other routes according to different dosing schedules, e.g. daily, weekly or with monthly intervals. In general a single dose will be in the range from 0.001 to 400 mg/kg body weight. The compound may be administered as a bolus (i.e. the entire daily dosis is administered at once) or in divided doses two or more times a day.

In the context of topical treatment it may be more appropriate to refer to a "usage unit", which denotes a single dose which is capable of being administered to a patient, and which may be readily handled and packed, remaining as a physically and chemically stable unit dose comprising either the active material as such or a mixture of it with solid, semisolid or liquid pharmaceutical diluents or carriers.

The term "usage unit" in connection with topical use means a unitary, i.e. a single dose, capable of being administered topically to a patient in an application per square centimetre of the treatment area of from 0.001 microgram to 1 mg and preferably from 0.05 microgram to 0.5 mg of the active ingredient in question.

It is also envisaged that in certain treatment regimes, administration with longer intervals, e.g. every other day, every week, or even with longer intervals may be beneficial.

If the treatment involves administration of another therapeutically active compound it is recommended to consult *Goodman & Gilman's The Pharmacological Basis of Therapeutics*, 12th Ed., J. G. Hardman and L. E. Limbird (Eds.), McGraw-Hill 2011, for useful dosages of said compounds.

The administration of a compound of the present invention with one or more other active compounds may be either concomitantly or sequentially.

The formulations include e.g. those in a form suitable for oral (including sustained or controlled release), rectal, parenteral (including subcutaneous, intraperitoneal, intramuscular, intraarticular and intravenous), transdermal, intradermal, ophthalmic, topical, nasal, sublingual or buccal administration.

The formulations may conveniently be presented in dosage unit form and may be prepared by but not restricted to any of the methods well known in the art of pharmacy, e.g. as disclosed in Remington, *The Science and Practice of Pharmacy*, 21ed ed., 2005. All methods include the step of bringing the active ingredient into association with the carrier, which constitutes one or more accessory ingredients. In general, the formulations are prepared by uniformly and intimately bringing the active ingredient into association with a liquid carrier, semisolid carrier or a finely divided solid carrier or combinations of these, and then, if necessary, shaping the product into the desired formulation.

Formulations of the present invention suitable for oral and buccal administration may be in the form of discrete units as capsules, sachets, tablets, chewing gum or lozenges, each containing a predetermined amount of the active ingredient; in the form of a powder, granules or pellets; in the form of a solution or a suspension in an aqueous liquid or non-aqueous liquid, such as ethanol or glycerol; or in the form of a gel, a nano- or microemulsion, an oil-in-water emulsion, a water-in-oil emulsion or other dispensing systems. The oils may be edible oils, such as but not restricted to e.g. cottonseed oil, sesame oil, coconut oil or peanut oil. Suitable dispersing or suspending agents for aqueous suspensions include synthetic or natural surfactants and viscosifyring agents such as but not restricted to tragacanth, alginate, acacia, dextran, sodium carboxymethylcellulose, gelatin, methylcellulose, hydroxypropylmethylcellulose, hydroxypropylcellulose, carbomers, polyvinylpyrrolidone, polysorbates, sorbitan fatty acid esters. The active ingredients may also be administered in the form of a bolus, electuary or paste.

A tablet may be made by compressing, moulding or freeze drying the active ingredient optionally with one or more accessory ingredients. Compressed tablets may be prepared by compressing, in a suitable machine, the active ingredient(s) in a free-flowing form such as a powder or granules, optionally mixed by a binder and/or filler, such as e.g. lactose, glucose, mannitol starch, gelatine, acacia gum, tragacanth gum, sodium alginate, calcium phosphates, microcrystalline cellulose, carboxymethylcellulose, methylcellulose, hydroxypropylcellulose, hydroxypropylmethylcellulose, ethylcellulose, hydroxyethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent. Freeze dried tablets may be formed in a freeze-dryer from a solution of the drug substance. A suitable filler can be included.

Formulations for rectal administration may be in the form of suppositories in which the compound of the present invention is admixed with low melting point, water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. Furthermore, the formulation may contain cosolvent, solubilising agent and/or complexation agents. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compounds of formula I may be presented as a sterile, solid preparation, e.g. a freeze-dried powder, which is readily dissolved in a sterile solvent immediately prior to use.

Transdermal formulations may be in the form of a plaster, patch, microneedles, liposomal or nanoparticulate delivery systems or other cutaneous formulations applied to the skin.

Formulations suitable ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical, such as dermal, intradermal or ophthalmic administration include liquid or semisolid preparations such as liniments, lotions, gels, applicants, sprays, foams, film forming systems, micro needles, micro- or nano-emulsions, oil-in-water or water-in-oil emulsions such as creams, ointments or pastes; or solutions or suspensions such as drops.

For topical administration, the compound of formula I may typically be present in an amount of from 0.001 to 20% by weight of the composition, such as 0.01% to about 10%, such as 0.5%-5% but may also be present in an amount of up to about 100% of the composition.

Formulations suitable for nasal or buccal administration include powder, self-propelling and spray formulations, such as aerosols and atomisers. Such formulations are disclosed in greater detail in e.g. Modern Pharmaceutics, $2^{nd}$ ed., G. S. Banker and C. T. Rhodes (Eds.), page 427-432, Marcel Dekker, New York; Modern Pharmaceutics, $3^{th}$ ed., G. S. Banker and C. T. Rhodes (Eds.), page 618-619 and 718-721, Marcel Dekker, New York and Encyclopedia of Pharmaceutical Technology, vol. 10, J. Swarbrick and J. C. Boylan (Eds), page 191-221, Marcel Dekker, New York.

In addition to the aforementioned ingredients, the formulations of a compound of formula I may include one or more additional ingredients such as diluents, buffers, flavouring agents, colourant, surface active agents, thickeners, penetration enhancing agents, solubility enhancing agents preservatives, e.g. methyl hydroxybenzoate (including anti-oxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

Medical Use

Because of their ability to bind to the glucocorticoid receptor the compounds of the invention are useful as anti-inflammatory agents, and can also display anti-allergic, immunosuppressive and anti-proliferative actions. Thus a compound of formula (I) can be used as a medicament for the treatment or prophylaxis of one or more of the following pathological conditions (disease states) in a mammal:

Dermatological diseases, which coincide with inflammatory, allergic and/or proliferative processes:
Atopic dermatitis, Psoriasis, Eczema, such as, for example, atopic eczema, seborrheal eczema, nummular eczema or xerotic eczema, Exfoliative dermatitis, Erythematous diseases, triggered by different noxae, for example radiation or chemicals, burns, Acid burns, Bullous dermatoses, such as, for example, autoimmune pemphigus vulgaris or bullous pemphigoid, Diseases of the lichenoid group, Rosacea, Erythema exudativum multiform, Erythema nodosum, Balanitis, Pruritus, for example of allergic origins, Manifestation of vascular diseases, Vulvitis, alopecia such as alopecia areata, alopecia totalis or alopecia universalis, discoid lupus, Cutaneous T-cell lymphoma, Rashes of any origin or dermatoses, Pityriasis rubra pilaris.

Lung diseases, which coincide with inflammatory, allergic and/or proliferative processes: Chronically obstructive lung diseases of any origin, mainly bronchial asthma, chronic obstructive pulmonary disease, bronchitis of different origins, adult respiratory distress syndrome (ARDS), acute respiratory distress syndrome, Bronchiectases, all forms of restrictive lung diseases, mainly allergic alveolitis, all forms of pulmonary edema, mainly toxic pulmonary edema, sarcoidoses and granulomatoses, such as Bock's disease.

Eye diseases, which coincide with inflammatory, allergic and/or proliferative processes: allergic rhinitis, as well as chronic forms of keratitis such as adenoviral and Thygeson's keratitis, vernal keratoconjunctivitis, pingueculitis, episcleritis, uveitis, iritis, conjunctivitis, blepharitis, optic neuritis, chorioiditis, sympathetic ophthalmia.

Diseases of the ear-nose and throat area, which coincide with inflammatory, allergic and/or proliferative processes: Allergic rhinitis, hay fever, otitis externa, otitis media.

Allergies, which coincide with inflammatory, allergic and/or proliferative processes: All forms of allergic reactions, for example Quincke's edema, insect bites, contact dermatitis such as allergic and irritative, urticaria.

Methods of Preparation

The compounds of the present invention can be prepared in a number of ways well known to those skilled in the art of synthesis. The compounds of formula I may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. Not all compounds falling into a given class may be compatible with some of the reaction conditions required in some of the methods described. Such restrictions to the substituents which are compatible with the reaction conditions will be readily apparent to one skilled in the art and alternative methods can be used. The compounds of the present invention or any intermediate may be purified if required using standard methods well known to a synthetic organist chemist, e.g. methods described in "Purification of Laboratory Chemicals", $6^{th}$ ed. 2009, W. Amarego and C. Chai, Butterworth-Heinemann. Starting materials are either known compounds, commercially available, or they may be prepared by routine synthetic methods well known to a person skilled in the art.

Synthetic Routes

The following schemes illustrate the preparation of compounds of the formula (I), throughout which $X_1$, $X_2$, $R_1$, $R_2$, $R_3$, $R_4$, Y, L, m and n are as hereinbefore defined:

21

Scheme 1

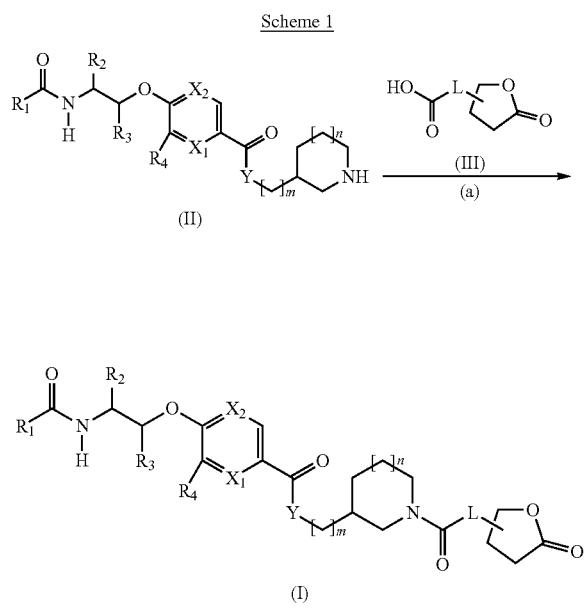

When L is a bond, then:

Acids suitable for use as compound (III) are commercially available, are known in the literature or can be prepared as outlined in scheme 5.1

Step (a): Acid (III) is reacted with amine (II) to give the compound of formula (I). This reaction is carried out by standard methods.

Coupling may be undertaken by using either (i) The acid chloride derivative of acid (III)+amine (II), with an excess of base in a suitable solvent, or (ii) The acid (III) with a conventional coupling agent+amine (II), optionally in the presence of a catalyst, with an excess of base in a suitable solvent.

Typically the conditions are as follows:

(i) acid chloride of acid (III) (generated in-situ), an excess of amine (II), optionally with an excess of 3° amine such as $Et_3N$, Hünig's base or NMM, in DCM or THF, without heating for 1 to 24 hrs, or (ii) acid (III), WSCDI/DCC and HOBT/HOAT, an excess of amine (II), with an excess of NMM, $Et_3N$, Hünig's base in THF, DCM or EtOAc, at room temperature for 4 to 48 hrs; or, acid (III), PYBOP®/PyBrOP®/Mukaiyama's reagent, an excess of amine (II), with an excess of NMM, $Et_3N$, Hünig's base in THF, DCM or EtOAc, at room temperature for 4 to 24 hrs.

The preferred conditions are: 1.5 eq. acid chloride of acid (III) (generated in-situ), 1 eq. amine (II), in DCM at room temperature for 16 hours, or the 1.5 carboxylic acid (III), 1 eq HOBt, 1 eq. WSCDI, 1 eq. amine (II) in dichloromethane at room temperature for 18 hours.

22

When L is NH, N($R_c$) or O, then:
Compound (I) can be prepared as outlined in scheme 1.1

Scheme 1.1

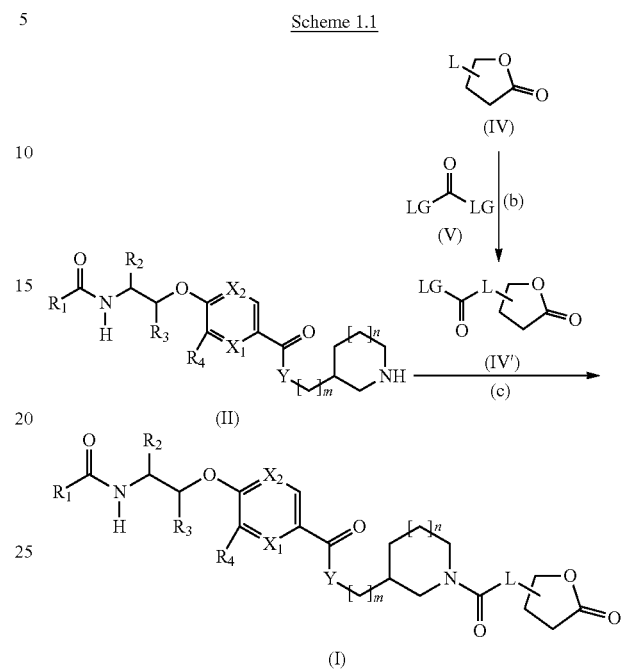

Amines and alcohols suitable for use as compound (IV) are commercially available or are known in the literature.

LG represents a leaving group, typically chloro, compounds suitable for use as compound (V) are known in the literature or commercially available.

Step (b): The amine or alcohol (IV) is transformed in situ to the reactive intermediate (IV'), if LG is Chloro then (IV') is an isocyanate, carbamoyl chloride or carbonochloroimidate.

Typical conditions are, (i) The amine or alcohol (IV) in a suitable aprotic solvent with phosgene, triphosgene, diphosgene or CDI in the presence of a tertiary base, without heating for 1 to 24 hr.

Preferred conditions are: The amine or alcohol (IV) in DCM with triphosgene (0.4 eq) with Hünig's base (2 eq.), without heating for 2 hr.

Step (c): The reactive intermediate (IV') is reacted with amine (II). Typical conditions are, (i) The reactive intermediate (IV') in a suitable aprotic solvent with amine (II) in the presence of a tertiary base like NMM, Hünig's base, triethylamine without heating for 1 to 24 hr.

Preferred conditions are: The reactive intermediate (IV') (2 eq.) with amine (II) in with triethylamine (3 eq) in DMF at room temperature for 1 hr.

Alternatively, when L is NH, N($R_c$) or O, then
Compound (I) can be prepared as outlined in scheme 1.2

Scheme 1.2

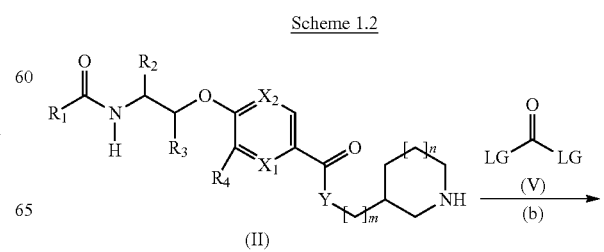

-continued

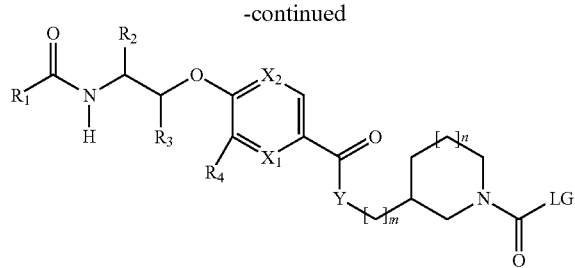

(II')

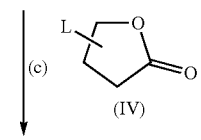

(IV)

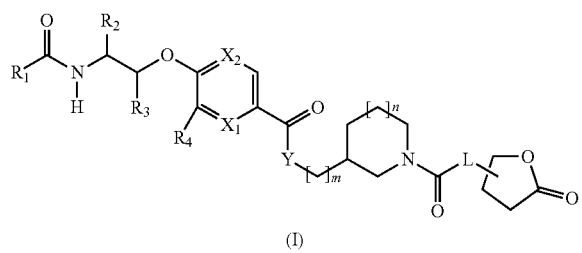

(I)

Amines and alcohols suitable for use as compound (IV) are commercially available or are known in the literature.

LG represents a leaving group, for example chloro, compounds suitable for use as compound (V) are known in the literature or commercially available or can be prepared as outlined in scheme 6.1.

Step (b): The amine (II) is transformed in situ to the reactive intermediate (II'), if LG is Chloro then (IV') is a carbamoyl chloride.

Typical conditions are, (ii) The amine (II) in a suitable aprotic solvent with phosgene, triphosgene, diphosgene or CDI in the presence of a tertiary base, without heating for 1 to 24 hr.

Preferred conditions are: The amine (II) in DCM with triphosgene (0.4 eq) with Hünig's base (2 eq.), without heating for 2 hr.

Step (c): The reactive intermediate (II') is reacted with amine or alcohol (IV). Typical conditions are, (ii) The reactive intermediate (II') in a suitable aprotic solvent with amine or alcohol (II) in the presence of a tertiary base like NMM, Hünig's base, triethylamine or strong base like sodium hydride with heating for 1 to 24 hr.

Preferred conditions are: The reactive intermediate (II') with amine or alcohol (IV)(2 eq) with triethylamine (3 eq) in DMF at 50° C. for 5 hr.

Compounds suitable for use as compounds (II) can be prepared as shown in scheme 2.1 and 2.2.

Scheme 2.1

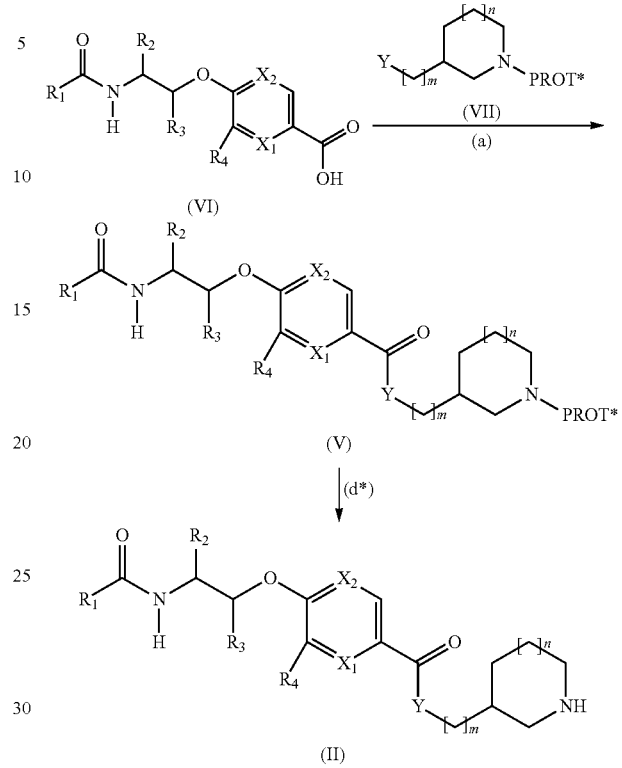

PROT* represents a suitable protecting group for nitrogen. Standard methodology for nitrogen protecting groups is used, such as that found in textbooks, (e.g. "Protecting Groups in Organic Synthesis" by T. W. Greene and P. Wutz).

Compounds suitable for use as compound (VII) are commercially available or are known in the literature.

Step (d*): Deprotection of compound (V) is undertaken using standard methodology, as described in "Protecting Groups in Organic Synthesis" by T. W. Greene and P. Wutz".

When PROT* is Boc the preferred method is hydrogen chloride in a suitable solvent such as 1,4-dioxane at room temperature for 1-16 hours, or a solution of trifluoroacetic acid in dichloromethane for 1-2 hours.

When PROT* is CBz the preferred method is hydrogenolysis using a suitable palladium catalyst in a solvent such as ethanol.

When PROT* is an allyl carbamate, preferred conditions are thiobenzoic acid and a suitable palladium catalyst such as $Pd_2(dba)_3$ with a suitable phosphine additive such as 1,4-bis(diphenylphosphino)butane in tetrahydrofuran for 20 minutes.

Step (a): Acid (VI) is reacted with amine or alcohol (VII) to give the compound of formula (V). This reaction is carried out by standard methods.

Coupling may be undertaken by using either (i) The acid chloride derivative of acid (VI)+amine or alcohol (VII), with an excess of base in a suitable solvent, or (ii) The acid (VI) with a conventional coupling agent+amine or alcohol (VII), optionally in the presence of a catalyst, with an excess of base in a suitable solvent.

Typically the conditions are as follows:

(ii) acid chloride of acid (VI) (generated in-situ), an excess of amine or alcohol (VII), optionally with an excess of 3° amine such as Et₃N, Hünig's base or NMM, in DCM or THF, without heating for 1 to 24 hrs, or when Y is NH, (iii) acid (VI), WSCDI/DCC and HOBT/HOAT, an excess of amine (VII), with an excess of NMM, Et₃N, Hünig's base in THF, DCM, DMF or EtOAc, at room temperature for 4 to 48 hrs; or, acid (VI), PYBOP®/PyBrOP®/Mukaiyama's reagent, an excess of amine (VII), with an excess of NMM, Et₃N, Hünig's base in THF, DCM, DMF or EtOAc, at room temperature for 4 to 24 hrs.

or when Y is O (iv) acid (VI), EDC an excess of alcohol (VII) in DCM, THF or DMF with DMAP at room temperature for 1 to 24 hrs.

The preferred conditions are: 1.5 eq. acid chloride of acid (VI) (generated in-situ), 1 eq. amine or alcohol (VII), in DCM at room temperature for 16 hours, or the 1 eq carboxylic acid (VI), 1 eq HOBt, 1 eq. WSCDI, 1.5 eq. amine (VII) in DMF at room temperature for 18 hours or or the 1.2 eq carboxylic acid (VI), EDC, 1 eq. alcohol (VII) with DMAP (2.5 eq) in DMF at room temperature for 18 hours.

PROT and PROT* represent suitable orthogonal protecting groups for nitrogen which by definition can be deprotected independently of each other. Standard methodology for nitrogen protecting groups is used, such as that found in textbooks, (e.g. "Protecting Groups in Organic Synthesis" by T. W. Greene and P. Wutz).

Compounds suitable for use as compound (X) are commercially available or are known in the literature.

Compounds (V') can be prepared in an analogous manner to Compound (V) as outlined in scheme 2.1

Typically, PROT is TFA, FMOC and PROT* is BOC, CBz but those skilled in the art would realize that PROT could be BOC, CBz and PROT* TFA, FMOC.

When PROT is TFA and PROT* is BOC

Step (d): Compound (IX) in protic solvent like ethanol, methanol or aqueous miscible solvents like dioxan, THF, DMF, DMSO with sodium hydroxide, lithium hydroxide or potassium hydroxide.

Preferably,

Compound (IX) in dioxan with 1.2 eq of lithium hydroxide at room temperature for 20 hrs.

Compounds (VI) can be prepared as outlined in Scheme 3.1

Scheme 2.2

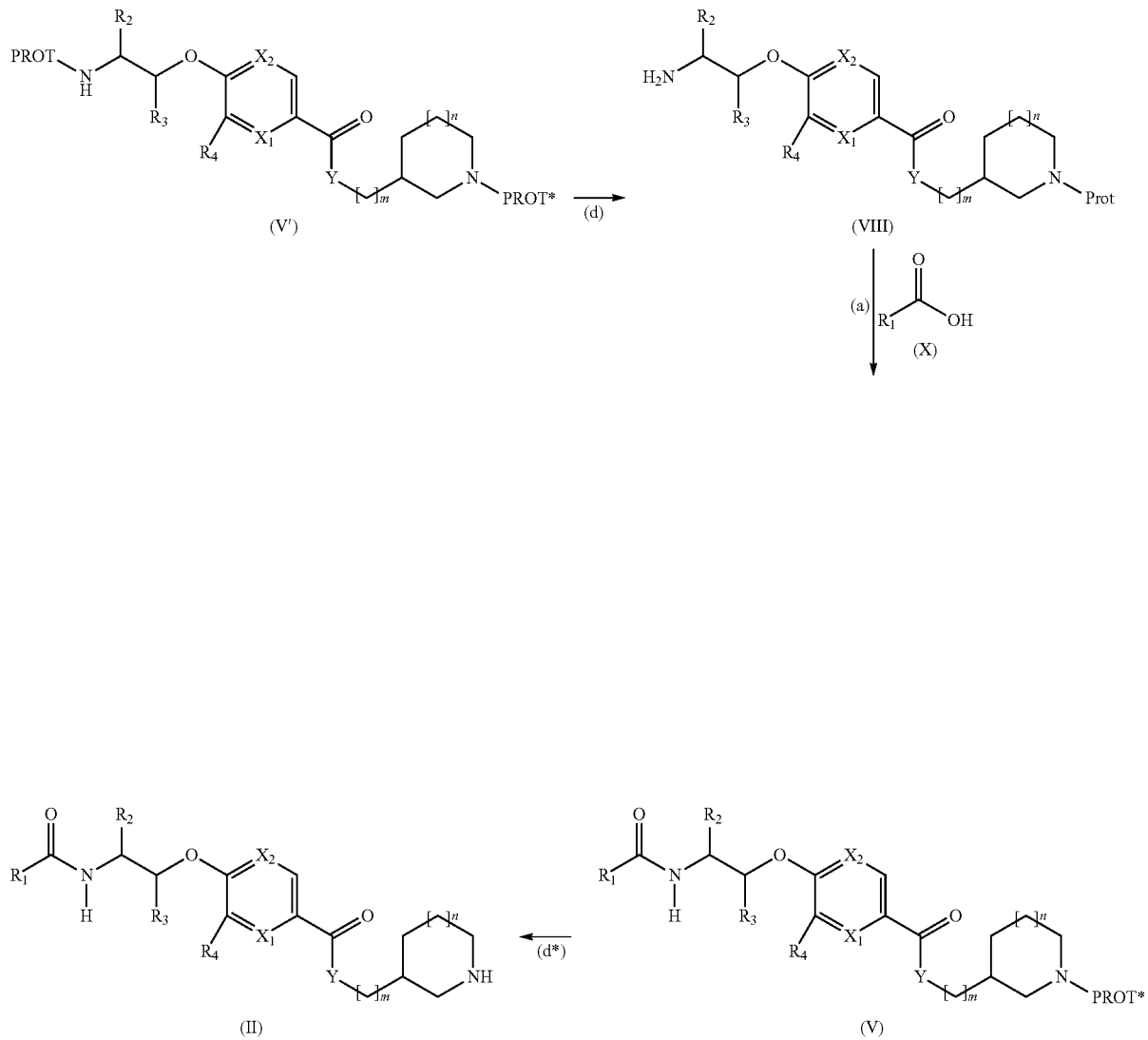

Scheme 3.1

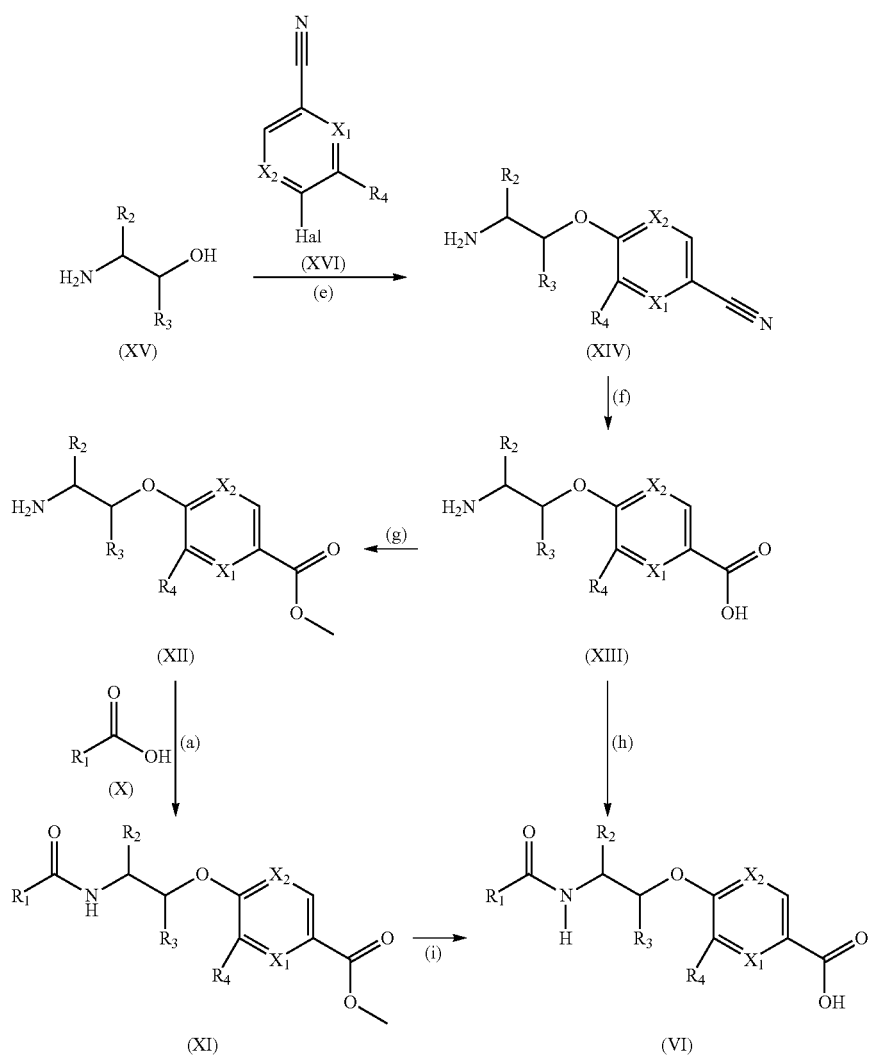

Nitriles suitable for use as compounds (XVI) are commercially available, known in the literature or can be prepared from commercially available intermediates using methods outlined in, amongst others, Kondolff, Tetrahedron 60(17), 3813 (2004), Mormino et al., Organic letters, 16(6), 1744-47, 2014, Maillard PCT 2004024081 and Tet. Letters 2002, 43, 6987-6990.

Step (e): The amino alcohol (XV) with a strong base like a metal hydride or metal hexamethyldisilazide in a suitable aprotic solvent with nitrile (XVI), at 0° C. to 70° C. for 1 to 6 hrs.

When $X_1$ is N

Preferrably, amino alcohol (XV) with 1.5 eq. NaH in THF at 50° C. for 1 hr, cooled to 0° C. and 1.2 eq. of nitrile (XVI) added, kept at 0° C. for 4 to 8 hrs.

When $X_1$ is CH, $C(R_b)$

Preferrably, amino alcohol (XV) with 1.5 eq. NaH in THF at 50° C. for 1 hr, 1.2 eq nitrile (XVI) added, heated at 50° C. for 1 to 4 hrs.

Step (f): The amino nitrile (XIV) in a protic solvent like ethanol, methanol or aqueous miscible solvents like dioxan, THF, DMF, DMSO with sodium hydroxide, lithium hydroxide or potassium hydroxide, with heating for 1 hr to 48 hrs.

Preferably, when $X_1$ is N,

Compound (XIV) in ethanol and water with 5 eq of sodium hydroxide at 85° C. for 2 hrs.

When $X_1$ is CH, $C(R_b)$,

Compound (XIV) in ethanol and water with 5 eq of sodium hydroxide at 85° C. for 16 to 48 hrs.

Step (g): The amino acid (XIII) in methanol with a strong acid catalyst, with heating. Typically, the amino acid (XIII) in anhydrous methanol with 0.2 eq. 98% sulphuric acid at 85° C. for 16 hrs to 48 hrs.

Step (h): The amino acid (XIII) in a suitable solvent like diethyl ether, THF, dioxan, acetonitrile, DCM with excess acid chloride or anhydride of acid (X) optionally in the presence of a 3° base like, triethylamine, NMM, pyridine or aqueous inorganic base, optionally with heating for 1 to 6 hrs.

Typically, the amino acid (XIII) in DCM with excess acid chloride of acid (X) in the presence aqueous excess aqueous sodium hydroxide for 1 to 6 hrs.

Or if R₁ is CF₃,
the amino acid (XIII) in acetonitrile pyridine with excess TFAA in the presence of excess pyridine at 0° C. for 1 to 4 hr.

Step (i): The amino ester (XI) in a protic solvent like ethanol, methanol or aqueous miscible solvents like dioxan, THF, DMF, DMSO with sodium hydroxide, lithium hydroxide or potassium hydroxide, optionally with heating for 1 hr to 48 hrs.

When $X_1$ is N and $R_1$ is $CF_3$

Typically, the amino ester (XI) in methanol with 1.5 eq. sodium hydroxide at room temperature for 6 hr, When $X_1$ is CH, $C(R_b)$ and $R_1$ is not $CF_3$ Typically,
the amino ester (XI) in methanol with 1.5 eq. sodium hydroxide at with heating to 60° C. for 2 hr.

Amino alcohols suitable for use as compound (XV) are commercially available or are known in the literature or can be prepared using methods outlined in scheme 4.1 and specifically in schemes 7.1 and 7.2.

Scheme 4.1

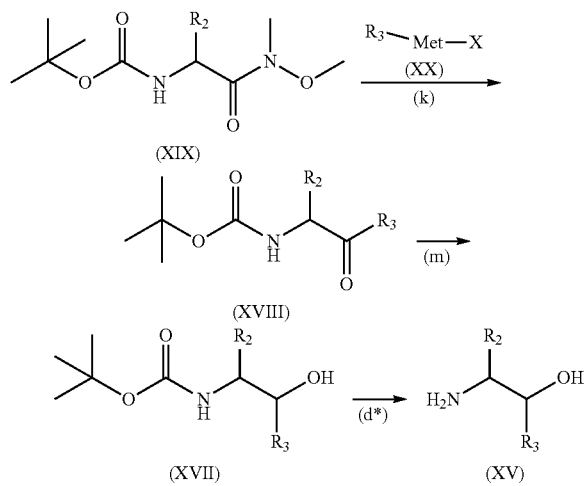

Scheme 5.1

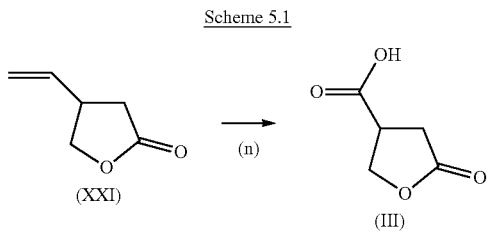

Compounds (XXI) are known in the literature.

Step (n): Alkene (XXI) in a suitable solvent under oxidative cleavage conditions. Typically, alkene (XXI) in acetonitrile, carbon tetrachloride and water with 5% ruthenium(III) chloride and excess sodium periodate.

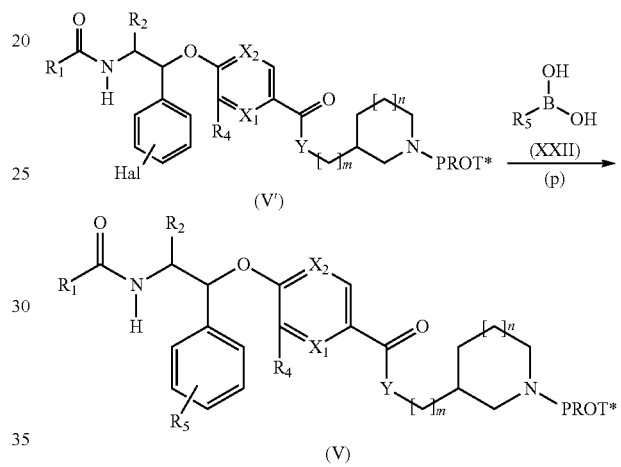

Compounds suitable for use as amide (XIX) are known in the literature or are commercially available.

Met represents a metal, typically Li, Mg, Zn

X represents a halogen, typically Chloro, bromo or iodo.

Step (k): Amide (XIX) in a suitable aprotic solvent like THF, diethyl ether, dioxin with organometallic (XX) at low temperature for 1 hr to 24 hr.

Typically, amide (XIX) with 2.5 eq. of Grignard (XX) (Met is Mg) in THF at 0° C. to room temperature for 6 hrs to 18 hrs.

Step (m): Ketone (XVIII) in a suitable solvent with a reducing agent.

Typically,
(i) Ketone (XVIII) in aqueous alcohol, methanol, ethanol or IPA with sodium/lithium/potassium borohydride at room temperature for 1 to 4 hr.
(ii) Ketone (XVIII) in toluene and IPA with catalytic aluminium isopropoxide with heating for 6 to 24 hrs.
(iii) Ketone (XVIII) in aprotic solvent like THF, diethyl ether or dioxan at low temperature with Dibal.

Preferably, Ketone (XVIII) in toluene and IPA with 0.5 eq. aluminium isopropoxide at 60° C. for 8 hrs.

Compounds suitable for use as boronic acid (or ester) (XXII) are commercially available or known in the literature—

Hal represents a halide Iodo, bromo or chloro.

Step (p): Halide (V') in a suitable solvent with boronic acid (or ester) (XXII) in the presence of a palladium catalyst and phosphine ligand, in the presence of a base with heating for 1 to 48 hrs.

Typically, Halide (V') with 0.05 eq. palladium (II) acetate, 0.15 eq. tricylohexylphosphine, 3 eq. potassium acetate, 1.5 eq boronic acid (XXII) in toluene/water heated in an inert atmosphere (nitrogen or argon) to 100° C. for 6 hrs.

It will be appreciated by those skilled in the art that when appropriate the order in which steps are undertaken can be changed but may require additional additional protection/deprotection steps for sensitive functionality. Standard methodology for protecting groups is used, such as that found in textbooks, (e.g. "Protecting Groups in Organic Synthesis" by T. W. Greene and P. Wutz, John Wiley & Sons Inc.).

GENERAL PROCEDURES, PREPARATIONS AND EXAMPLES

The following abbreviations have been used throughout:
$Et_3N$ Triethylamine
Hünig's base Diisopropylethylamine
NMM N-Methylmorpholine
DCM Dichloromethane
THF Tetra hydrofuran EDAC/WSCDI N-(3-Dimethylaminopropyl)-N'-ethylcarbodiimide hydrochloride
DCC N, N'-Dicyclohexylcarbodiimide
HOBt 1-Hydroxybenzotriazole
HOAt 1-Hydroxy-7-azabenzotriazole
EtOAc Ethyl acetate
PyBOP® (Benzotriazol-1-yloxy)tripyrrolidinophosphonium hexafluorophosphate
PyBrOP® Bromotripyrrolidinophosphonium hexafluorophosphate
Mukaiyama's reagent 1-methyl-2-chloropyridinium iodide
CDI Carbonyldiimidazole
DMF Dimethylformamide $^1$H nuclear magnetic resonance (NMR) spectra were recorded at 300 MHz unless otherwise specified. Chemical shift values (δ, in ppm) are quoted relative to internal tetramethylsilane (δ=0.00) standards. The value of a multiplet, either defined doublet (d), triplet (t), quartet (q) or not (m) at the approximate midpoint is given unless a range is quoted. (br) indicates a broad peak, whilst (s) indicates a singlet. All NMR spectra are recorded in DMSO-$d_6$ unless another solvent is stated.

The organic solvents used were usually anhydrous. The solvent ratios indicated refer to v:v unless otherwise noted.

UPLC-MS Method 1.
Column: Waters Aquity UPLC HSS T3 1.8 μm, 2.1×50 mm.
Column temperature: 60° C.
UV: PDA 210-400 nm.
Injection volume: 2 μl.
Eluents: A: 10 mM Ammonium acetate with 0.1% formic acid.
B: 100% Acetonitrile with 0.1% formic acid.
Gradient:

| Time | A % | B % | Flow |
|---|---|---|---|
| 0.0 | 95 | 5 | 1.2 |
| 0.9 | 5 | 95 | 1.2 |
| 0.91 | 5 | 95 | 1.3 |
| 1.2 | 5 | 95 | 1.3 |
| 1.21 | 5 | 95 | 1.2 |
| 1.4 | 95 | 5 | 1.2 |

MS: Electrospray switching between positive and negative ionisation.
Instruments: Waters Aquity UPLC, Waters SQD
UPLC-MS Method 2:
Column: Acquity UPLC HSS T3 1.8 μm; 2.1×50 mm
Flow: 0.7 ml/min
Column temp: 40° C.
Mobile phases: A: 10 mM Ammonium acetate+0.1% formic acid
B: 100% Acetonitrile+0.1% formic acid
UV: 240-400 nm
Injection volume: 2 μl
Gradient:

| Time | A % | B % |
|---|---|---|
| 0.0 | 99% A | 1% B |
| 0.5 | 94% A | 6% B |
| 1.0 | 94% A | 6% B |
| 2.6 | 5% A | 95% B |
| 3.8 | 5% A | 95% B |
| 3.81 | 99% A | 1% B |
| 4.8 | 99% A | 1% B |

UPLC (inlet method): XE Metode 7 CM
MS—method: PosNeg_50_1000
Instruments: Waters Acquity UPLC, Waters LCT Premier XE X-ray powder diffraction (XRPD): The diffractogram was obtained on a conventional X'pert PRO MPD diffractometer from PANalytical configured with transmission geometry and equipped with a PIXcel detector. A continuous 2θ scan range of 3-30° was used with a CuKα radiation λ=1.5418 Å source and a generator power of 40 KV and 45 mA. A 2θ step size of 0.0070°/step with a step time of 148.92 s was used. Instrument calibration was performed using a silicon reference standard. The sample was gently flattened onto a well in a 96-well plate for transmission measurements. The well plate was moved forward and backward in the x direction and the experiment was performed at room temperature.

Differential scanning calorimetry (DSC): DSC experiment was carried out using a Perkin Elmer DSC8500 system. About 1.7 mg of sample was used for the measurement. An aluminium pan was used for the analysis and was sealed by applying pressure by hand and pushing each part of the pan together. The temperature was ramped from −60 to 250° C. at 20° C./min. Nitrogen was used as the purge gas with a flow rate of 20 mL/min.

Thermo gravimetric analysis (TGA): TGA experiment was conducted using a Perkin Elmer Pyris 1 TGA instrument. About 1.4 mg of sample was loaded into a ceramic pan for the measurement. The sample temperature was ramped from 25 to 500° C. at 10° C./min. Nitrogen was used as the purge gas at a flow rate of 40 mL/min.

Single-crystal X-ray diffraction data were collected using a SuperNova, Dual diffractometer with an Atlas CCD area detector (Temperature: 120(2) K; Cu Kα Radiation λ=1.5418 Å; data collection method: ωscans). Further details can be found in table 3. Program(s) used to solve structure: CrysAlisPro, Agilent Technologies, Version 1.171.37.34 (release 22 May 2014 CrysAlis171 .NET), ShelXL (Sheldrick, 2008) used to refine structure and Olex2 (Dolomanov et al., 2009) for ORTEP drawings.

The given error ranges in this application for the spectroscopic characteristics, including those in the claims, may be more or less depending of factors well known to a person skilled in the art of spectroscopy and may for example depend on sample preparation, such as particle size distribution, or if the crystal form is part of a formulation, on the composition of the formulation, as well as instrumental fluctuations, and other factors.

PREPARATIONS

Scheme 7.1

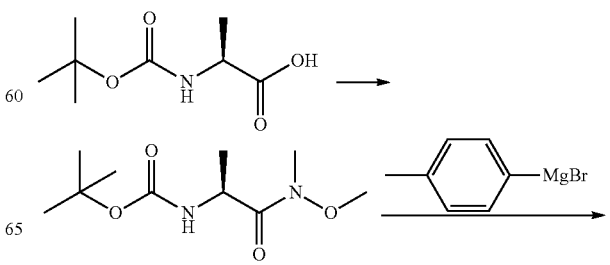

-continued

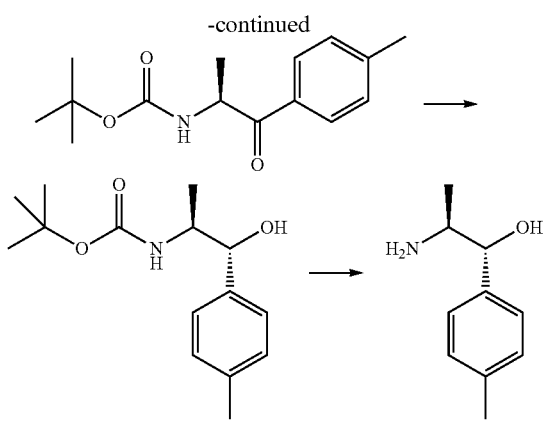

Preparation 1: (S)-tert-Butyl-(1-methoxy(methyl)amino)-1-oxopropan-2-yl)carbamate

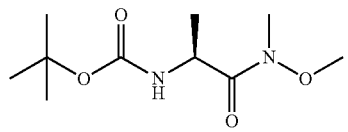 [SMILES: CON(C)C(=O)[C@H](C)NC(=O)OC(C)(C)C]

N-(3-dimethylaminopropyl)-N'-ethylcarboiimide hydrochloride (455 g, 2378.4 mmol), 1-hydroxybenzotriazole (214.3 g, 1585.6 mmol) and triethylamine (571.9 mL, 3964 mmol) were added to a stirred solution of (2S)-2-(tert-butoxycarbonylamino)propanoic acid (300 g, 1585.6 mmol) in dichloromethane (3 L) at 0° C., followed by N, O-dimethyl hydroxylamine hydrochloride (185.6 g, 1902.7 mmol). The reaction mixture was allowed to stir at room temperature for 16 h. On completion, the reaction mixture was concentrated under reduced pressure. Water (1 L) was added to the resulting crude and the mixture stirred for 0.5 hr, filtered and dried to afford the titled compound as a white solid (290 g, 78.8%).

TLC system: 30% ethyl acetate in petroleum ether, $R_f$: 0.2.

$^1$H NMR (400 MHz, CDCl$_3$) δ=5.25 (br d, J=6.1 Hz, 1H), 4.68 (br s, 1H), 3.77 (s, 3H), 3.21 (s, 3H), 1.44 (s, 9H), 1.31 (d, J=6.7 Hz, 3H).

Preparation 2: (S)-tert-Butyl(1-oxo-1-(p-tolyl)propan-2-yl)carbamate

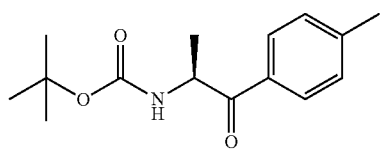 [SMILES: Cc1ccc(C(=O)[C@H](C)NC(=O)OC(C)(C)C)cc1]

4-Methylphenyl magnesium bromide (3 eq, 646 mmol) [freshly prepared from 4-bromotoluene (106 mL, 619.7 mmol) using magnesium turnings (22.3 g, 929 mmol), Iodine (cat) and 1,2-dibromoethane (0.5 mL) in tetrahydrofuran (1 L) at room temperature] was added slowly, over 1 h, to a stirred solution of the amide from Preparation 1 (50 g, 215.5 mmol) in tetrahydrofuran (1 L) at 0° C. After the addition, the reaction mixture was allowed to stir at room temperature for 16 h. On completion, the reaction mixture was cooled to 5° C. and quenched with saturated aqueous ammonium chloride solution (1 L) and extracted with ethyl acetate (2×1 L). The combined ethyl acetate layers were washed with water (1 L), brine (250 mL), dried over sodium sulphate and evaporated under reduced pressure. The obtained residue was purified by silica gel (100-200 mesh) column chromatography eluting with a gradient of ethyl acetate (3-10%) in petroleum ether to afford the titled compound as a white solid (31 g, 53%, white solid).

TLC system: 10% ethyl acetate in petroleum ether, $R_f$: 0.5.

$^1$H NMR (300 MHz, CDCl$_3$) δ=7.87 (d, J=8.1 Hz, 2H), 7.29 (d, J=8.1 Hz, 2H), 5.58 (br d, J=6.3 Hz, 1H), 5.27 (td, J=7.1, 14.3 Hz, 1H), 2.42 (s, 3H), 1.46 (s, 9H), 1.39 (d, J=7.1 Hz, 3H).

Preparation 3: tert-Butyl((1R,2S)-1-hydroxy-1-(p-tolyl)propan-2-yl)carbamate

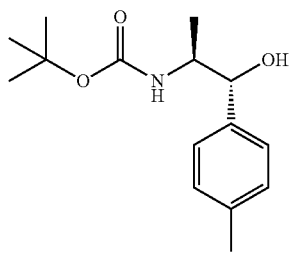 [SMILES: Cc1ccc([C@@H](O)[C@H](C)NC(=O)OC(C)(C)C)cc1]

Aluminium isopropoxide (32.9 g, 161.5 mmol) and isopropanol (255 mL) were added to a stirred solution of the ketone from Preparation 2 (85 g, 323.2 mmol) in toluene (425 mL) at room temperature. The reaction mixture was stirred at 60° C. for 16 h. On completion, the reaction mixture was cooled to 5° C. and quenched with aqueous 1N hydrochloric acid (300 mL) and extracted with ethyl acetate (2×500 mL). The combined ethyl acetate layers were washed with water (300 mL), brine (200 mL), dried over sodium sulphate and evaporated under reduced pressure. The obtained residue was triturated with 1 mixture (1:1) of n-pentane and diethyl ether (2×150 mL) and dried to afford the tilted compound as a white solid (80 g, 93.43%).

TLC system: 20% ethyl acetate in petroleum ether, $R_f$: 0.4

$^1$H NMR (300 MHz, CDCl$_3$) δ=7.25-7.20 (m, 2H), 7.19-7.11 (m, 2H), 4.82 (t, J=3.5 Hz, 1H), 4.60 (br s, 1H), 3.99 (br s, 1H), 3.10 (br s, 1H), 2.34 (s, 3H), 1.46 (s, 9H), 0.99 (d, J=7.0 Hz, 3H). HPLC purity: 97%

Preparation 4: (1R,2S)-2-Amino-1-(p-tolyl)propan-1-ol

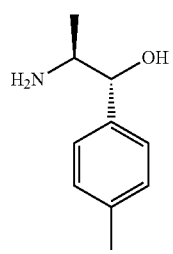

1,1,1-Trifluoroacetic acid (2 L, 18113 mmol) was slowly added to a stirred solution of the carbamate from Preparation 3 (80 g, 301.8 mmol) in dichloromethane (600 mL) and water (600 mL) at 0° C., over 1.5 h. The reaction mixture was warmed to room temperature and stirred for 4 h. The dichloromethane layer was separated and the aqueous 1,1,1-trifluoroacetic acid layer was concentrated to a small volume under reduced pressure. The resulting aqueous solution was then cooled in an ice bath before being made basic with 10% aqueous sodium hydroxide solution and extracted with dichloromethane (2×1 L). The combined dichloromethane layers were washed with brine (100 mL), dried over sodium sulphate and evaporated under reduced pressure to give the titled compound as white solid (40 g, 80.3%).

TLC system: 10% methanol in dichloromethane, $R_f$: 0.1

$^1$H NMR (400 MHz, DMSO-$d_6$) δ=7.20-7.16 (m, 2H), 7.13-7.09 (m, 2H), 5.05 (br s, 1H), 4.26 (d, J=4.9 Hz, 1H), 2.94-2.74 (m, 1H), 2.28 (s, 3H), 1.23 (br s, 2H), 0.84 (d, J=6.7 Hz, 3H)

Scheme 7.2

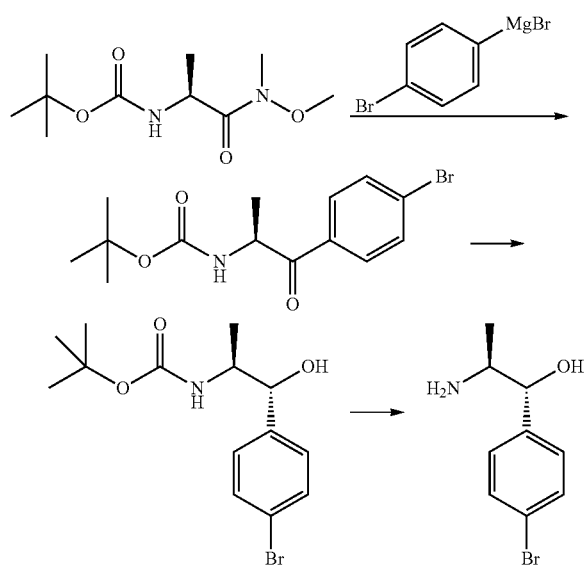

Preparation 5: (S)-tert-Butyl-(1-(4-bromophenyl)-1-oxopropan-2-yl)carbamate

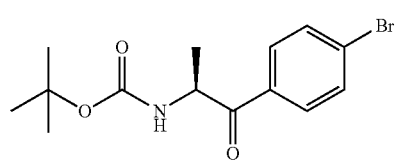 [SMILES: C[C@H](NC(=O)OC(C)(C)C)C(=O)c1ccc(Br)cc1]

Using a procedure similar to that described for Preparation 2, but using 4-bromophenyl magnesium bromide, the title compound was prepared as a white solid (30 g, 42.6%).

TLC system: 10% ethyl acetate in petroleum ether, $R_f$: 0.5

$^1$H NMR (400 MHz, CDCl$_3$) δ=7.84 (d, J=8.5 Hz, 2H), 7.64 (d, J=8.5 Hz, 2H), 5.48 (br d, J=6.7 Hz, 1H), 5.23 (br t, J=7.2 Hz, 1H), 1.45 (s, 9H), 1.38 (d, J=7.3 Hz, 3H).

Preparation 6: tert-Butyl-((1R,2S)-1-(4-bromophenyl)-1-hydroxypropan-2-yl)carbamate

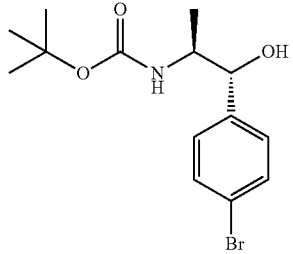 [SMILES: C[C@H](NC(=O)OC(C)(C)C)[C@H](O)c1ccc(Br)cc1]

Using a procedure similar to that described for Preparation 3, but using the compound from Preparation 5, the title compound was prepared as a white solid (78 g, 96.9%).

TLC system: 20% ethyl acetate in petroleum ether, $R_f$: 0.45

$^1$H NMR (400 MHz, CDCl$_3$) δ=7.53-7.40 (m, 2H), 7.22 (d, J=8.2 Hz, 2H), 4.81 (d, J=2.4 Hz, 1H), 4.55 (br s, 1H), 3.98 (br s, 1H), 3.42 (br s, 1H), 1.46 (s, 9H), 0.98 (d, J=7.0 Hz, 3H).

Preparation 7: (1R,2S)-2-amino-1-(4-bromophenyl)propan-1-ol

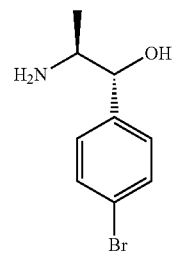

Using a procedure similar to that described for Preparation 4, but using the compound described in Preparation 6, the title compound was prepared as a white solid (20 g, 71.8%).

TLC system: 10% methanol in dichloromethane, $R_f$: 0.1

$^1$H NMR (400 MHz, DMSO-$d_6$) δ=7.52-7.47 (m, 2H), 7.26 (d, J=8.2 Hz, 2H), 5.25 (br s, 1H), 4.30 (d, J=4.9 Hz, 1H), 2.86 (m, 1H), 1.53-1.08 (m, 2H), 0.83 (d, J=6.7 Hz, 3H).

Preparation 8: tert-Butyl N-[(1S)-2-(4-ethylphenyl)-1-methyl-2-oxo-ethyl]carbamate

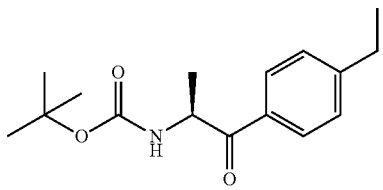 [SMILES: CCc1ccc(C(=O)[C@H](C)NC(=O)OC(C)(C)C)cc1]

Using a procedure similar to that described for Preparation 2, but using 4-ethylphenyl magnesium bromide, the title compound was prepared as a white solid (25 g, 69%).

TLC system: 20% ethyl acetate in petroleum ether, $R_f$=0.5

$^1$H NMR (300 MHz, CDCl$_3$) δ=7.90 (d, J=8.0 Hz, 2H), 7.31 (d, J=8.0 Hz, 2H), 5.58 (br d, J=6.9 Hz, 1H), 5.27 (br t, J=7.1 Hz, 1H), 2.72 (q, J=7.7 Hz, 2H), 1.46 (s, 9H), 1.40 (d, J=6.9 Hz, 3H), 1.26 (t, J=7.7 Hz, 3H). LCMS: 97.9%, Mass (M+H)=278.4.

Preparation 9: tert-Butyl N-[(1S,2R)-2-(4-ethylphenyl)-2-hydroxy-1-methyl-ethyl]carbamate

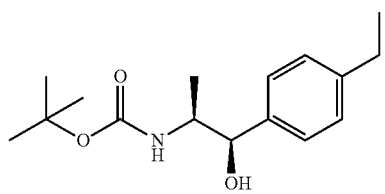 [SMILES: CCc1ccc([C@@H](O)[C@H](C)NC(=O)OC(C)(C)C)cc1]

Using a procedure similar to that described for Preparation 3, but using the compound from Preparation 8, the title compound was prepared as a white solid (20 g, 80.3%).

TLC system: 20% ethyl acetate in petroleum ether, $R_f$=0.4

$^1$H NMR (300 MHz, CDCl$_3$) δ=7.26-7.22 (m, 2H), 7.20-7.14 (m, 2H), 4.82 (t, J=3.4 Hz, 1H), 4.61 (br s, 1H), 3.99 (br s, 1H), 3.05 (br s, 1H), 2.64 (q, J=7.6 Hz, 2H), 1.46 (s, 9H), 1.23 (t, J=7.7 Hz, 3H), 1.00 (d, J=6.9 Hz, 3H), LCMS: 99.7%, Mass (M+H)=280.4.

Preparation 10: (1R,2S)-2-Amino-1-(4-ethylphenyl)propan-1-ol

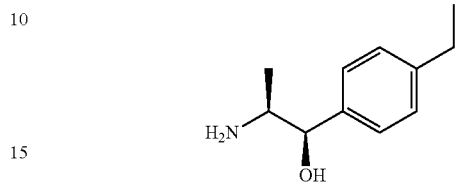

Using a procedure similar to that described for Preparation 4, but using the compound described in Preparation 9, the title compound was prepared as a white solid (23 g, 81.4%).

TLC system: 10% methanol in dichloromethane, $R_f$: 0.2.

$^1$H NMR (400 MHz, CDCl$_3$) δ=7.26-7.23 (m, 2H), 7.20-7.16 (m, 2H), 4.49 (d, J=4.9 Hz, 1H), 3.26-3.10 (m, 1H), 2.65 (q, J=7.4 Hz, 2H), 1.68-1.39 (m, 2H), 1.24 (t, J=7.6 Hz, 3H), 0.99 (d, J=6.4 Hz, 3H)

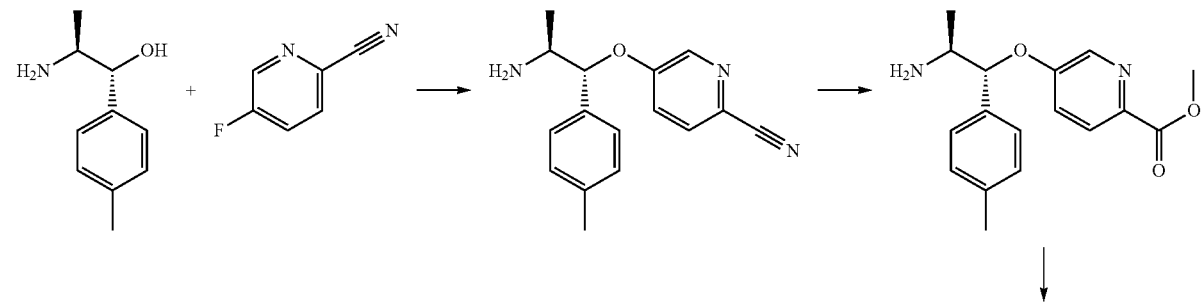

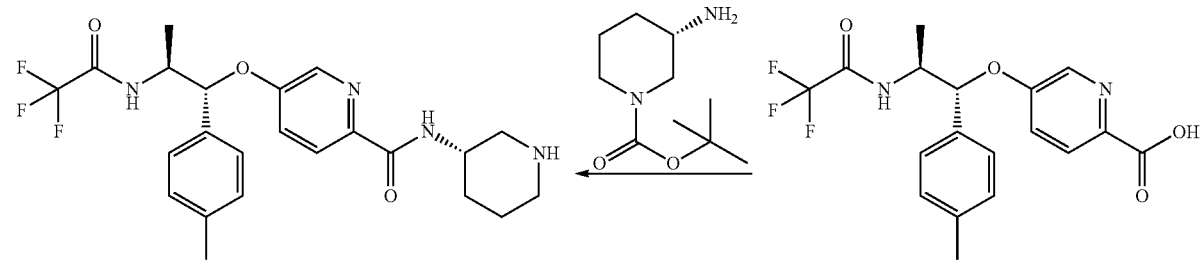

Preparation 11: 5-[(1R,2S)-2-Amino-1-(p-tolyl)propoxy]pyridin-2-carbonitrile

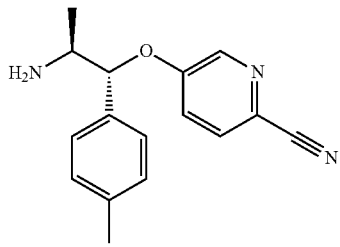 [SMILES: Cc1ccc([C@@H](Oc2ccc(C#N)nc2)[C@H](C)N)cc1]

Sodium hydride (60% wt/wt in mineral oil, 2.99 g, 74.6 mmol) was added in small portions to a solution of the amino alcohol from Preparation 4 (10 g, 57.4 mmol) in tetrahydrofuran (200 mL). The reaction was stirred at 50° C. for 1 hr before cooling to −25° C. 5-Fluoropyridine-2-carbonitrile (7.93 g, 64.9 mmol) was dissolved in tetrahydrofuran (100 mL) and added over 15 min to the cooled reaction mixture. The reaction mixture was allowed to warm to 0° C. and stirred for 3 hrs before being quenched by pouring on to ice cold saturated aqueous ammonium chloride (500 mL). The product was extracted with ethyl acetate (4×250 ml). The combined organics were dried over magnesium sulphate, filtered and evaporated under reduced pressure. The obtained residue was purified by silica gel (100-200 mesh) column chromatography eluting with 2:1 mixture of ethyl acetate:heptane until high running impurities are eluted followed by 90:10:1 ethyl acetate:methanol:0.880 aqueous ammonia. Clean fractions were evaporated under reduced pressure to give the title compound as an oil (10.04 g, 65%).

$^1$H NMR (300 MHz, CDCl$_3$) δ 8.35 (dd, J=2.9, 0.6 Hz, 1H), 7.47 (dd, J=8.6, 0.6 Hz, 1H), 7.25-7.14 (m, 4H), 7.09 (dd, J=8.7, 2.9 Hz, 1H), 4.93 (d, J=5.4 Hz, 1H), 3.38 (qd, J=6.5, 5.3 Hz, 1H), 2.33 (s, 3H), 1.19 (d, J=6.5 Hz, 3H).

Preparation 12: Methyl 5-[(1R,2S)-2-amino-1-(p-tolyl)propoxy]pyridine-2-carboxylate

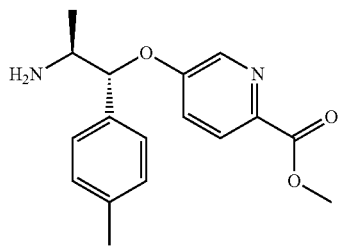 [SMILES: COC(=O)c1ccc(O[C@H](c2ccc(C)cc2)[C@H](C)N)cn1]

Sodium hydroxide (32% wt in water, 27 g, 216 mmol) was added to a solution of the nitrile from Preparation 11 (10.0 g, 37.4 mmol) in ethanol (100 mL) and the resulting mixture heated to 85° C. for 2 hr. The solvent was removed by evaporation under reduced pressure followed by azeotropic distillation with toluene (3×150 mL). The resulting solid was suspended in methanol (300 mL) and 98% conc. sulphuric acid (12 mL, 224 mmol) was added over 0.05 hr. The reaction mixture was heated to 85° C. for 18 hr. The mixture was cooled and concentrated, by evaporating under reduced pressure, to a small volume. The resulting residue was poured on to a mixture of ice cold saturated sodium hydrogen carbonate (300 mL) and ethyl acetate (300 mL). The aqueous layer was extracted three more times with ethyl acetate (3×200 mL). The combined ethyl acetate layers were dried over magnesium sulphate, filtered and evaporated to give the title compound as an oil (8.82 g, 78%).

$^1$H NMR (300 MHz, CDCl$_3$) δ=8.37 (dt, J=2.9, 0.6, 1H), 7.94 (dt, J=8.7, 0.6, 1H), 7.22-7.09 (m, 5H), 5.01 (d, J=5.2, 1H), 3.92 (d, J=0.6, 3H), 3.46-3.31 (m, 1H), 2.32 (s, 3H), 1.20 (dd, J=6.6, 0.6, 3H).

Preparation 13: Methyl 5-[(1R,2S)-1-(p-tolyl)-2-[(2,2,2-trifluoroacetyl)amino]propoxy]pyridine-2-carboxylate

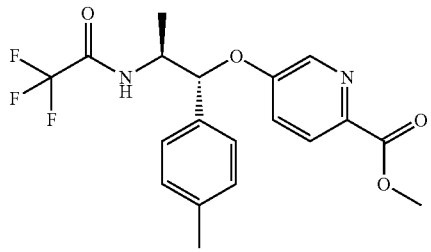 [SMILES: COC(=O)c1ccc(O[C@H](c2ccc(C)cc2)[C@H](C)NC(=O)C(F)(F)F)cn1]

Trifluoroacetic anhydride (4.5 mL, 32 mmol) was added to a solution of the amino ester form Preparation 12 (7.4 g, 25 mmol) and triethylamine dissolved in dichloromethane (74 mL). The mixture was stirred at room temperature for 0.5 hr. The reaction was quenched by adding saturated aqueous sodium hydrogen carbonate (75 mL) and extracted with dichloromethane (3×75 mL). The combined dichloromethane layers were dried over magnesium sulphate, filtered and evaporated. The obtained residue was purified by silica gel (100-200 mesh) column chromatography eluting with a gradient of ethyl acetate (25-100%) in heptane to give the title compound as an oil (7.90 g, 81%).

$^1$H NMR (300 MHz, DMSO-d$_6$) δ=9.50 (d, J=8.4, 1H), 8.35 (d, J=3.0, 1H), 7.92 (d, J=8.7, 1H), 7.33 (dd, J=8.8, 2.9, 1H), 7.25 (d, J=8.1, 2H), 7.16 (d, J=8.0, 2H), 5.43 (d, J=6.0, 1H), 4.25 (dt, J=14.1, 6.9, 1H), 3.80 (s, 3H), 2.26 (s, 3H), 1.29 (d, J=6.8, 3H).

Preparation 14: 5-[(1R,2S)-1-(p-Tolyl)-2-[(2,2,2-trifluoroacetyl)amino]propoxy]pyridine-2-carboxylic acid

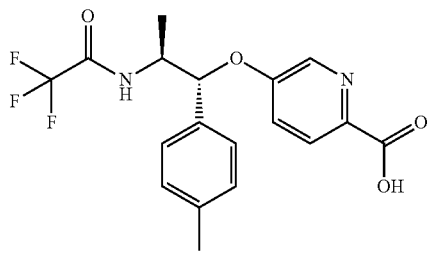 [SMILES: Cc1ccc([C@@H](Oc2ccc(C(=O)O)nc2)[C@H](C)NC(=O)C(F)(F)F)cc1]

Sodium hydroxide (0.866 g, 21.6 mmol) was dissolved in water (19.7 mL) and added to a solution of the ester of Preparation 13 (7.8 g, 19.7 mmol) dissolved in methanol (80 mL). The mixture was stirred at 50° C. for 8 hr. The methanol was removed by evaporation under reduced pressure and the residue was freeze-dried. The dried residue was dissolved in a small amount of methanol (10 mL) and water (40 mL) added. The mixture was made slightly acidic with 4 M aqueous hydrochloric acid (pH=4) and extracted with ethyl acetate (3×150 mL). The combined ethyl acetate layers were dried over magnesium sulphate, filtered and evaporated to give the title compound as a pink solid (6.71 g, 89.2%).

$^1$H NMR (300 MHz, CDCl$_3$) δ=8.22 (dd, J=2.8, 0.6, 1H), 8.04 (dd, J=8.7, 0.7, 1H), 7.23-7.16 (m, 5H), 6.44 (d, J=8.8, 1H), 5.43 (d, J=3.2, 1H), 4.50 (s, 1H), 2.35 (s, 3H), 1.29 (d, J=6.8, 3H).

Preparation 15: tert-butyl (3S)-3-[[5-[(1R,2S)-1-(p-tolyl)-2-[(2,2,2-trifluoroacetyl)amino]propoxy]pyridine-2-carbonyl]amino]piperidine-1-carboxylate

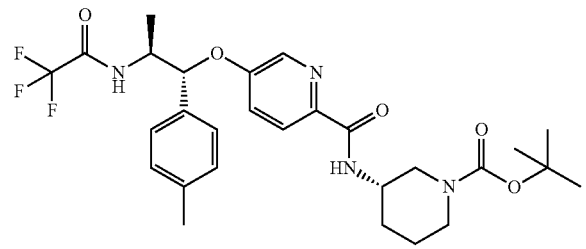

O-(7-Azabenzotriazol-1-yl)-N, N, N',N'-tetramethyluronium hexafluorophosphate (8.53 g, 22.4 mmol) was added to a solution of the acid of Preparation 14 (5.72 g, 15.0 mmol), tert-butyl (3S)-3-aminopiperidine-1-carboxylate (4.49 g, 22.4 mmol) and triethylamine (6.06 g, 60 mmol) in N,N-dimethylformamide (150 mL). The reaction was stirred over night at room temperature. The mixture was evaporated under reduced pressure and resulting residue dissolved in diethyl ether (500 mL). This diethyl ether solution was washed with 10% aqueous citric acid solution (3×50 mL) followed by 10% aqueous ammonia, saturated brine solution and dried over magnesium sulphate, filtered and evaporated. The residue was purified by silica gel (100-200 mesh) column chromatography eluting with 50% ethyl acetate in heptane to give the title compound as an amorphous solid (7.2 g, 86%).

$^1$H NMR (300 MHz, DMSO-d$_6$) δ=9.47 (d, J=8.4, 1H), 8.27 (d, J=8.1, 1H), 8.21 (dd, J=2.9, 0.6, 1H), 7.89 (dd, J=8.7, 0.6, 1H), 7.39 (dd, J=8.8, 2.9, 1H), 7.25 (d, J=8.2, 2H), 7.15 (d, J=7.8, 2H), 5.41 (d, J=6.1, 1H), 4.27 (h, J=6.8, 1H), 3.55 (s, 3H), 2.97 (s, 2H), 2.26 (s, 3H), 1.77 (s, 1H), 1.62 (s, 2H), 1.50-1.24 (m, 13H).

UPLC-MS Method 2: Mass ion 564.26 (M$^+$), R$_t$=2.63 min.

Preparation 16: N-[(3S)-3-piperidyl]-5-[(1R,2S)-1-(p-tolyl)-2-[(2,2,2-trifluoroacetyl)amino]propoxy]pyridine-2-carboxamide

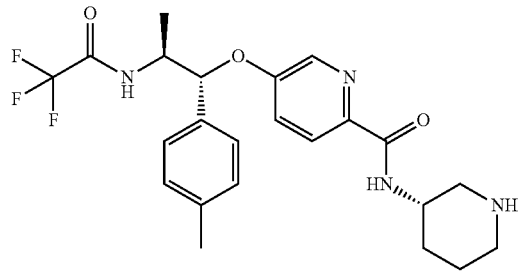 [SMILES: Cc1ccc([C@@H](Oc2ccc(C(=O)N[C@H]3CCCNC3)nc2)[C@H](C)NC(=O)C(F)(F)F)cc1]

Trifluoroacetic acid (50 mL, 653 mmol) was added to a solution of the carbamate of Preparation 15 (7.2 g, 12.8 mmol) dissolved in dichloromethane (100 mL). The reaction was stirred at room temperature for 20 min. The reaction mixture was evaporated, partitioned between diethyl ether and 10% aqueous ammonia solution. The diethyl ether layer was washed with 10% aqueous citric acid (5×100 mL) then combined citric layers back washed with a small volume of diethyl ether (50 mL). The combined aqueous citric layers were then made basic with ammonia and extracted with diethyl ether (3×200 mL). These diethyl ether layers were combined and washed with a small volume of brine, then dried over magnesium sulphate, filtered and evaporated to give the title compound as an off white foam (5.86 g, 99%).

$^1$H NMR (300 MHz, CDCl$_3$) δ=8.15 (dd, J=2.9, 0.6, 1H), 8.09-7.95 (m, 2H), 7.21-7.11 (m, 5H), 6.61 (d, J=8.8, 1H), 5.37 (d, J=3.3, 1H), 4.47 (s, 1H), 4.03 (tq, J=7.5, 3.7, 1H), 3.11 (dd, J=11.9, 3.4, 1H), 2.86 (m, 1H), 2.81-2.60 (m, 2H), 2.33 (s, 3H), 1.89 (td, J=7.6, 3.7, 1H), 1.73 (m, 1H), 1.60-1.48 (m, 2H), 1.27 (d, J=6.9, 3H).

UPLC-MS Method 2: Mass ion 464.2 (M$^+$), R$_t$=2.02 min.

Preparation 17: N-[(3R)-3-piperidyl]-5-[(1R,2S)-1-(p-tolyl)-2-[(2,2,2-trifluoroacetyl)amino]propoxy]pyridine-2-carboxamide

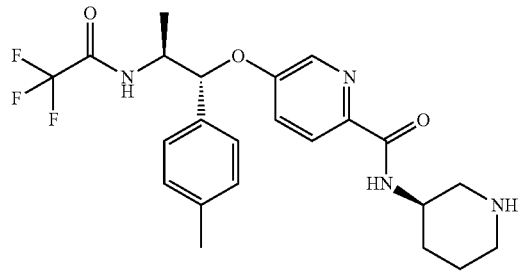 [SMILES: Cc1ccc([C@@H](Oc2ccc(C(=O)N[C@@H]3CCCNC3)nc2)[C@H](C)NC(=O)C(F)(F)F)cc1]

Using a procedure similar to that described for Preparation 15, but using (3R)-3-aminopiperidine-1-carboxylate, followed by a procedure similar to that described in Preparation 16, the title compound was prepared as a white foam (0.156 g, 64%). 1H NMR (300 MHz, DMSO-d$_6$) δ=9.49 (d, J=8.4, 1H), 8.38 (d, J=8.6, 1H), 8.24 (d, J=2.8, 1H), 7.88 (d, J=8.7, 1H), 7.38 (dd, J=8.7, 2.9, 1H), 7.25 (d, J=8.0, 2H), 7.15 (d, J=7.9, 2H), 5.40 (d, J=6.2, 1H), 4.27 (q, J=7.1, 1H), 3.99-3.81 (m, 1H), 2.95 (dd, J=11.8, 3.7, 1H), 2.88-2.77 (m, 1H), 2.61 (dd, J=11.6, 8.4, 2H), 2.26 (s, 3H), 1.78-1.40 (m, 4H), 1.30 (d, J=6.8, 3H).

UPLC-MS Method 2: Mass ion 464.2 (M$^+$), R$_t$=2.01 min.

Preparation 18: 5-[(1R,2S)-2-Amino-1-(4-ethylphenyl)propoxy]pyridine-2-carbonitrile

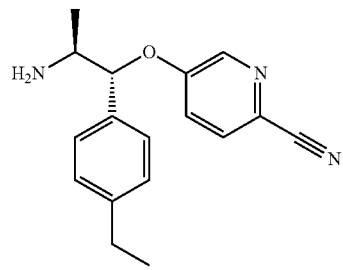 [SMILES: CCc1ccc([C@@H](Oc2ccc(C#N)nc2)[C@H](C)N)cc1]

Using a procedure similar to that described for Preparation 11, but using the amino alcohol described in Preparation 10, the title compound was prepared as a brown oil (0.55 g, 70%).

1H NMR (300 MHz, CDCl$_3$) δ=8.35 (dd, J=2.9, 0.6, 1H), 7.48 (dd, J=8.6, 0.6, 1H), 7.20 (m, 4H), 7.09 (dd, J=8.7, 2.9, 1H), 4.93 (d, J=5.4, 1H), 3.45-3.24 (m, 1H), 2.63 (q, J=7.6, 2H), 1.25-1.18 (m, 6H).

Preparation 19: methyl 5-[(1R,2S)-2-Amino-1-(4-ethylphenyl)propoxy]pyridine-2-carboxylate

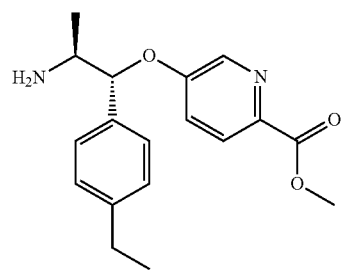 [SMILES: CCc1ccc([C@@H](Oc2ccc(C(=O)OC)nc2)[C@H](C)N)cc1]

Using a procedure similar to that described for Preparation 12, but using the compound described in Preparation 18, the title compound was prepared as a brown oil (0.48 g, 79%).

1H NMR (300 MHz, CDCl$_3$) δ=8.37 (d, J=2.7, 1H), 7.95 (dd, J=8.7, 0.6, 1H), 7.25-7.11 (m, 5H), 5.01 (d, J=5.2, 1H), 3.93 (s, 3H), 3.48-3.24 (m, 1H), 2.62 (q, J=7.6, 2H), 1.24-1.17 (m, 6H).

Preparation 20: 5-[(1R,2S)-1-(4-Ethylphenyl)-2-[(2,2,2-trifluoroacetyl)amino]propoxy]pyridine-2-carboxylic acid

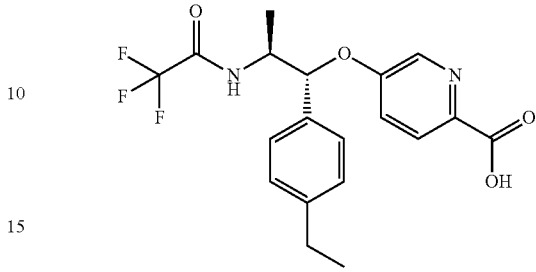

Using a procedure similar to that described for Preparation 13, but using the compound described in Preparation 19, followed by a procedure similar to that used in Preparation 14 the title compound was prepared as an oil (0.089 g, 71%).

$^1$H NMR (300 MHz, DMSO-d$_6$) δ=9.50 (d, J=8.4, 1H), 8.33 (d, J=2.9, 1H), 7.91 (d, J=8.8, 1H), 7.33 (dd, J=8.8, 2.9, 1H), 7.30-7.17 (m, 4H), 5.44 (d, J=5.9, 1H), 4.46-4.09 (m, 1H), 2.56 (q, J=7.6, 2H), 1.29 (d, J=6.8, 3H), 1.14 (t, J=7.6, 3H).

Preparation 21: 5-[(1R,2S)-1-(4-ethylphenyl)-2-[(2,2,2-trifluoroacetyl)amino]propoxy]-N-[(3S)-3-piperidyl]pyridine-2-carboxamide

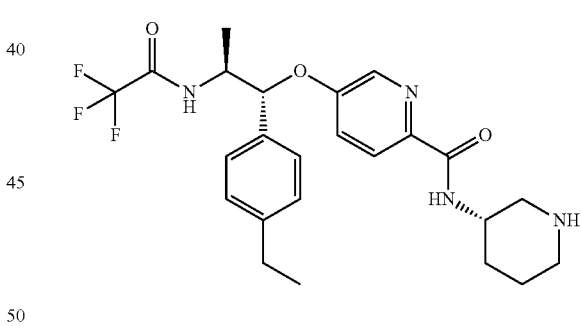

Using a procedure similar to that described for Preparation 15, but using the compound from Preparation 20, followed by a procedure similar to that described in Preparation 16, the title compound was prepared as an oil (0.066 g, 54%).

$^1$H NMR (300 MHz, CDCl$_3$) δ=8.35-8.22 (m, 2H), 8.18 (d, J=2.7, 1H), 7.94 (d, J=8.7, 1H), 7.20 (s, 4H), 7.09 (dd, J=8.7, 2.8, 1H), 6.67 (d, J=8.7, 1H), 5.39 (d, J=3.2, 1H), 4.60-4.42 (m, 1H), 4.37-4.14 (m, 1H), 3.31 (dd, J=12.9, 3.9, 1H), 3.19-2.94 (m, 3H), 2.63 (q, J=8.0, 2H), 2.09-1.91 (m, 2H), 1.89-1.63 (m, 2H), 1.28 (d, J=6.9, 3H), 1.22 (t, J=7.6, 3H).

45
46
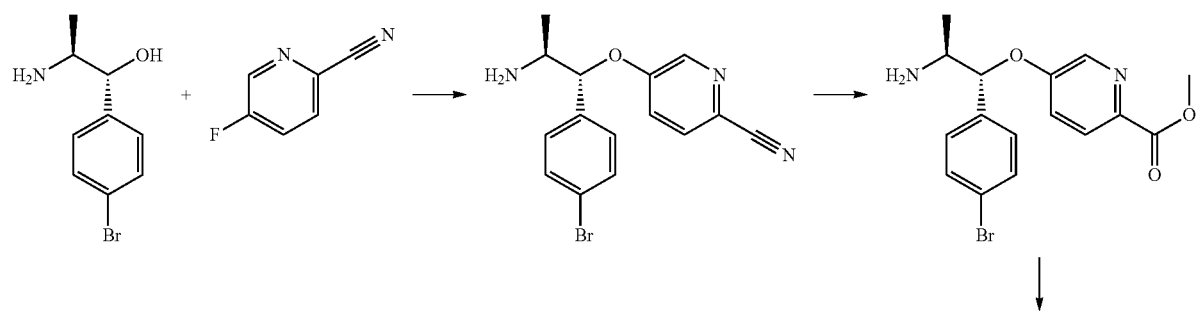
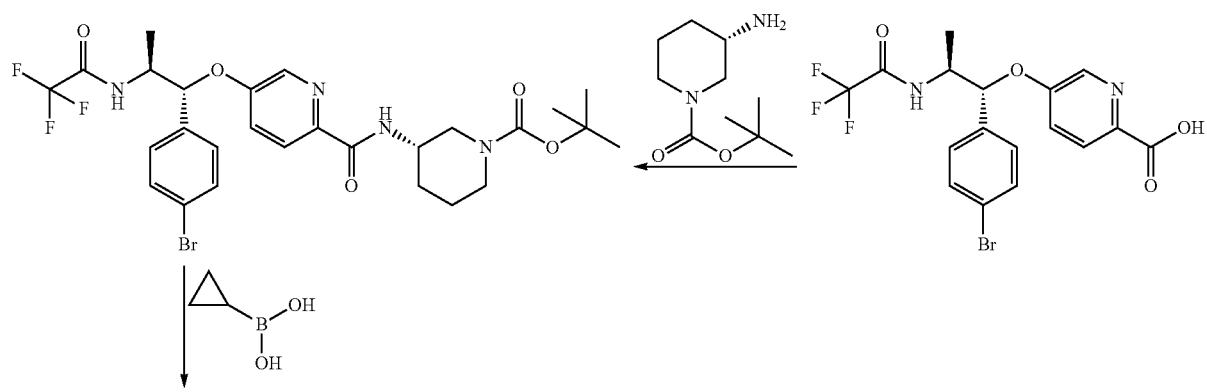
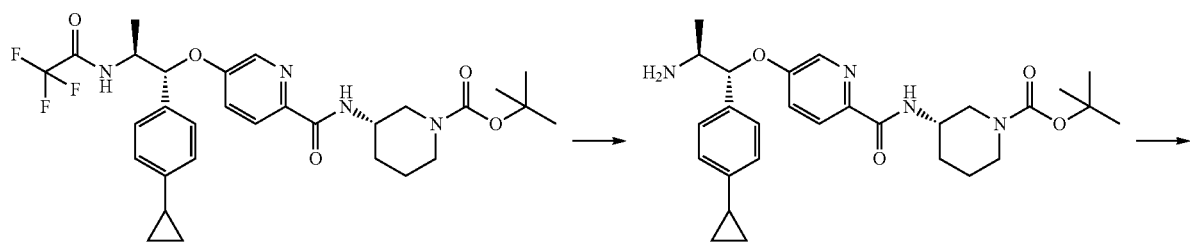
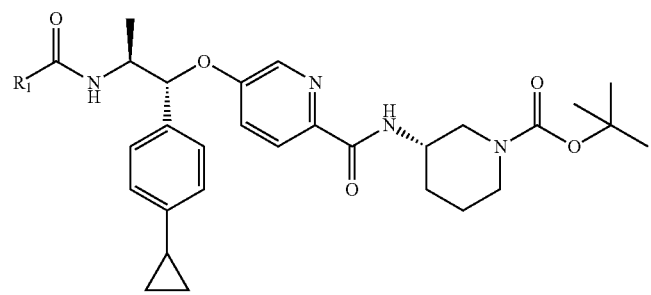

Preparation 22: 5-[(1R,2S)-2-Amino-1-(4-bromophenyl)propoxy]pyridine-2-carbonitrile

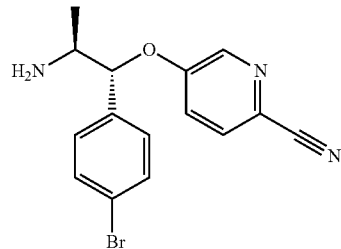 [SMILES: C[C@H](N)[C@H](Oc1ccc(C#N)nc1)c1ccc(Br)cc1]

Using a procedure similar to that described for Preparation 11, but using the amino alcohol described in Preparation 7, the title compound was prepared as an oil (2 g, 85%).

$^1$H NMR (300 MHz, DMSO-d$_6$) δ=8.44 (dd, J=3.0, 0.7, 1H), 7.89 (dd, J=8.7, 0.6, 1H), 7.61-7.52 (m, 2H), 7.42 (dd, 1=8.7, 2.9, 1H), 7.38-7.33 (m, 2H), 5.34 (d, 1=5.1, 1H), 3.28-3.20 (m, 1H), 1.03 (d, J=6.5, 3H).

Preparation 23: methyl 5-[(1R,2S)-1-(4-bromophenyl)-2-[(2,2,2-trifluoroacetyl)amino]propoxy]pyridine-2-carboxylate

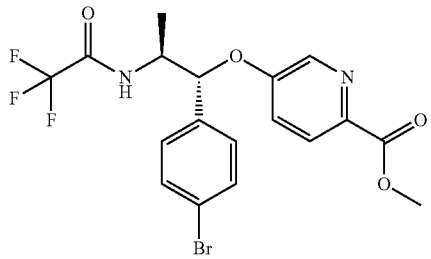 [SMILES: COC(=O)c1ccc(O[C@H](c2ccc(Br)cc2)[C@H](C)NC(=O)C(F)(F)F)cn1]

Using a procedure similar to that described for Preparation 12, but using the compound described in Preparation 22, followed by a procedure similar to that described in Preparation 13, the title compound was prepared as an amorphous solid (1.73 g, 62.3%).

$^1$H NMR (300 MHz, DMSO-d$_6$) δ=9.51 (d, J=8.5, 1H), 8.38 (dd, J=3.0, 0.6, 1H), 7.94 (dd, J=8.8, 0.6, 1H), 7.67-7.51 (m, 2H), 7.44-7.27 (m, 3H), 5.48 (d, J=6.0, 1H), 4.30 (h, J=6.7, 1H), 3.81 (s, 3H), 1.30 (d, J=6.8, 3H).

Preparation 24: tert-butyl (3S)-3-[[5-[(1R,2S)-1-(4-bromophenyl)-2-[(2,2,2-trifluoroacetyl)amino]propoxy]pyridine-2-carbonyl]amino]piperidine-1-carboxylate

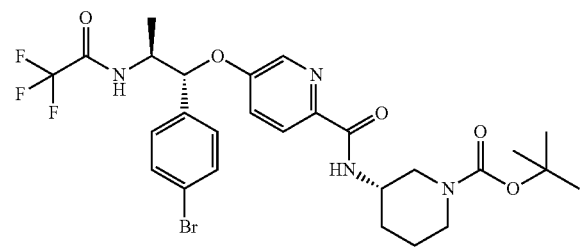 [SMILES: C[C@H](NC(=O)C(F)(F)F)[C@H](Oc1ccc(C(=O)N[C@H]2CCCN(C(=O)OC(C)(C)C)C2)nc1)c1ccc(Br)cc1]

Using a procedure similar to that described for Preparation 14, but using the compound described in Preparation 23 and using 2M aqueous sodium hydroxide (2.5 equiv.) in N,N-dimethylformamide (10 mL/g) to obtain the intermediate acid, 5-[(1R,2S)-1-(4-bromophenyl)-2-[(2,2,2-trifluoroacetyl)amino]propoxy]pyridine-2-carboxylic acid, followed by a procedure similar to that described in Preparation 15 but using O-(benzotriazol-1-yl)-N, N, N',N'-tetramethyluronium hexafluorophosphate instead of O-(7-Azabenzotriazol-1-yl)-N, N, N',N'-tetramethyluronium hexafluorophosphate, the title compound was prepared as an off white amorphous solid (1.08 g, 54%).

$^1$H NMR (300 MHz, DMSO-d$_6$) δ=9.50 (d, J=8.4, 1H), 8.29 (d, J=8.1, 1H), 8.23 (d, J=2.8, 1H), 7.91 (d, J=8.7, 1H), 7.56 (d, 2H), 7.42 (dd, J=8.7, 2.9, 1H), 7.33 (d, 2H), 5.45 (d, J=6.2, 1H), 4.30 (h, J=6.8, 1H), 3.91-3.39 (m, 3H), 3.27-2.71 (m, 2H), 1.78 (s, 1H), 1.72-1.56 (m, 2H), 1.51-1.29 (m, 13H).

Preparation 25: tert-butyl (3S)-3-[[5-[(1R,2S)-1-(4-cyclopropylphenyl)-2-[(2,2,2-trifluoroacetyl)amino]propoxy]pyridine-2-carbonyl]amino]piperidine-1-carboxylate

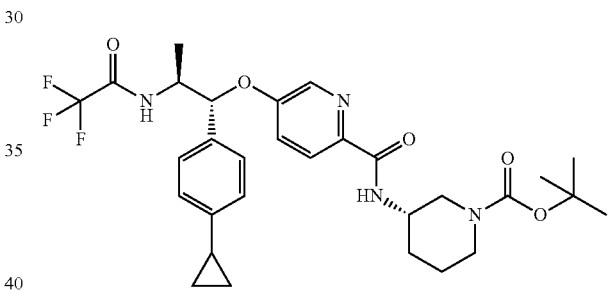

Palladium (II) acetate (0.015 g, 0.06910 mmol) was added to a solution of the bromide from Preparation 24 (0.87 g, 1.382 mmol), cyclopropyl boronic acid (0.154 g, 1.797 mmol), tricyclohexylphosphine (0.038 g, 0.1382 mmol), and potassium phosphate (1.03 g, 4.837 mmol) in toluene:water 20:1 (5.5 mL). After flushing the vial with argon it was sealed and reaction heated at 100° C. for 2 hr. The reaction was allowed to cool and diluted with ethyl acetate (50 mL) and washed with 10% aqueous citric acid solution (2×20 mL). The ethyl acetate layer was dried over magnesium sulphate, filtered and evaporated under reduced pressure. The residue was purified by silica gel (100-200 mesh) column chromatography eluting with a gradient of ethyl acetate in heptane (50% to 100%) to give the title compound as an off white foam (0.762 g, 93%).

$^1$H NMR (600 MHz, DMSO-d$_6$) δ=9.55 (d, J=8.3, 1H), 8.48-8.26 (m, 1H), 8.21 (d, J=2.8, 1H), 7.89 (d, J=8.7, 1H), 7.39 (dd, J=8.7, 2.8, 1H), 7.22 (d, 2H), 7.04 (d, 2H), 5.41 (d, J=6.0, 1H), 4.25 (dt, J=8.3, 6.4, 1H), 3.94-3.43 (m, 3H), 3.23-2.69 (m, 2H), 1.86 (tt, J=8.4, 5.1, 1H), 1.80-1.72 (m, 1H), 1.72-1.55 (m, 2H), 1.53-1.16 (m, 13H), 0.97-0.87 (m, 2H), 0.69-0.54 (m, 2H).

Preparation 26: tert-butyl (3S)-3-[[5-[(1R,2S)-2-amino-1-(4-cyclopropylphenyl)propoxy]pyridine-2-carbonyl]amino]piperidine-1-carboxylate

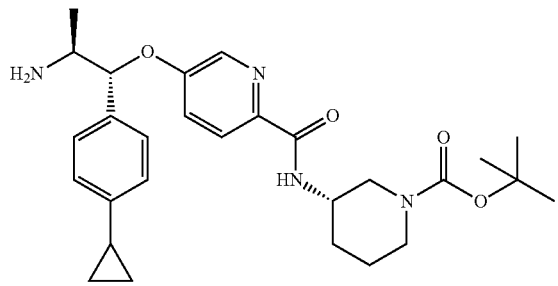 [SMILES: C[C@H](N)[C@H](Oc1ccc(C(=O)N[C@H]2CCCN(C(=O)OC(C)(C)C)C2)nc1)c1ccc(C2CC2)cc1]

Aqueous lithium hydroxide solution (1M, 54 mL, 54 mmol) was added to a solution of the compound from Preparation 25 (3.2 g, 5.4 mmol) in 1,4-dioxan (250 mL). The reaction mixture was heated to 50° C. for 2 hr. Upon completion the mixture was cooled and evaporated under reduced pressure to remove 1,4-dioxan. The residue was extracted with dichloromethane (4×150 mL) and combined organics dried over magnesium sulphate, filtered and evaporated under reduced pressure to give the title compound as a white foam (2.7 g, 100%).

UPLC-MS Method 1: Mass ion 495 (MH+), $R_t$=0.67 min

Preparation 27: tert-butyl (3S)-3-[[5-[(1R,2S)-1-(4-cyclopropylphenyl)-2-[[(2R)-tetrahydrofuran-2-carbonyl]amino]propoxy]pyridine-2-carbonyl]amino]piperidine-1-carboxylate

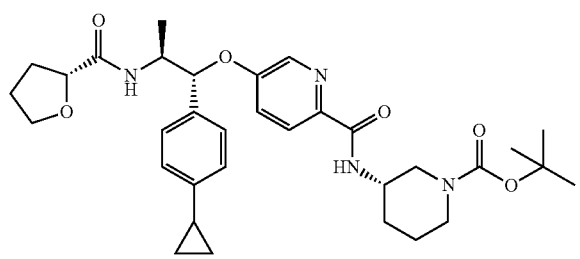 [SMILES: C[C@H](NC(=O)[C@H]1CCCO1)[C@H](Oc1ccc(C(=O)N[C@H]2CCCN(C(=O)OC(C)(C)C)C2)nc1)c1ccc(C2CC2)cc1]

Oxalyl chloride (4.2 mL, 50 mmol) was added to a solution of (2R)-tetrahydrofuran-2-carboxylic acid (0.580 g, 5 mmol) in dichloromethane (20 mL) followed by catalytic DMF (0.02 mL). The reaction mixture was stirred at room temperature for 1 hr and then evaporated under reduced pressure to give a yellow gum. This gum was dissolved in toluene (20 mL) and evaporated under reduced pressure, process repeated to remove the excess oxalyl chloride. The resulting (2R)-tetrahydrofuran-2-carboxylic acid chloride was added to a solution of the amine from Preparation 26 (1.3 g, 2.7 mmol) and 4-methylmorpholine (1.5 mL, 14 mmol) in dichloromethane (30 mL) at 5° C. The reaction was stirred at 5° C. for 0.5 hr and then evaporated under reduced pressure. The residue was partitioned between tert-butylmethyl ether (200 mL) and 5% aqueous citric acid solution (2×50 mL). The combined aqueous layers were back extracted with tert-butylmethyl ether (2×50 mL) and the ether layers combined and washed with 5% aqueous ammonia solution (2×50 mL), saturated brine (30 mL) and dried over magnesium sulphate, filtered and evaporated to give a brown foam. This brown foam was purified by column chromatography on silica (120 g) eluting with a gradient of ethyl acetate in heptane (0% to 100%) to give the title compound as an amorphous solid (1.24 g, 77%).

UPLC-MS Method 1: Mass ion 593 (MH+), $R_t$=0.88 min

Preparation 28: tert-butyl (3S)-3-[[5-[(1R,2S)-1-(4-cyclopropylphenyl)-2-(isoxazole-3-carbonylamino)propoxy]pyridine-2-carbonyl]amino]piperidine-1-carboxylate

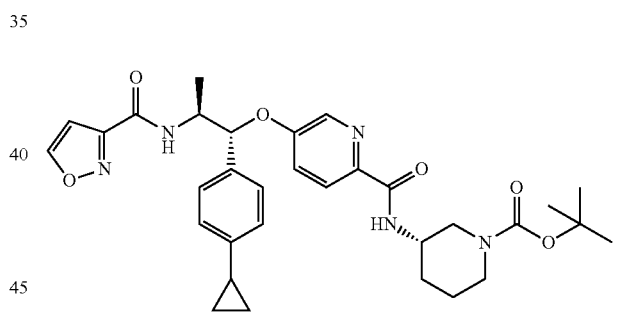

Using a procedure similar to that described for Preparation 27, but using isoxazole-3-carboxylic acid instead of (2R)-tetrahydrofuran-2-carboxylic acid, the title compound was prepared as an amorphous solid (1.46 g, 90%).

UPLC-MS Method 1: Mass ion 590 (MH+), Rt=0.90 min

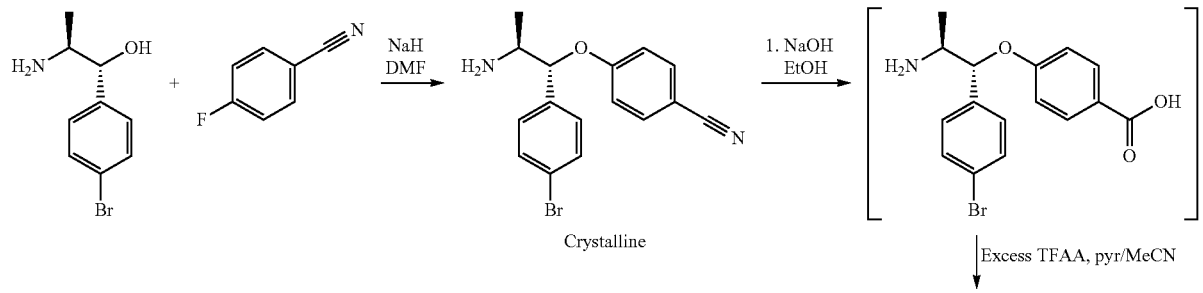

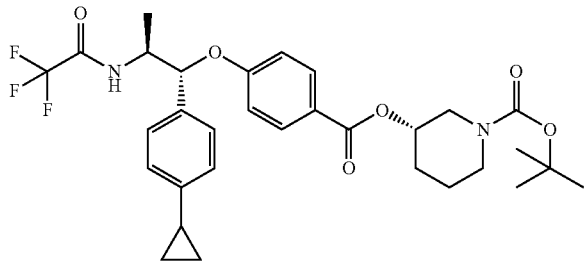

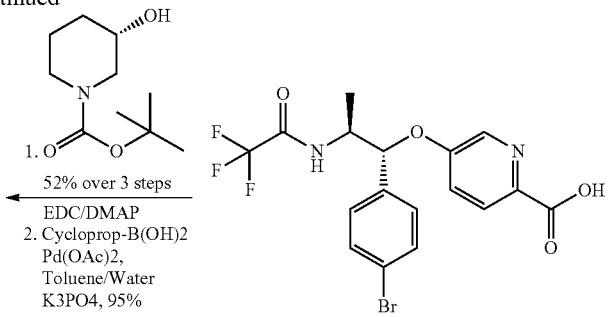

Preparation 29: 4-[(1R,2S)-2-amino-1-(4-bromophenyl)propoxy]benzonitrile hydrochloride

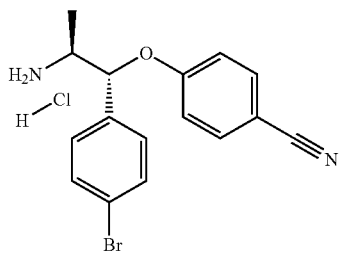

Sodium hydride (60% wt/wt in mineral oil, 2.9 g, 73 mmol) was added in small portions to a solution of the amino alcohol from Preparation 7 (15.3 g, 66.5 mmol) in N-methylpyrrolidin-2-one (46 mL). The reaction was stirred at 60° C. for 0.5 hr before adding 4-fluorobenzonitrile (9.66 g, 79.8 mmol) and heating for a further 0.5 hr. The reaction mixture was evaporated under reduced pressure (3.2 mbar) at 70° C. The residue was diluted with ethyl acetate (200 mL) and washed with 10% aqueous citric acid solution (50 mL) followed by saturated aqueous sodium hydrogen carbonate solution (2×25 mL). The ethyl acetate layer was dried over magnesium sulphate, filtered and the filtrate treated with 1M ethereal hydrogen chloride. The resulting mixture was evaporated under reduced pressure to give an off white solid. This solid was triturated with a small volume of cold ethyl acetate to give the title compound as a white solid (19.8 g, 81%).

$^1$H NMR (300 MHz, DMSO-$d_6$) δ=8.52 (s, 3H), 7.74 (d, 2H), 7.62 (d, 2H), 7.34 (d, 2H), 7.06 (d, 2H), 5.86 (d, J=3.1, 1H), 3.91-3.47 (m, 1H), 1.18 (d, J=7.1, 3H).

Preparation 30: tert-butyl (3S)-3-[4-[(1R,2S)-1-(4-bromophenyl)-2-[(2,2,2-trifluoroacetyl)amino]propoxy]benzoyl]oxypiperidine-1-carboxylate

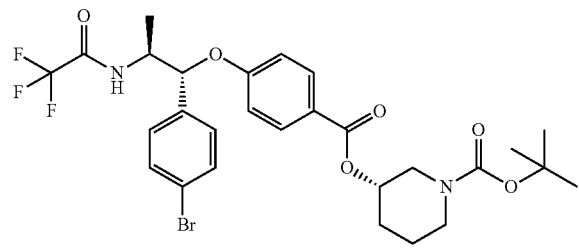 [SMILES: C[C@H](NC(=O)C(F)(F)F)[C@H](Oc1ccc(C(=O)O[C@H]2CCCN(C(=O)OC(C)(C)C)C2)cc1)c1ccc(Br)cc1]

Aqueous sodium hydroxide solution (32% wt/wt, 8.6 mL, 93 mmol) was added to a solution of the compound from Preparation 29 (6.85 g, 18.6 mmol) dissolved in ethanol (44 mL). The resulting solution was heated to 85° C. for 20 hr and then cooled and evaporated under reduced pressure. The residue was quenched with 4M aqueous hydrochloric acid (25 mL). The resulting mixture was evaporated under reduced pressure and the residue suspended in toluene (3×100 mL) and evaporated under reduced pressure to give the intermediate amino acid hydrochloride salt. This salt was suspended in a mixture of acetonitrile (75 mL) and pyridine (75 mL) and then cooled before adding trifluororoacetic anhydride (10 mL). The mixture was stirred at room temperature for 1 hr before evaporating under reduced pressure. The resulting residue was partitioned between dichloromethane (250 mL) and 10% aqueous citric acid solution (3×50 mL). The dichloromethane layer was then washed with saturated aqueous sodium hydrogen carbonate solution (25 mL) before drying over magnesium sulphate, filtering. The filtrate was evaporated under reduced pressure to give the intermediate trifluoroacetamide, 4-[(1R,2S)-1-(4-bromophenyl)-2-[(2,2,2-trifluoroacetyl)amino]propoxy]benzoic acid, as a brown oil (8.3 g). This oil was dissolved in dichloromethane (300 mL) before adding 1-ethyl-3-(3-dimethylaminopropyl) carbodiimide hydrochloride (7.14 g, 37.2 mmol), N,N-dimethylaminopyridine (6.8 g, 55.8 mmol) and tert-butyl (3S)-3-hydroxypiperidine-1-carboxylate (4.12 g, 20.5 mmol). The resulting mixture was stirred at room temperature for 5 hr before washing with 10% aqueous citric acid solution (2×50 mL), saturated sodium hydrogen carbonate (2×25 mL) and drying over magnesium sulphate. The mixture was filtered and evaporated under reduce pressure. The resulting residue was purified by column chromatography on silica (220 g) eluting with a gradient of ethyl acetate in heptane (0% to 100%) to give the title compound as an off white amorphous solid (6.08 g, 52%).

UPLC-MS method 1: mass ion 573, 575 (MH$^+$ [$^{79}$Br]-tBu, MH$^+$ [$^{81}$Br]-tBu), 529, 531 (MH$^+$ [$^{79}$Br]—BOC, MH$^+$ [$^{81}$Br]—BOC) R$_t$=0.97 min Preparation 31: tert-butyl (3S)-3-[4-[(1R,2S)-1-(4-cyclopropylphenyl)-2-[(2,2,2-trifluoroacetyl)amino]propoxy]benzoyl]oxypiperidine-1-carboxylate

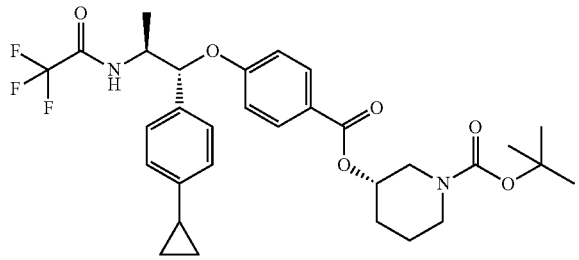 [SMILES: C[C@H](NC(=O)C(F)(F)F)[C@H](Oc1ccc(C(=O)O[C@H]2CCCN(C(=O)OC(C)(C)C)C2)cc1)c1ccc(C2CC2)cc1]

Using a procedure similar to that described for Preparation 25, but using the bromide described in Preparation 30, the title compound was prepared as an amorphous solid (4.6 g, 97%).

UPLC-MS method 1: Mass ion 535 (MH$^+$-tBu), 491 (MH$^+$—BOCC, MH$^+$) Rt=0.98 min Preparation 32: tert-butyl (3R)-3-[[5-[(1R,2S)-1-(p-tolyl)-2-[(2,2,2-trifluoroacetyl)amino]propoxy]pyridine-2-carbonyl]amino]pyrrolidine-1-carboxylate

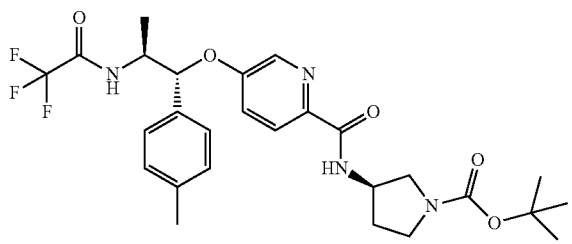 [SMILES: Cc1ccc([C@@H](Oc2ccc(C(=O)N[C@@H]3CCN(C(=O)OC(C)(C)C)C3)nc2)[C@H](C)NC(=O)C(F)(F)F)cc1]

Using a procedure similar to that described for Preparation 15, but using tert-butyl (3R)-3-aminopyrrolidine-1-carboxylate instead of tert-butyl (3S)-3-aminopiperidine-1-carboxylate, the title compound was prepared as an amorphous solid.

UPLC-MS method 2: Mass ion 550.24 (M$^+$), R$_t$=2.53 min

Preparation 33:
(3R)-5-oxotetrahydrofuran-3-carboxylic acid

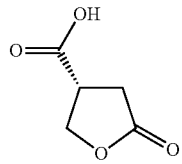

Sodium periodate (114 g, 533 mmol) was carefully added in small portions to a rapidly stirred mixture of (4S)-4-vinyltetrahydrofuran-2-one (15 g, 133 mmol) and ruthenium trichloride (1.39 g, 6.7 mmol) dissolved in a mixture tetrachloromethane (150 mL), acetonitrile (150 mL) and water (225 mL). The reaction is very exothermic and the reaction mixture was allowed to reach 50° C. during the addition of sodium periodate. Once all of the sodium periodate had been added the mixture was stirred for an additional 1 hr. Sodium chloride (200 g) was added to the reaction mixture along with ethyl acetate (250 mL) and then rapidly stirred for 5 minutes. The ethyl acetate was decanted off and replaced with fresh ethyl acetate (250 mL) and rapidly stirred again and decanted off, process repeated with 4 more lots of ethyl acetate. The ethyl acetate extracts were combined and dried over magnesium sulphate, filtered and evaporated under reduced pressure to give a dark brown oil. The oil was stored in the freezer overnight during which time it turns black. This black material was dissolved in dichloromethane (200 mL) and filtered through a small plug of silica to remove the black impurity. The filtrate was evaporated to give the title compound as a crystalline white solid (12.2 g, 70%).

$^1$H NMR (300 MHz, CDCl$_3$d) δ=10.81 (s, 1H), 4.69-4.39 (m, 2H), 3.53 (dddd, J=9.6, 8.0, 6.9, 6.3, 1H), 3.05-2.67 (m, 2H).

Preparation 34:
(3S)-5-oxotetrahydrofuran-3-carboxylic acid

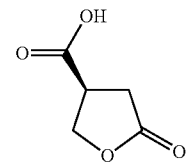

Using a procedure similar to that described for Preparation 33, but using (4R)-4-vinyltetra hydrofuran-2-one instead of (4S)-4-vinyltetrahydrofuran-2-one, the title compound was prepared as a waxy brown solid.

$^1$H NMR (300 MHz, CDCl$_3$d) δ=10.81 (s, 1H), 4.69-4.39 (m, 2H), 3.53 (dddd, J=9.6, 8.0, 6.9, 6.3, 1H), 3.05-2.67 (m, 2H).

Preparation 35: 4-[(1R,2S)-2-amino-1-(p-tolyl)propoxy]benzonitrile

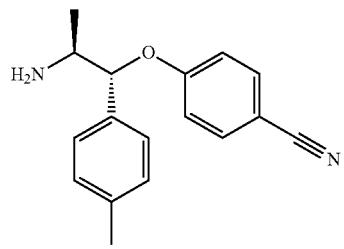

Sodium hydride (60% wt/wt in mineral oil, 0.67 g, 17 mmol) was added in small portions to a solution of the amino alcohol from Preparation 4 (2.5 g, 15 mmol) in N-methylpyrrolidin-2-one (30 mL). The reaction was stirred at 60° C. for 0.5 hr before adding 4-fluorobenzonitrile (2.2 g, 18 mmol) and heating for a further 0.5 hr. The reaction mixture was cooled and carefully poured into a mixture of diethyl ether (300 mL) and 4M aqueous hydrochloric acid (150 mL). The diethyl ether layer was extracted again with 4M aqueous hydrochloric acid (100 mL). The combined aqueous layers were then back extracted with heptane (100 mL) and then made basic with 32% aqueous sodium hydroxide solution and extracted with diethyl ether (2×100 mL). These diethyl ether layers were then washed with water (2×30 mL), saturated brine and dried over sodium sulphate, filtered and evaporated under reduced pressure. The resulting oil was purified by column chromatography on silica (80 g) eluting with a gradient of methanol:triethylamine (1:1) in ethyl acetate (0% to 10%) to give the title compound as a colourless oil (1.38 g, 34%).

$^1$H NMR (300 MHz, CDCl$_3$-d) δ=7.56-7.40 (m, 1H), 7.22-7.04 (m, 1H), 7.01-6.69 (m, 1H), 4.91 (d, J=5.3, OH), 3.40-3.24 (m, OH), 2.33 (s, 1H), 1.16 (d, J=6.6, 1H).

Preparation 36: 4-[(1R,2S)-2-amino-1-(p-tolyl) propoxy]benzoic acid

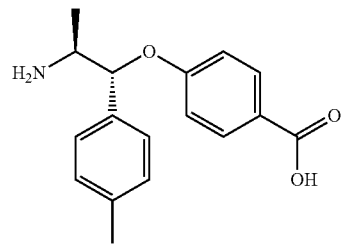 [SMILES: Cc1ccc([C@@H](Oc2ccc(C(=O)O)cc2)[C@H](C)N)cc1]

2M Aqueous sodium hydroxide (62 mL, 124 mmol) was added to a solution of the nitrile from Preparation 35 (1.38 g, 5.1 mmol) in methanol (12 mL) and the resulting mixture heated to 85° C. for 3 hr. The mixture was concentrated under reduced pressure to a small volume (20 mL) and neutralized (pH 7) with 4M aqueous hydrochloric acid. The mixture was further reduced in volume (20 mL) under reduced pressure and the resulting white solid filtered off and washed with a small volume of cold water to give the title compound (1.16 g, 79%).

$^1$H NMR (300 MHz, DMSO-d$_6$) δ=7.78 (d, J=8.8, 2H), 7.37-7.07 (m, 4H), 6.93 (d, J=8.8, 2H), 5.30 (d, J=4.6, 1H), 3.46-3.16 (m, 1H), 2.27 (s, 3H), 1.07 (d, J=6.5, 3H).

Preparation 37: 4-[(1R,2S)-1-(p-tolyl)-2-[(2,2,2-trifluoroacetyl)amino]propoxy]benzoic acid

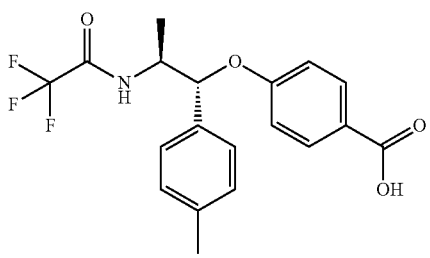

Trifluoroacetic anhydride (1.13 mL, 8.13 mmol) was added to a suspension of the amino acid from Preparation 36 in dichloromethane (50 mL), acetonitrile (20 mL) and triethylamine (5.66 mL, 40 mmol). The mixture was stirred for 1 hr before filtering. The filtrate was evaporated under reduced pressure and purified by column chromatography on silica gel (80 g) eluting with a gradient of ethyl acetate in heptane (0% to 30%) to give the title compound as an amorphous solid (0.93 g, 60%).

$^1$H NMR (300 MHz, CDCl$_3$-d) δ=7.95 (d, J=8.9, 2H), 7.18 (s, 4H), 6.87 (d, J=9.0, 2H), 6.47 (d, J=8.9, 1H), 5.40 (d, J=3.1, 1H), 4.62-4.39 (m, 1H), 2.34 (s, 3H), 1.25 (d, J=7.0, 3H).

Preparation 38: tert-butyl (3S)-3-[[4-[(1R,2S)-1-(p-tolyl)-2-[(2,2,2-trifluoroacetyl)amino]propoxy]benzoyl]amino]piperidine-1-carboxylate

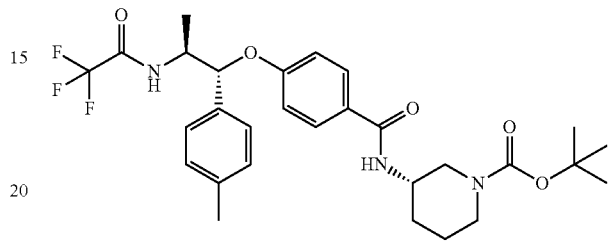

Using a procedure similar to that described for Preparation 15, but using the acid from Preparation 37, the title compound was prepared as an amorphous solid (63 mg, 85%).

UPLC-MS method 1: Mass ion 508 (MH$^+$-$^t$Bu), 464 (MH$^+$—BOC), R$_t$=0.89 min Preparation 39: tert-butyl (3S)-3-[4-[(1R,2S)-1-(p-tolyl)-2-[(2,2,2-trifluoroacetyl)amino]propoxy]benzoyl]oxypiperidine-1-carboxylate

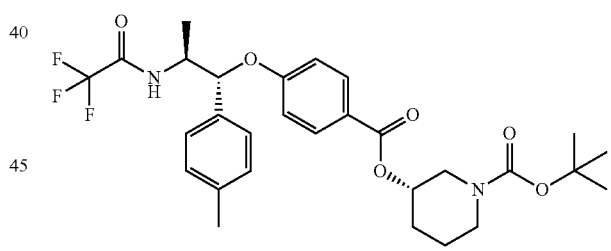

1-Ethyl-3-(3-dimethylaminopropyl) carbodiimide hydrochloride (25 mg, 0.131 mmol) was added to a solution of the acid from Preparation 37 (25 mg, 0.066 mmol), N,N-dimethylaminopyridine (16 mg, 0.131 mmol) and tert-butyl (3S)-3-hydroxypiperidine-1-carboxylate (20 mg, 0.098 mmol) in N,N-dimethylformamide (3 mL). The resulting mixture was shaken at room temperature for 20 hr before diluting with ethyl acetate (10 mL) and washing with 1M aqueous hydrochloric acid solution (2×3 mL), saturated sodium hydrogen carbonate (2×2 mL) and drying over magnesium sulphate to give the title compound as an oil (30 mg, 80%).

UPLC-MS method 1: Mass ion 563.3 (M–H$^+$) R$_t$=0.98 min

Preparation 40: tert-butyl (3S)-3-[4-[(1R,2S)-2-amino-1-(4-cyclopropylphenyl)propoxy]benzoyl]oxypiperidine-1-carboxylate hydrochloride

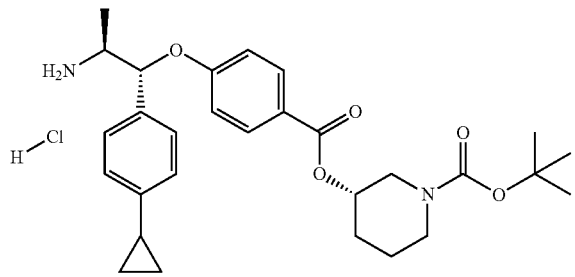

1M Aqueous lithium hydroxide (68 mL, 69.8 mmol) was added to a solution of the trifluoroacetamide from Preparation 31 (33 g, 55.88 mmol) in tetrahydrofuran (330 mL) and the resulting mixture stirred at room temperature for 24 hr. The mixture was concentrated under reduced pressure and the resulting residue diluted with water (100 mL) and extracted with ethyl acetate (4×250 mL). The combined ethyl acetate layers were washed with 2M aqueous hydrochloric acid (100 mL), saturated brine and dried over magnesium sulphate. The mixture was filtered and the magnesium sulphate filter cake washed with 20% methanol in ethyl acetate (5×100 mL). The combined ethyl acetate filtrates were evaporated under reduced pressure to give a yellow solid. The yellow solid was slurried with tert-butyl methyl ether (3×100 mL) and filtered and dried at 70° C. to give the title compound as a very pale yellow solid (23.4 g, 79%).

UPLC-MS method 1: Mass ion 439 (MH$^+$-tBu), 495 (MH$^+$) Rt=0.74 min

Preparation 41: tert-butyl (3S)-3-[4-[(1R,2S)-1-(4-cyclopropylphenyl)-2-[[(2R)-tetrahydrofuran-2-carbonyl]amino]propoxy]benzoyl]oxypiperidine-1-carboxylate

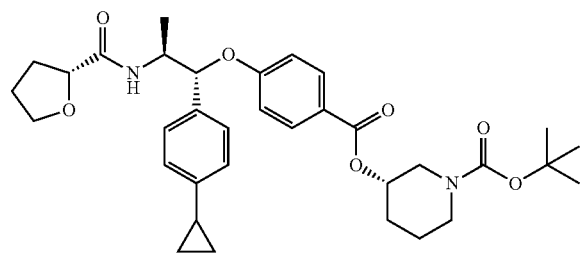 [SMILES: C[C@H](NC(=O)[C@H]1CCCO1)[C@H](Oc1ccc(C(=O)O[C@H]2CCCN(C(=O)OC(C)(C)C)C2)cc1)c1ccc(C2CC2)cc1]

Oxalyl chloride (36 mL, 0.425 mol) was added to a solution of (2R)-tetrahydrofuran-2-carboxylic acid (9.87 g, 85 mmol) in dichloromethane (300 mL). Dimethylformamide (50 μL, cat.) was added and the resulting mixture stirred for 2 hrs before evaporating under reduced pressure. The residue was re-dissolved in dichloromethane (200 mL) and evaporated under reduced pressure, this process was repeated a further two times to give intermediate (2R)-tetrahydrofuran-2-carbonyl chloride. (2R)-tetrahydrofuran-2-carbonyl chloride (7.5 g, 52.4 mmol) was dissolved in dichloromethane (50 mL) and added drop-wise to an ice cooled solution of the amine from preparation 40 (22.8 g, 42.9 mmol) and 4-methylmorpholine (14 mL, 129 mmol) in dichloromethane (400 mL). The resulting mixture was stirred at 5° C. for 20 mins and then evaporated under reduced pressure. The resulting residue was re-suspended in ethyl acetate (500 mL) and washed with 1M aqueous hydrochloric acid (3×100 mL) followed by saturated aqueous sodium hydrogen carbonate (2×50 mL) and brine. The ethyl acetate solution was dried over magnesium sulphate, filtered through a small plug of silica and evaporated under reduced pressure. The residue was dissolved in dichloromethane (3×200 mL) and evaporated to give the title compound as a pale yellow foam (23.5 g, 92%).

UPLC-MS method 1: Mass ion 537 (MH$^+$-tBu), Rt=0.95 min

Preparation 42: tert-butyl (3S)-3-[4-[(1R,2S)-1-(4-cyclopropylphenyl)-2-[[(2S)-tetrahydrofuran-2-carbonyl]amino]propoxy]benzoyl]oxypiperidine-1-carboxylate

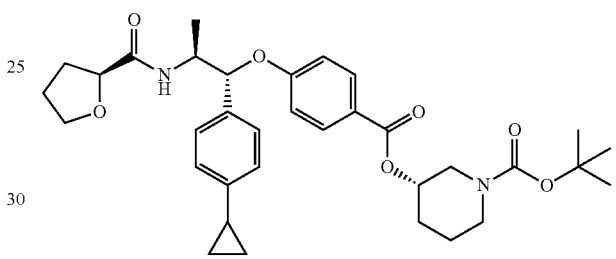

EDAC (1520 mg, 7.9 mmol) was added to a solution of the amine from preparation 40 (3.0 g, 5.65 mmol), (2S)-tetrahydrofuran-2-carboxylic acid (787 mg, 6.78 mmol) and Oxyma® (ethyl-2-cyano-2-hydroxyimino-acetate) (321 mg, 2.26 mmol) in acetonitrile (30 mL). To the resulting mixture triethylamine (1.97 mL, 14 mmol) was added and the mixture stirred at room temperature for 20 hrs.

The reaction mixture was evaporated under reduced pressure. The resulting residue was dissolved in ethyl acetate (200 mL) and washed with 1M aqueous hydrochloric acid (2×100 mL) followed by saturated aqueous sodium hydrogen carbonate (1×100 mL). The ethyl acetate solution was co evaporated with toluene (2×200 mL) to give the title compound as a clear yellow oil (3.36 g, 100%). UPLC-MS method 1: Mass ion 537 (MH$^+$-tBu), Rt=0.954 min Preparation 43: [(3S)-3-piperidyl] 4-[(1R,2S)-1-(4-cyclopropylphenyl)-2-[[(2R)-tetrahydrofuran-2-carbonyl]amino]propoxy]benzoate hydrochloride

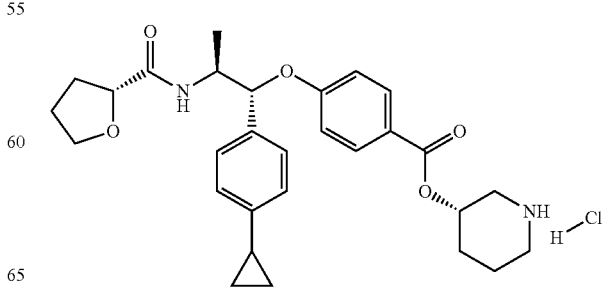

Hydrochloric acid (4M in 1,4-dioxane, 60 mL) was added to a solution of the carbamate from Preparation 41 (23 g, 38.8 mmol) in dichloromethane (100 mL). The reaction mixture was rapidly stirred at room temperature for 0.33 hr and then evaporated under reduced pressure to give the titled compound as a white foam. (20.5 g, 100%) UPLC-MS method 1: Mass ion 493 (MH⁺), Rt 0.60 min.

Preparation 44: [(3S)-3-piperidyl] 4-[(1R,2S)-1-(4-cyclopropylphenyl)-2-[[(2S)-tetrahydrofuran-2-carbonyl]amino]propoxy]benzoate hydrochloride

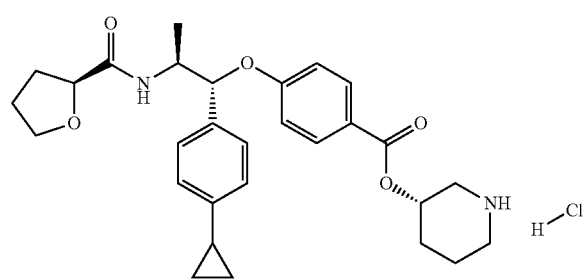

Using a procedure similar to that described for Preparation 43, but using the carbamate from Preparation 42, the title compound was prepared as an amorphous solid.

UPLC-MS method 1: Mass ion 493 (MH⁺), Rt 0.62 min.

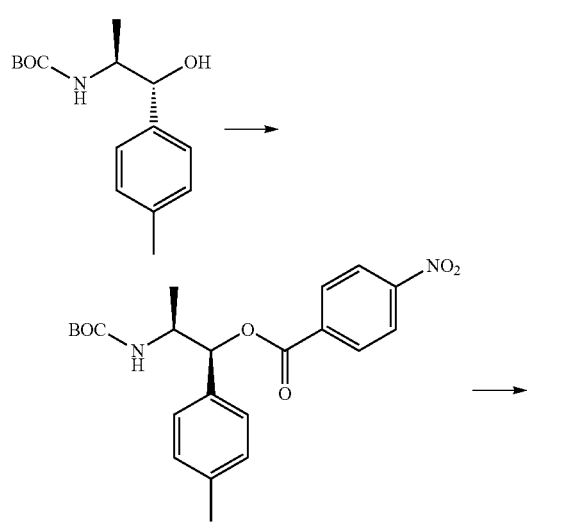

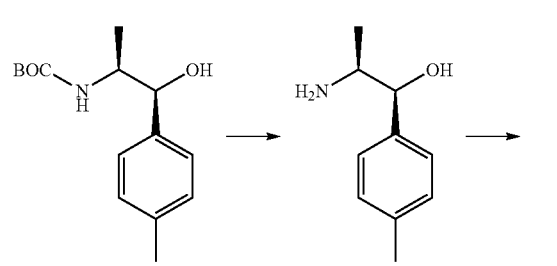

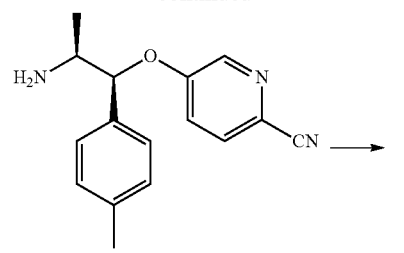

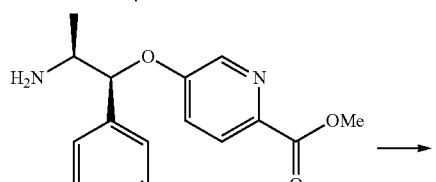

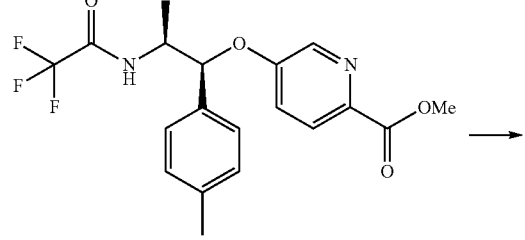

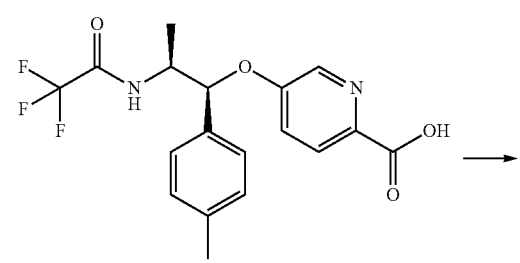

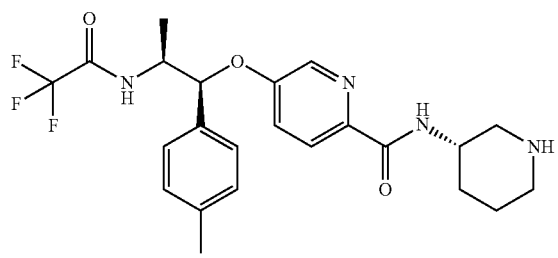

Preparation 45: [(1S,2S)-2-(tert-butoxycarbonylamino)-1-(p-tolyl)propyl] 4-nitrobenzoate

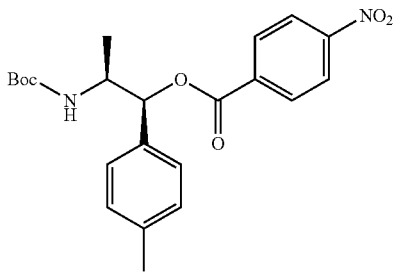 [SMILES: Cc1ccc([C@H](OC(=O)c2ccc([N+](=O)[O-])cc2)[C@H](C)NC(=O)OC(C)(C)C)cc1]

To a stirred solution of the alcohol from Preparation 3 (5 g, 18.867 mmol), triphenylphosphine (14.83 g, 56.6 mmol) and 4-nitro benzoic acid (3.78 g, 22.640 mmol) in tetrahydrofuran (100 mL, 20 vol) was added diethylazodicarboxylate (9.85 g, 56.6 mmol) drop wise at 0° C. for 5 min. The reaction was stirred at room temperature for 16 h. On completion, the reaction was diluted with water (100 mL). The resultant solution was extracted with ethyl acetate (2×100 mL). The combined organic layer was dried over sodium sulphate and concentrated under reduced pressure. The crude product was purified by silica gel (100-200 mesh) column chromatography (30-40% ethyl acetate in pet. ether as eluent) to afford the title compound as colorless gum (2.3 g, 33%). $^1$H NMR (CDCl$_3$, 400 MHz): δ=8.26 (s, 4H), 7.33 (m, =7.8 Hz, 2H), 7.19 (d, J=7.8 Hz, 2H), 5.74-5.72 (m, 1H), 4.53-4.49 (m, 1H), 4.34-4.30 (m, 1H), 2.34 (s, 3H), 1.32 (s, 9H), 1.07 (m, J=6.8 Hz, 3H).

Preparation 46: tert-butyl N-[(1S,2S)-2-hydroxy-1-methyl-2-(p-tolyl) ethyl]carbamate

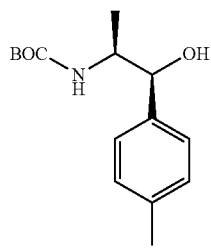 [SMILES: Cc1ccc([C@H](O)[C@H](C)NC(=O)OC(C)(C)C)cc1]

To a stirred solution of the carbamate from Preparation 45 (2 g) in methanol (20 mL, 10 vol) was added potassium carbonate (1 g, 7.246 mmol) at room temperature. The reaction was stirred at room temperature for 3 h. On completion, the reaction mixture was filtered and washed with methanol and concentrated under reduced pressure. The crude product was purified by silica gel (100-200 mesh) column chromatography (20% ethyl acetate in hexane as eluent) to afford the title compound as an off-white solid (1.1 g, 85%). $^1$H NMR (CDCl$_3$, 400 MHz): δ=7.20-7.24 (m, 2H), 7.13-7.19 (m, 2H), 4.83-4.80 (m, 1H), 4.62-4.59 (m, 1H), 4.00-3.98 (m, 1H), 3.09-3.07 (m, 1H), 2.28-2.39 (m, 3H), 1.37-1.52 (m, 9H), 0.99 (d, J=6.8 Hz, 3H). LCMS (ESI): m/z 266 [M+H]*; RT=2.65 min; (KINETEX-1.7u XB-C18 column, 0.05% formic acid in water with acetonitrile).

Preparation 47: (1S,2S)-2-amino-1-(p-tolyl)propan-1-ol

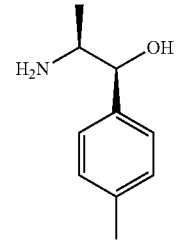

Using a procedure similar to that described for Preparation 4, but using the carbamate from Preparation 46, the title compound was prepared as a pale brown solid. $^1$H NMR (CDCl$_3$, 400 MHz): δ=7.21-7.24 (m, 2H), 7.12-7.17 (m, 2H), 4.21 (d, J=6.8 Hz, 1H), 3.09-3.07 (m, 2H), 2.34 (s, 3H), 1.80 (m, 2H), 1.03 (d, J=6.4 Hz, 3H) LCMS (ESI): m/z 166 [M+H]; 85%; RT=1.43 min; (KINETEX-1.7u XB-C18 column, 0.05% formic acid in water with acetonitrile).

Preparation 48: 5-[(1S,2S)-2-Amino-1-(p-tolyl)propoxy]pyridine-2-carbonitrile

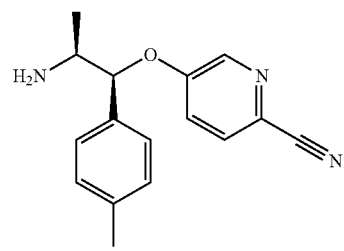 [SMILES: Cc1ccc([C@H](Oc2ccc(C#N)nc2)[C@H](C)N)cc1]

Using a procedure similar to that described for Preparation 11, but using the amino alcohol from Preparation 47, the title compound was prepared as a pale yellow oil, (600 mg, 74%). $^1$H NMR (CDCl$_3$, 300 MHz): δ=8.37 (d, J=2.6 Hz, 1H), 7.48 (d, 3=8.8 Hz, 1H), 7.10-7.20 (m, 5H), 4.84 (d, 3=6.6 Hz, 1H), 3.32-3.35 (m, 1H), 2.33 (s, 3H), 1.04 (d, 3=6.6 Hz, 3H). LCMS (ESI): m/z 268 [M+H]$^+$; 97.85%; RT=1.97 min (KINETEX-1.7u XB-C18 column, 0.05% formic acid in water with acetonitrile).

Preparation 49: methyl 5-[(1S,2S)-2-amino-1-(p tolyl)propoxy]pyridine-2-carboxylate

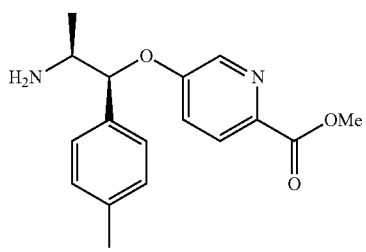 [SMILES: COC(=O)c1ccc(O[C@@H](c2ccc(C)cc2)[C@H](C)N)cn1]

Using a procedure similar to that described for Preparation 12, but using the nitrile from Preparation 48, the title compound was prepared as an off white solid, (500 mg, 74%). ¹H NMR (CDCl₃, 300 MHz): δ=8.37 (d, J=2.9 Hz, 1H), 7.95 (d, 3=8.8 Hz, 1H), 7.12-7.21 (m, 5H), 4.86 (d, 3=7.0 Hz, 1H), 3.93 (s, 3H), 3.31-3.38 (m, 1H), 2.31 (s, 3H), 1.05 (d, 3=6.6 Hz, 3H) LCMS (ESI): m/z 301 [M+H]⁺; 94%; RT=2.02 min (KINETEX-1.7u XB-C18 column, 0.05% formic acid in water with acetonitrile).

Preparation 50: Methyl 5-[(1S,2S)-1-(p-tolyl)-2-[(2,2,2-trifluoroacetyl)amino]propoxy]pyridine-2-carboxylate

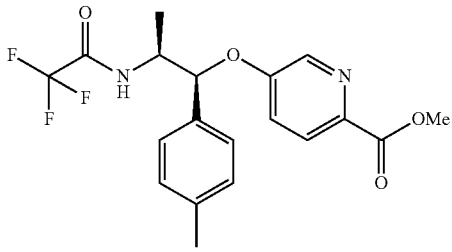 [SMILES: COC(=O)c1ccc(O[C@@H](c2ccc(C)cc2)[C@H](C)NC(=O)C(F)(F)F)cn1]

Using a procedure similar to that described for Preparation 13, but using the amine from Preparation 49, the title compound was prepared as a yellow liquid, (800 mg, 75%). ¹H NMR (CDCl₃, 400 MHz): δ=8.37 (d, J=2.4 Hz, 1H), 7.98-7.95 (m, 1H), 7.06-7.20 (m, 5H), 6.31-6.54 (m, 1H), 5.25-5.43 (m, 1H), 4.43-4.60 (m, 1H), 3.94 (s, 3H), 2.31 (s, 3H), 1.23-1.38 (m, 3H) LCMS (ESI): m/z 397 [M+H]⁺; 38.45%; RT=1.24 min+59.63%; RT=2.84 (KINETEX-1.7u XB-C18 column, 0.05% formic acid in water with acetonitrile).

Preparation 51: 5-[(1S,2S)-1-(p-tolyl)-2-[(2,2,2-trifluoroacetyl)amino]propoxy]pyridine-2-carboxylic acid

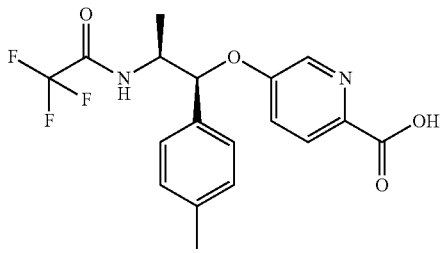 [SMILES: Cc1ccc([C@H](Oc2ccc(C(=O)O)nc2)[C@H](C)NC(=O)C(F)(F)F)cc1]

Using a procedure similar to that described for Preparation 14, but using the ester from Preparation 50, the title compound was prepared as an off-white solid (600 mg, 89%).

¹H NMR (CDCl₃, 400 MHz): δ=8.25-8.23 (m, 1H), 8.03-8.05 (d, J=8.8 Hz, 1H), 7.15-7.17 (m, 5H), 6.29-6.30 (m, 1H), 5.30 (d, J=4.4 Hz, 1H), 4.50-4.55 (m, 1H), 2.35 (s, 3H), 1.35 (d, J=6.8 Hz, 3H). LCMS (ESI): m/z 383 [M+H]⁺; 82.16%; RT=2.43 min (KINETEX-1.7u XB-C18 column, 0.05% formic acid in water with acetonitrile).

Preparation 52: tert-butyl (3S)-3-[[5-[(1S,2S)-1-(p-tolyl)-2-[(2,2,2-trifluoroacetyl)amino]propoxy]pyridine-2-carbonyl]amino]piperidine-1-carboxylate

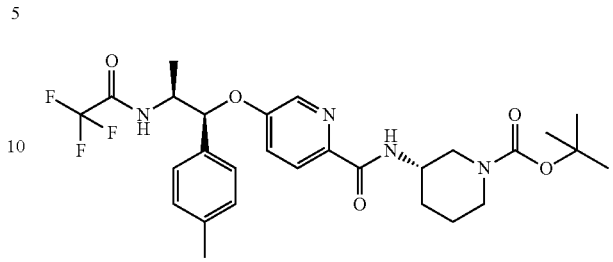

Using a procedure similar to that described for Preparation 15, but using the acid from Preparation 51, except the crude material was purified by SFC purification (Column: Chiralpak LuxCellulose-2(4.6*250) mm, 5u, % CO2: 80%, % co-solvent: 20% (100% Methanol), total flow: 100 g/min, back pressure: 100 bar, UV: 246 nm, stack time: 3.2 min, loading: 10 mg) to afford the title compound of as an off-white solid (400 mg).

¹H NMR (CDCl₃, 400 MHz): δ=8.14-8.12 (m, 1H), 8.01 (d, J=8.8 Hz, 1H), 7.89-7.93 (m, 1H), 7.12-7.20 (m, 5H), 6.30-6.34 (m, 1H), 5.23 (d, J=4.4 Hz, 1H), 4.53 (m, 1H), 4.07 (m, 1H), 3.59 (m, 1H), 3.49 (d, J=5.4 Hz, 1H), 3.40 (m, 2H), 2.33 (s, 3H), 1.88 (m, 1H), 1.67-1.75 (m, 2H), 1.42 (s, 7H), 1.36 (d, J=6.8 Hz, 3H). LCMS (ESI): m/z 565 [M+H]⁺; 98%; RT=3.11 min (KINETEX-1.7u XB-C18 column, 0.05% formic acid in water with acetonitrile) and Chiral HPLC~99.7%, Rt=3.41 min [SFC METHOD: Injection volume: 10, Solvent: 0.5% DEA in Methanol, Column: Chiralpak LuxCellulose-2(4.6*250) mm, 5u, Well location: 16D, Column Temperature: 29.9, Flow: 3, Pressure: 100, RT: 3.41 min peak1 and RT: 4.54 min peak2].

Preparation 53: tert-butyl (3S)-3-[[5-[(1S,2S)-1-(p-tolyl)-2-[(2,2,2-trifluoroacetyl)amino]propoxy]pyridine-2-carbonyl]amino]piperidine-1-carboxylate

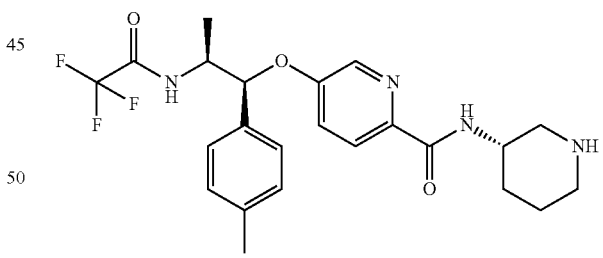

Using a procedure similar to that described for Preparation 15, but using the acid from Preparation 51, to afford the title compound of as a pale green solid (300 mg, 93%).

¹H NMR (DMSO, 300 MHz): δ=9.50-9.54 (m, 1H), 8.63-8.67 (m, 1H), 8.25 (d, J=2.6 Hz, 1H), 7.89 (d, J=8.4 Hz, 1H), 7.37-7.41 (m, 1H), 7.22-7.28 (m, 2H), 7.13-7.19 (m, 2H), 5.43 (d, J=6.2 Hz, 1H), 4.25-4.29 (m, 1H), 4.12-4.16 (m, 1H), 3.07-3.23 (m, 2H), 2.84-2.94 (m, 1H), 2.71-2.75 (m, 1H), 2.26 (s, 3H), 1.80-1.84 (m, 2H), 1.60-1.71 (m, 2H), 1.30 (d, J=6.6 Hz, 3H). LCMS (ESI): m/z 465 [M+H]⁺; 99%; RT=1.24 min. (KINETEX-1.7u XB-C18 column, 0.05% formic acid in water with acetonitrile) and chiral HPLC~99%; SFC METHOD: Injection volume: 10, Solvent: 0.5% DEA in Methanol, Column: Chiralpak LuxCellulose 2(4.6*250) mm, 5u, Column Temperature: 29.9, Flow: 3, Pressure: 100, RT: 4.17 min.

EXAMPLES

Example 1: N-[(3S)-1-[(3R)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide (Compound 1)

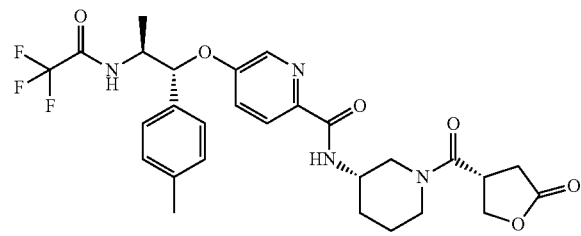 [SMILES: Cc1ccc([C@@H](Oc2ccc(C(=O)N[C@H]3CCCN(C(=O)[C@H]4COC(=O)C4)C3)nc2)[C@H](C)NC(=O)C(F)(F)F)cc1]

2M Oxalyl chloride (40 mL, 80 mmol) in dichloromethane was added to a solution of the lactone from Preparation 33 (1.9 g, 14.6 mmol) in dichloromethane (80 mL) followed by catalytic DMF (0.02 mL). The reaction mixture was stirred at room temperature for 1 hr and then evaporated under reduced pressure to give a yellow gum. This gum was dissolved in toluene (50 mL) and evaporated under reduced pressure, process repeated to remove the excess oxalyl chloride. The resulting acid chloride was dissolved in dichloromethane (20 mL) and added to a solution of the amine from Preparation 16 (5.52 g, 11.9 mmol) and 4-methylmorpholine (3 mL, 27.3 mmol) in dichloromethane (150 mL) at 5° C. The reaction was stirred at 5° C. for 0.5 hr and then evaporated under reduced pressure. The residue was dissolved in dichloromethane and purified by column chromatography on silica (400 g) eluting with 100% ethyl acetate to give a white foam (6.7 g). This white foam was dissolved in ethyl acetate (25 mL) and diethyl ether (200 mL) slowly added. The resulting white gummy solid was stirred for 2 hr and then filtered off. The resulting white powder was dissolved in refluxing ethyl acetate (250 mL) and the resulting solution concentrated under reduced pressure to approximately 50 mL and seeded with a small amount of seed crystals (white powder above). This mixture was stored in the freezer overnight and the resulting white crystals filtered off and dried under vacuum to give the title compound (4.8 g, 70%).

Mpt: 207.5° C.

UPLC-MS method 1: Mass ion 577 (MH+), $R_t$=0.74 min

UPLC-MS method 2: Mass ion 576.22 (M+), $R_t$=2.3 min $^1$H NMR (600 MHz, DMSO-d$_6$) Mixture of rotamers δ=9.52 (s, 1H), 8.43 (dd, J=26.8, 8.3, 1H), 8.24 (dd, J=11.9, 2.8, 1H), 7.90 (dd, J=14.4, 8.7, 1H), 7.39 (td, J=8.8, 2.9, 1H), 7.25 (d, J=7.9, 2H), 7.16 (d, J=7.9, 2H), 5.41 (dd, J=7.9, 6.0, 1H), 4.60 (t, J=8.5, 0.53H), 4.44 (t, J=8.4, 0.47H), 4.27 (ddd, J=8.4, 5.7, 2.5, 2H), 4.21 (dd, J=12.5, 4.1, 0.47H), 4.16-4.10 (m, 0.53H), 3.86-3.69 (m, 3H), 3.09-2.96 (m, 1H), 2.82-2.55 (m, 3H), 2.26 (s, 3H), 1.84 (m, J=11.8, 11.0, 3.4, 1H), 1.77-1.61 (m, 2H), 1.55-1.36 (m, 1H), 1.30 (dd, J=6.9, 1.2, 3H).

Example 2: 5-[(1R,2S)-1-(4-cyclopropylphenyl)-2-[(2,2,2-trifluoroacetyl)amino]propoxy]-N-[(3S)-1-[(3R)-5-oxotetrahydrofuran-3-carbonyl]-3-piperidyl]pyridine-2-carboxamide (Compound 2)

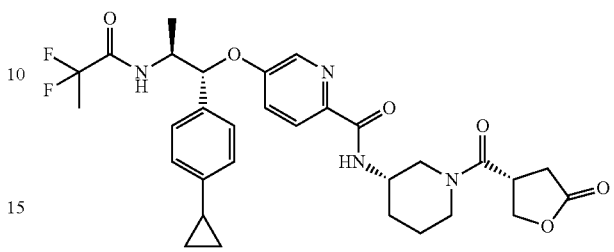

Trifluoroacetic acid (4 mL) was added to a solution of the carbamate from Preparation 25 (0.752 g, 1.275 mmol) in acetonitrile (4 mL) and the resulting solution stirred at room temperature for 0.2 hr. The reaction mixture was evaporated under reduced pressure. The resulting residue was dissolved in 2M acetic acid in methanol and purified by ion exchange chromatography (10 g SCX cartridge) eluting with 100% methanol followed by 2M ammonia in methanol. The ammonical methanol eluent was evaporated under reduced pressure to give the crude amine intermediate (5-[(1R,2S)-1-(4-cyclopropylphenyl)-2-[(2,2,2-trifluoroacetyl)amino]propoxy]-N-[(3S)-3-piperidyl]pyridine-2-carboxamide).

This crude amine intermediate was dissolved in N,N-dimethylformamide (30 mL) along with the acid from preparation 33 (0.248 g, 1.9 mmol) and diisopropylethylamine (0.89 mL, 5.1 mmol) and finally N,N,N',N'-tetramethyl-O-(1H-benzotriazol-1-yl)uronium hexafluorophosphate (0.965 g, 2.55 mmol) was added. The resulting mixture was stirred at room temperature for 1 hr before evaporating under reduced pressure. The residue obtained was dissolved in ethyl acetate (150 mL) and washed with 10% aqueous citric acid solution (2×20 mL) followed by saturated sodium hydrogen carbonate (1×50 mL). The solution was dried over magnesium sulphate, filtered and evaporated under reduced pressure. The resulting residue was purified by column chromatography on silica eluting with a gradient of ethyl acetate in heptane (0% to 100%) to give the title compound as a white amorphous solid (0.55 g, 72%).

UPLC-MS method 2: Mass ion 602.24 (M+), $R_t$=2.36 min.

$^1$H NMR (300 MHz, DMSO-d$_6$) mixture of rotamers, δ=9.48 (d, J=8.5, 1H), 8.40 (dd, J=13.9, 8.1, 1H), 8.23 (dd, J=5.4, 2.8, 1H), 7.95-7.75 (m, 1H), 7.38 (ddd, J=7.8, 4.5, 2.9, 1H), 7.23 (d, J=8.1, 2H), 7.04 (d, J=8.2, 2H), 5.41 (t, J=5.1, 1H), 4.59 (t, J=8.5, 0.55H), 4.44 (t, J=8.4, 0.45H), 4.39-4.00 (m, 3H), 3.78 (m, 3H), 3.03 (m, 1H), 2.86-2.57 (m, 3H), 1.97-1.60 (m, 4H), 1.60-1.35 (m, 1H), 1.29 (d, J=6.8, 3H), 0.92 (dd, J=8.3, 2.4, 2H), 0.79-0.50 (m, 2H).

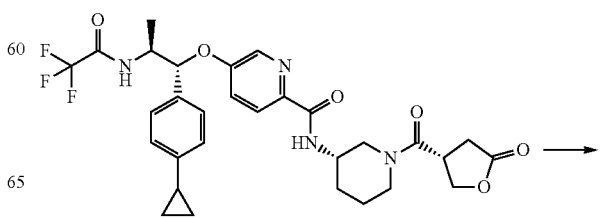

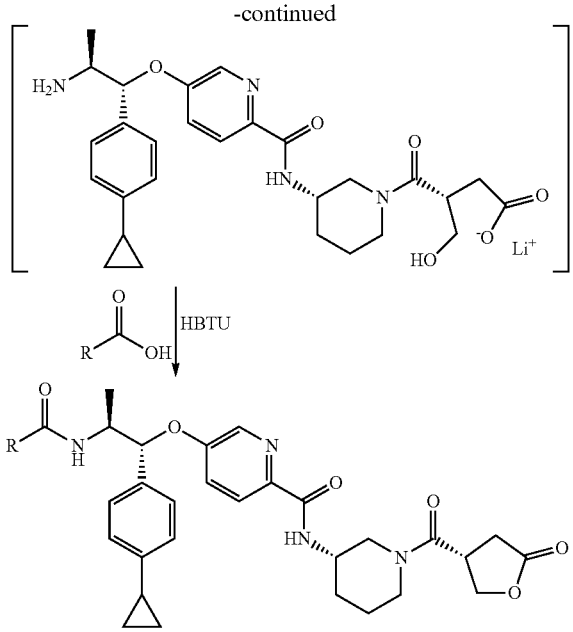

Example 3: 5-[(1R,2S)-1-(4-cyclopropylphenyl)-2-(2,2-difluoropropanoylamino)propoxy]-N-[(3S)-1-[(3R)-5-oxotetrahydrofuran-3-carbonyl]-3-piperidyl]pyridine-2-carboxamide (Compound 3)

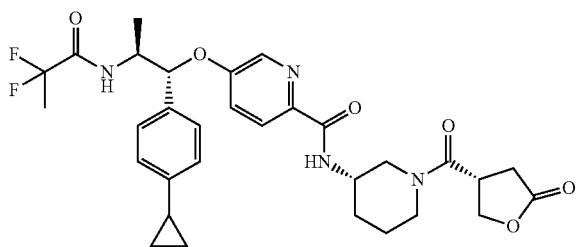 [SMILES: C[C@H](NC(=O)C(C)(F)F)[C@H](Oc1ccc(C(=O)N[C@H]2CCCN(C(=O)[C@H]3COC(=O)C3)C2)nc1)c1ccc(C2CC2)cc1]

Aqueous lithium hydroxide solution (1M, 2 mL, 2 mmol) was added to a solution of the compound from Example 2 (100 mg, 0.166 mmol) and the resulting solution heated to 70° C. for 1.5 hr. The reaction mixture was evaporated under reduced pressure and the resulting residue suspended in toluene (2×50 mL) and evaporated to remove any residual water to give the deprotected ring opened intermediate. This intermediate (0.018 mmol), 2,2-difluoropropanoic acid (3 mg, 0.027 mmol) and N,N,N',N'-tetramethyl-O-(1H-benzotriazol-1-yl)uronium hexafluorophosphate (17 mg, 0.045 mmol) were dissolved in N,N-dimethylformamide (0.5 mL) and finally diisopropylethylamine (0.013 mL, 0.072 mmol) added. The resulting mixture was heated to 40° C. for and then purified by preparative reverse phase hplc using a gradient of acetonitrile in 0.1% aqueous formic acid (10% to 100%) to give the title compound as an amorphous solid.

UPLC-MS method 2: Mass ion 598.26 (M+), $R_t$=2.32 min.

Example 4-21

The compounds of the following tabulated examples (Table 1) of the general formula:

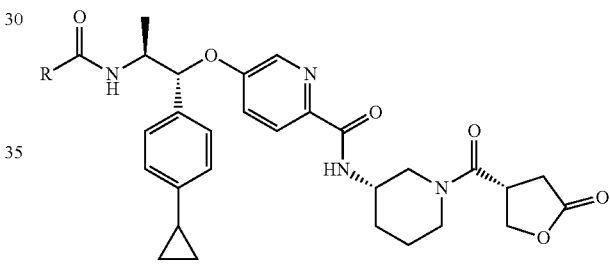

were prepared by a similar method to that of example 3 using the appropriate acid instead of 2,2-difluoropropanoic acid.

TABLE 1

| Example (Compound) | R—CO$_2$H | Name | Mass[1] Ion | $R_t$[1] (min) |
|---|---|---|---|---|
| 4 | isothiazole-3-carboxylic acid | N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isothiazole-3-carboxamide | 617.23 | 2.35 |
| 5 | isothiazole-5-carboxylic acid | N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isothiazole-5-carboxamide | 617.23 | 2.35 |

TABLE 1-continued

| Example (Compound) | R—CO₂H | Name | Mass¹ Ion | R_t¹ (min) |
|---|---|---|---|---|
| 6 | oxazole-2-carboxylic acid | N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]oxazole-2-carboxamide | 601.25 | 2.23 |
| 7 | thiazole-4-carboxylic acid | N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]thiazole-4-carboxamide | 617.23 | 2.29 |
| 8 | 3-methylisoxazole-5-carboxylic acid | N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]-3-methyl-isoxazole-5-carboxamide | 615.27 | 2.34 |
| 9 | oxazole-5-carboxylic acid | N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]oxazole-5-carboxamide | 601.25 | 2.16 |
| 10 | (2S)-2-hydroxybutanoic acid | 5-[(1R,2S)-1-(4-cyclopropylphenyl)-2-[[(2S)-2-hydroxybutanoyl]amino]propoxy]-N-[(3S)-1-[(3R)-5-oxotetrahydrofuran-3-carbonyl]-3-piperidyl]pyridine-2-carboxamide | 592.29 | 2.19 |
| 11 | (2S)-2-hydroxypropanoic acid | 5-[(1R,2S)-1-(4-cyclopropylphenyl)-2-[[(2R)-2-hydroxypropanoyl]amino]propoxy]-N-[(3S)-1-[(3R)-5-oxotetrahydrofuran-3-carbonyl]-3-piperidyl]pyridine-2-carboxamide | 578.27 | 2.10 |
| 12 | isoxazole-5-carboxylic acid | N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isoxazole-5-carboxamide | 601.25 | 2.25 |
| 13 | (2R)-2-hydroxybutanoic acid | 5-[(1R,2S)-1-(4-cyclopropylphenyl)-2-[[(2R)-2-hydroxybutanoyl]amino]propoxy]-N-[(3S)-1-[(3R)-5-oxotetrahydrofuran-3-carbonyl]-3-piperidyl]pyridine-2-carboxamide | 592.29 | 2.15 |
| 14 | 2-methoxyacetic acid | 5-[(1R,2S)-1-(4-cyclopropylphenyl)-2-[(2-methoxyacetyl)amino]propoxy]-N-[(3S)-1-[(3R)-5-oxotetrahydrofuran-3-carbonyl]-3-piperidyl]pyridine-2-carboxamide | 578.27 | 2.19 |

TABLE 1-continued

| Example (Compound) | R—CO₂H | Name | Mass¹ Ion | R_t¹ (min) |
|---|---|---|---|---|
| 15 | | 5-[(1R,2S)-1-(4-cyclopropylphenyl)-2-[(2-hydroxy-2-methyl-propanoyl)amino]propoxy]-N-[(3S)-1-[(3R)-5-oxotetrahydrofuran-3-carbonyl]-3-piperidyl]pyridine-2-carboxamide | 592.29 | 2.15 |
| 16 | | 5-[(1R,2S)-1-(4-cyclopropylphenyl)-2-(3-hydroxypropanoylamino)propoxy]-N-[(3S)-1-[(3R)-5-oxotetrahydrofuran-3-carbonyl]-3-piperidyl]pyridine-2-carboxamide | 578.27 | 2.06 |
| 17 | | 5-[(1R,2S)-1-(4-cyclopropylphenyl)-2-[(1-hydroxycyclobutanecarbonyl)amino]propoxy]-N-[(3S)-1-[(3R)-5-oxotetrahydrofuran-3-carbonyl]-3-piperidyl]pyridine-2-carboxamide | 604.29 | 2.21 |
| 18 | | 5-[(1R,2S)-1-(4-cyclopropylphenyl)-2-[(1-hydroxycyclopropanecarbonyl)amino]propoxy]-N-[(3S)-1-[(3R)-5-oxotetrahydrofuran-3-carbonyl]-3-piperidyl]pyridine-2-carboxamide | 590.27 | 2.15 |
| 19² | | N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]oxazole-4-carboxamide | 601.25 | 2.23 |
| 20 | | 5-[(1R,2S)-1-(4-cyclopropylphenyl)-2-[[[(2S)-tetrahydrofuran-2-carbonyl]amino]propoxy]-N-[(3S)-1-[(3R)-5-oxotetrahydrofuran-3-carbonyl]-3-piperidyl]pyridine-2-carboxamide | 604.29 | 2.24 |
| 21 | | 5-[(1R,2S)-1-(4-cyclopropylphenyl)-2-[(2-hydroxyacetyl)amino]propoxy]-N-[(3S)-1-[(3R)-5-oxotetrahydrofuran-3-carbonyl]-3-piperidyl]pyridine-2-carboxamide | 564.26 | 2.08 |

¹UPLC-MS method 2 used.

²Compound 19: 1H NMR (600 MHz, DMSO-d6) δ = 8.57 (dd, J = 2.0, 1.0, 1H), 8.50 (dd, J = 2.2, 1.0, 1H), 8.45 (d, J = 7.9, 0.5H), 8.40 (d, J = 8.6, 0.5H), 8.25 (dd, J = 11.0, 2.8, 1H), 8.12 (dd, J = 8.9, 1.7, 1H), 7.89 (dd, J = 14.9, 8.7, 1H), 7.38 (ddd, J = 8.8, 7.7, 2.9, 1H), 7.26 (d, J = 7.9, 2H), 7.07-6.97 (m, 2H), 5.57 (t, J = 6.1, 1H), 4.68-4.36 (m, 2H), 4.31-4.09 (m, 2H), 3.78 (m, 3H), 3.11-2.97 (m, 1H), 2.82-2.55 (m, 3H), 1.84 (m, 2H), 1.80-1.57 (m, 2H), 1.28 (dd, J = 6.8, 2.1, 3H), 0.90 (dt, J = 8.4, 1.7, 2H), 0.72-0.46 (m, 2H).

Example 22: 5-[(1R,2S)-1-(4-cyclopropylphenyl)-2-[[(2R)-tetrahydrofuran-2-carbonyl]amino]propoxy]-N-[(3S)-1-[(3R)-5-oxotetrahydrofuran-3-carbonyl]-3-piperidyl]pyridine-2-carboxamide (Compound 22)

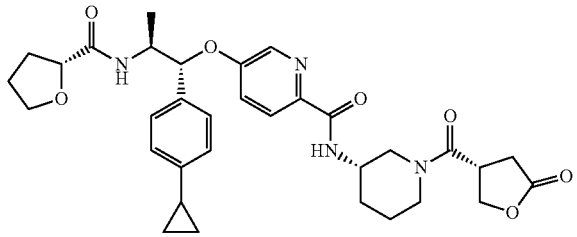 [SMILES: C[C@H](NC(=O)[C@H]1CCCO1)[C@H](Oc1ccc(C(=O)N[C@H]2CCCN(C(=O)[C@H]3COC(=O)C3)C2)nc1)c1ccc(C2CC2)cc1]

Hydrochloric acid (4M in dioxan, 40 mL) was added to a solution of the carbamate from Preparation 27 (1.25 g, 2.11 mmol) in dichloromethane (20 mL). The reaction mixture was rapidly stirred at room temperature for 0.33 hr and then evaporated under reduced pressure to give the intermediate deprotected amine (5-[(1R,2S)-1-(4-cyclopropylphenyl)-2-[[(2R)-tetrahydrofuran-2-carbonyl]amino]propoxy]-N-[(3S)-3-piperidyl]pyridine-2-carboxamide) (UPLC-MS method 1: Mass ion 493 (MH$^+$), Rt 0.56 min). Meanwhile, 2M Oxalyl chloride (40 mL, 80 mmol) in dichloromethane was added to a solution of the lactone from Preparation 33 (0.468 g, 3.6 mmol) in dichloromethane (20 mL) followed by catalytic DMF (0.01 mL). The reaction mixture was stirred at room temperature for 1 hr and then evaporated under reduced pressure to give a yellow gum. This gum was dissolved in toluene (50 mL) and evaporated under reduced pressure, process repeated to remove the excess oxalyl chloride. The resulting acid chloride was dissolved in dichloromethane (20 mL) and added to a solution of the intermediate amine (2.11 mmol) in dichloromethane (50 mL) and 4-methylmorpholine (2.6 mL, 24 mmol). This reaction mixture was stirred at 5° C. for 0.5 hr before being evaporated under reduced pressure. The residue was dissolved in ethyl acetate (200 mL) and washed with 5% aqueous citric acid solution (2×50 mL), saturated aqueous sodium hydrogen carbonate (1×50 mL), saturated brine (50 mL) and dried over magnesium sulphate, filtered and the filtrate evaporated under reduced pressure to give a brown amorphous solid (1.25 g). This solid was purified by column chromatography on silica gel (40 g) eluting with 100% ethyl acetate then a gradient of acetonitrile in ethyl acetate (0% to 70%). The resulting amorphous solid was dissolved in acetonitrile (50 mL) and enough water added to give a slightly cloudy solution (80 mL) and then acetonitrile added (2 mL) to give a clear solution. This solution was frozen and then lyophilized for 70 hr to give the title compound as a white amorphous solid (0.88 g, 70%).

UPLC-MS method 1: Mass ion 605 (MH$^+$), R$_t$=0.70 min
UPLC-MS method 2: Mass ion 604.29 (M$^+$), R$_t$=2.21 min
$^1$H NMR (600 MHz, DMSO-d$_6$), Mixture of rotamers, δ=8.45 (d, J=8.0, 1H), 8.24 (dd, J=10.5, 2.8, 1H), 7.90 (dd, J=14.6, 8.7, 1H), 7.62 (d, J=9.4, 1H), 7.38 (ddd, J=9.6, 7.1, 2.9, 1H), 7.24 (d, J=8.0, 2H), 7.02 (d, J=8.0, 2H), 5.39 (t, J=6.2, 1H), 4.60 (t, J=8.5, 0.53H), 4.44 (t, J=8.4, 0.47H), 4.34-4.06 (m, 4H), 3.89-3.65 (m, 5H), 3.11-2.96 (m, 1H), 2.83-2.55 (m, 3H), 1.87 (m, 3H), 1.78-1.57 (m, 3H), 1.54-1.38 (m, 1H), 1.32 (m, 2H), 1.23 (m, 3H), 0.91 (m, 2H), 0.67-0.53 (m, 2H).

Example 23: N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isoxazole-3-carboxamide (Compound 23)

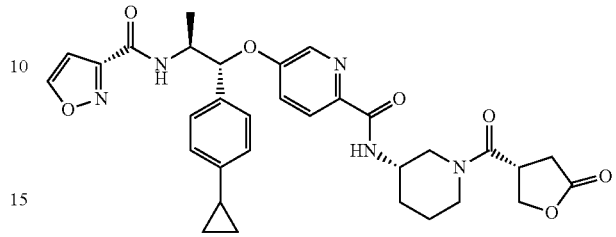

Using a procedure similar to that described for Example 22, but using the carbamate from Preparation 28 (1.4 g, 2.4 mmol) via intermediate amine N-[(1S,2R)-2-(4-cyclopropylphenyl)-1-methyl-2-[[6-[[(3S)-3-piperidyl]carbamoyl]-3-pyridyl]oxy]ethyl]isoxazole-3-carboxamide, the title compound was prepared as a white amorphous solid (0.85 g, 60%).

UPLC-MS method 1: Mass ion 602 (MH$^+$), R$_t$=0.73 min
UPLC-MS method 2: Mass ion 601.25 (M$^+$), R$_t$=2.29 min
$^1$H NMR (600 MHz, DMSO-d$_6$): Mixture of rotamers, δ=9.05 (s, 1H), 8.80 (d, J=8.5, 1H), 8.45 (d, J=8.0, 1H), 8.24 (dd, J=11.8, 2.9, 1H), 7.89 (dd, J=14.7, 8.7, 1H), 7.37 (td, J=8.3, 2.9, 1H), 7.26 (d, J=8.0, 2H), 7.03 (d, J=8.1, 2H), 6.80 (s, 1H), 5.51 (t, J=6.4, 1H), 4.60 (t, J=8.5, 0.5H), 4.51-4.37 (m, 1.5H), 4.33-4.10 (m, 2H), 3.92-3.68 (m, 3H), 3.09-2.95 (m, 1H), 2.81-2.55 (m, 3H), 1.85 (ddd, J=10.3, 8.4, 5.1, 2H), 1.79-1.59 (m, 2H), 1.55-1.36 (m, 1H), 1.35-1.23 (m, 3H), 0.90 (dd, J=8.5, 2.5, 2H), 0.66-0.56 (m, 2H).

Example 24: [(3S)-1-[(3R)-5-oxotetrahydrofuran-3-carbonyl]-3-piperidyl] 4-[(1R,2S)-1-(4-cyclopropylphenyl)-2-[(2,2,2-trifluoroacetyl)amino]propoxy]benzoate (Compound 24)

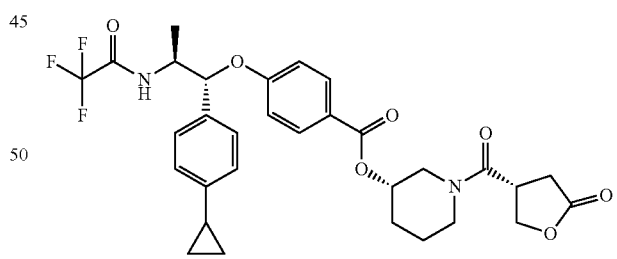

Using a procedure similar to that described for Example 2, but using the carbamate from Preparation 31 (4.6 g, 7.79 mmol), the title compound was prepared as a white amorphous solid (3.32 g, 90%).

UPLC-MS method 2: Mass ion 602.22 (M$^+$), R$_t$=2.51 min
$^1$H NMR (600 MHz, DMSO-d$_6$): Mixture of rotamers, δ=9.73-9.31 (m, 1H), 7.90-7.66 (m, 2H), 7.21 (dd, J=8.3, 2.0, 2H), 7.06-7.01 (m, 2H), 7.00-6.96 (m, 1H), 6.95-6.92 (m, 1H), 5.34 (dd, J=11.6, 6.1, 1H), 4.93 (m, 1H), 4.45 (ddd, J=10.4, 8.8, 7.9, 1H), 4.27-4.14 (m, 2H), 3.89-3.80 (m, 1H), 3.77-3.70 (m, 1H), 3.68-3.50 (m, 2H), 3.38 (m, 0.5H), 3.29 (m, 0.5H), 2.75-2.63 (m, 1H), 2.58 (dd, J=17.2, 6.0, 0.5H), 2.47 (dd, J=17.2, 9.0, 0.5H), 1.97-1.63 (m, 4H), 1.57 (m, 0.5H), 1.50 (m, 0.5H), 1.32-1.23 (m, 3H), 0.97-0.86 (m, 2H), 0.68-0.56 (m, 2H).

sium sulphate, filtered and evaporated under reduced pressure to give an amorphous solid. This solid was dissolved in tetrahydrofuran (100 mL) and 10% aqueous sodium carbonate solution (5 mL) added. The resulting solution was stirred at room temperature for 70 hr. The mixture was evaporated under reduced pressure and the resulting residue was diluted with dichloromethane (70 mL) and washed with 10% aqueous citric acid solution (2×25 mL), saturated aqueous sodium hydrogen carbonate (1×25 mL) and then dried over magnesium sulphate, filtered and evaporated. The resulting gum was purified by column chromatography on silica gel (120 g) eluting with a gradient of ethyl acetate in heptane (0% to 100%) to give the carbamate intermediate. This intermediate carbamate was dissolved in 4M hydrochloric acid in dioxan (5 mL) and stirred at room temperature for 0.5 hr. This mixture was concentrated, by evaporation under reduced pressure, to a small volume. The resulting mixture was filtered to give the intermediate amine salt as a white solid. This intermediate amine salt (0.015 mmol) was dissolved in N,N-dimethylformamide (0.15 mL) and the appropriate acid (0.023 mmol) added followed by a solution of N,N,N',N'-tetramethyl-O-(1H-benzotriazol-1-yl)uronium hexafluorophosphate (0.03 mmol) and diisopropylethylamine in N,N-dimethylformamide (0.15 mL). The resulting mixtures were stirred at room temperature for 1 hr and then purified by preparative reverse phase hplc using a gradient of acetonitrile in 0.1% aqueous formic acid (10% to 100%) to give the title compound as amorphous solids.

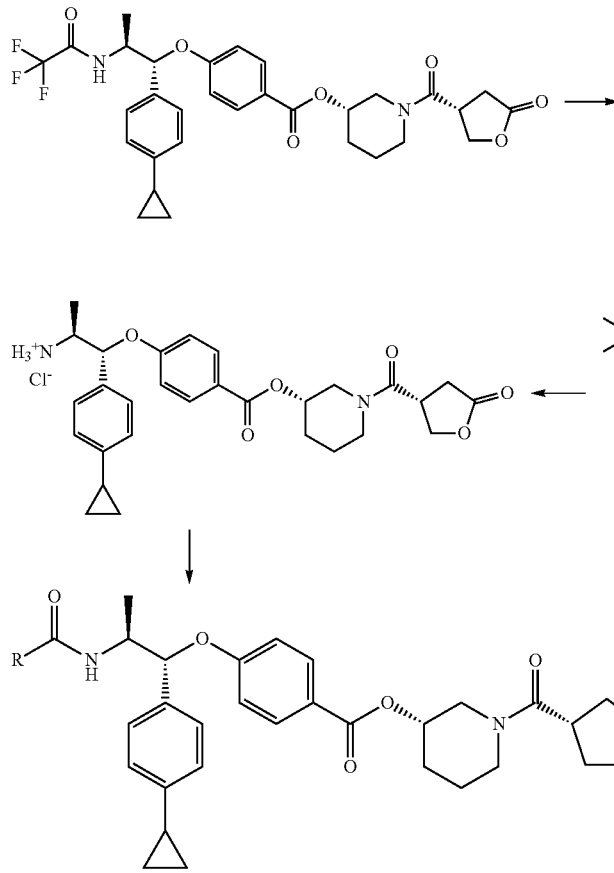

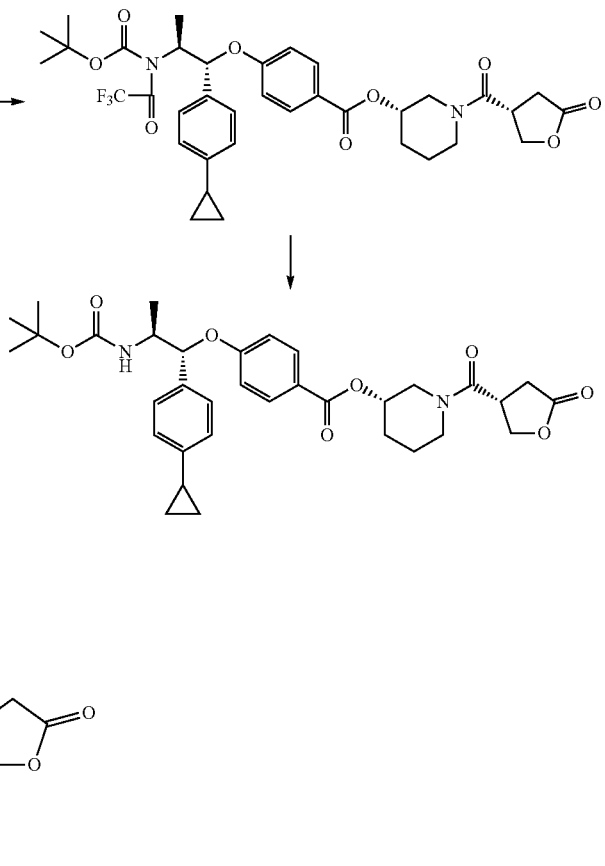

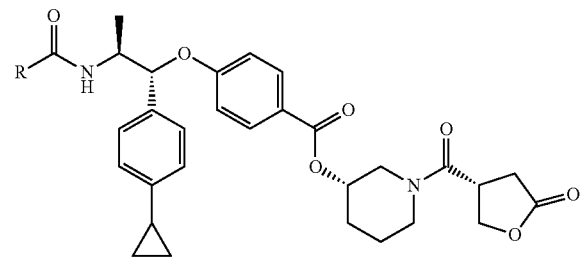

Examples 25-58

The compounds of the following tabulated examples (Table 2) of the general formula:

were prepared as a parallel array using the method outlined below.

Di-tert-butyl dicarbonate (0.426 g, 1.96 mmol) was added to a solution of the compound from Example 24 (0.59 g, 0.98 mmol) and N,N-dimethylpyridine (12 mg, 0.098 mmol) in dichloromethane (5 mL). The resulting solution was stirred at room temperature for 18 hr before being diluted with dichloromethane (100 mL) and washed with 10% aqueous citric acid solution (2×20 mL), saturated aqueous sodium hydrogen carbonate (1×25 mL) and then dried over magne-

TABLE 2

| Example (Compound) | R—CO₂H | Name | Mass¹ Ion | $R_t^1$ (min) |
|---|---|---|---|---|
| 25 | 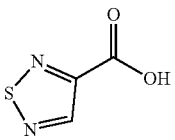 | [(3S)-1-[(3R)-5-oxotetrahydrofuran-3-carbonyl]-3-piperidyl] 4-[(1R,2S)-1-(4-cyclopropylphenyl)-2-(1,2,5-thiadiazole-3-carbonylamino)propoxy]benzoate | 618.21 | 2.50 |
| 26 | 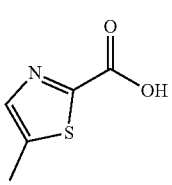 | [(3S)-1-[(3R)-5-oxotetrahydrofuran-3-carbonyl]-3-piperidyl] 4-[(1R,2S)-1-(4-cyclopropylphenyl)-2-[(5-methylthiazole-2-carbonyl)amino]propoxy]benzoate | 631.24 | 2.58 |
| 27 | 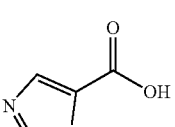 | [(3S)-1-[(3R)-5-oxotetrahydrofuran-3-carbonyl]-3-piperidyl] 4-[(1R,2S)-1-(4-cyclopropylphenyl)-2-(thiazole-5-carbonylamino)propoxy]benzoate | 617.22 | 2.35 |
| 28 | 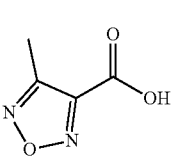 | [(3S)-1-[(3R)-5-oxotetrahydrofuran-3-carbonyl]-3-piperidyl] 4-[(1R,2S)-1-(4-cyclopropylphenyl)-2-[(4-methyl-1,2,5-oxadiazole-3-carbonyl)amino]propoxy]benzoate | 616.25 | 2.55 |
| 29 | 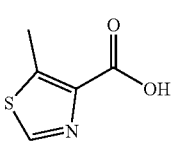 | [(3S)-1-[(3R)-5-oxotetrahydrofuran-3-carbonyl]-3-piperidyl] 4-[(1R,2S)-1-(4-cyclopropylphenyl)-2-[(5-methylthiazole-4-carbonyl)amino]propoxy]benzoate | 631.24 | 2.58 |
| 30 | 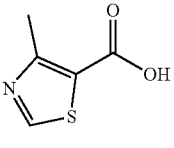 | [(3S)-1-[(3R)-5-oxotetrahydrofuran-3-carbonyl]-3-piperidyl] 4-[(1R,2S)-1-(4-cyclopropylphenyl)-2-[(4-methylthiazole-5-carbonyl)amino]propoxy]benzoate | 631.24 | 2.38 |
| 31[2] | 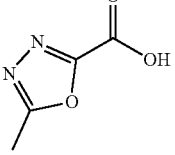 | [(3S)-1-[(3R)-5-oxotetrahydrofuran-3-carbonyl]-3-piperidyl] 4-[(1R,2S)-1-(4-cyclopropylphenyl)-2-[(5-methyl-1,3,4-oxadiazole-2-carbonyl)amino]propoxy]benzoate | 616.25 | 2.35 |
| 32 | 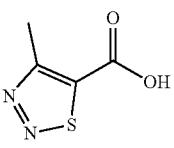 | [(3S)-1-[(3R)-5-oxotetrahydrofuran-3-carbonyl]-3-piperidyl] 4-[(1R,2S)-1-(4-cyclopropylphenyl)-2-[(4-methylthiadiazole-5-carbonyl)amino]propoxy]benzoate | 633.23 | 2.46 |
| 33 | 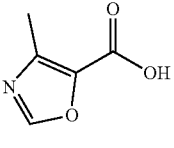 | [(3S)-1-[(3R)-5-oxotetrahydrofuran-3-carbonyl]-3-piperidyl] 4-[(1R/2S)-1-(4-cyclopropylphenyl)-2-[(4-methyloxazole-5-carbonyl)amino]propoxy]benzoate | 615.26 | 2.38 |
| 34[3] | 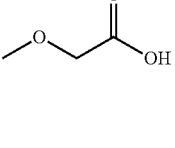 | [(3S)-1-[(3R)-5-oxotetrahydrofuran-3-carbonyl]-3-piperidyl] 4-[(1R,2S)-1-(4-cyclopropylphenyl)-2-[(2-methoxyacetyl)amino]propoxy]benzoate | 578.26 | 2.35 |

TABLE 2-continued

| Example (Compound) | R—CO₂H | Name | Mass¹ Ion | R_t¹ (min) |
|---|---|---|---|---|
| 35 | (1-methylpyrazole-5-carboxylic acid) | [(3S)-1-[(3R)-5-oxotetrahydrofuran-3-carbonyl]-3-piperidyl] 4-[(1R,2S)-1-(4-cyclopropylphenyl)-2-[(2-methylpyrazole-3-carbonyl)amino]propoxy]benzoate | 614.27 | 2.38 |
| 36 | (2-methylthiazole-5-carboxylic acid) | [(3S)-1-[(3R)-5-oxotetrahydrofuran-3-carbonyl]-3-piperidyl] 4-[(1R,2S)-1-(4-cyclopropylphenyl)-2-[(2-methylthiazole-5-carbonyl)amino]propoxy]benzoate | 631.24 | 2.39 |
| 37[4] | ((2R)-tetrahydrofuran-2-carboxylic acid) | [(3S)-1-[(3R)-5-oxotetrahydrofuran-3-carbonyl]-3-piperidyl] 4-[(1R,2S)-1-(4-cyclopropylphenyl)-2-[[(2R)-tetrahydrofuran-2-carbonyl]amino]propoxy]benzoate | 604.28 | 2.37 |
| 38 | (3-methyltriazole-4-carboxylic acid) | [(3S)-1-[(3R)-5-oxotetrahydrofuran-3-carbonyl]-3-piperidyl] 4-[(1R,2S)-1-(4-cyclopropylphenyl)-2-[(3-methyltriazole-4-carbonyl)amino]propoxy]benzoate | 615.27 | 2.34 |
| 39 | (1,2,4-oxadiazole-3-carboxylic acid) | [(3S)-1-[(3R)-5-oxotetrahydrofuran-3-carbonyl]-3-piperidyl] 4-[(1R/2S)-1-(4-cyclopropylphenyl)-2-(1,2,4-oxadiazole-3-carbonylamino)propoxy]benzoate | 602.24 | 2.37 |
| 40 | (1-methylimidazole-2-carboxylic acid) | [(3S)-1-[(3R)-5-oxotetrahydrofuran-3-carbonyl]-3-piperidyl] 4-[(1R,2S)-1-(4-cyclopropylphenyl)-2-[(1-methylimidazole-2-carbonyl)amino]propoxy]benzoate | 614.27 | 2.44 |
| 41 | (3-methylisoxazole-5-carboxylic acid) | [(3S)-1-[(3R)-5-oxotetrahydrofuran-3-carbonyl]-3-piperidyl] 4-[(1R,2S)-1-(4-cyclopropylphenyl)-2-[(3-methylisoxazole-5-carbonyl)amino]propoxy]benzoate | 615.26 | 2.49 |
| 42[5] | (5-methyl-1,2,4-oxadiazole-3-carboxylic acid) | [(3S)-1-[(3R)-5-oxotetrahydrofuran-3-carbonyl]-3-piperidyl] 4-[(1R,2S)-1-(4-cyclopropylphenyl)-2-[(5-methyl-1,2,4-oxadiazole-3-carbonyl)amino]propoxy]benzoate | 616.25 | 2.4 |
| 43 | (1-methylimidazole-4-carboxylic acid) | [(3S)-1-[(3R)-5-oxotetrahydrofuran-3-carbonyl]-3-piperidyl] 4-[(1R,2S)-1-(4-cyclopropylphenyl)-2-[(1-methylimidazole-4-carbonyl)amino]propoxy]benzoate | 614.27 | 2.28 |
| 44 | (isothiazole-3-carboxylic acid) | [(3S)-1-[(3R)-5-oxotetrahydrofuran-3-carbonyl]-3-piperidyl] 4-[(1R,2S)-1-(4-cyclopropylphenyl)-2-(isothiazole-3-carbonylamino)propoxy]benzoate | 617.22 | 2.51 |

TABLE 2-continued

| Example (Compound) | R—CO₂H | Name | Mass¹ Ion | R_t¹ (min) |
|---|---|---|---|---|
| 45 | 3-methylisoxazole-4-carboxylic acid | [(3S)-1-[(3R)-5-oxotetrahydrofuran-3-carbonyl]-3-piperidyl] 4-[(1R,2S)-1-(4-cyclopropylphenyl)-2-[(3-methylisoxazole-4-carbonyl)amino]propoxy]benzoate | 615.26 | 2.42 |
| 46 | thiazole-2-carboxylic acid | [(3S)-1-[(3R)-5-oxotetrahydrofuran-3-carbonyl]-3-piperidyl] 4-[(1R,2S)-1-(4-cyclopropylphenyl)-2-(thiazole-2-carbonylamino)propoxy]benzoate | 617.22 | 2.51 |
| 47 | isothiazole-5-carboxylic acid | [(3S)-1-[(3R)-5-oxotetrahydrofuran-3-carbonyl]-3-piperidyl] 4-[(1R,2S)-1-(4-cyclopropylphenyl)-2-(isothiazole-5-carbonylamino)propoxy]benzoate | 617.22 | 2.44 |
| 48 | 5-methylisothiazole-4-carboxylic acid | [(3S)-1-[(3R)-5-oxotetrahydrofuran-3-carbonyl]-3-piperidyl] 4-[(1R,2S)-1-(4-cyclopropylphenyl)-2-[(5-methylisothiazole-4-carbonyl)amino]propoxy]benzoate | 631.24 | 2.45 |
| 49 | oxazole-2-carboxylic acid | [(3S)-1-[(3R)-5-oxotetrahydrofuran-3-carbonyl]-3-piperidyl] 4-[(1R,2S)-1-(4-cyclopropylphenyl)-2-(oxazole-2-carbonylamino)propoxy]benzoate | 601.24 | 2.38 |
| 50 | oxazole-5-carboxylic acid | [(3S)-1-[(3R)-5-oxotetrahydrofuran-3-carbonyl]-3-piperidyl] 4-[(1R/2S)-1-(4-cyclopropylphenyl)-2-(oxazole-5-carbonylamino)propoxy]benzoate | 601.24 | 2.31 |
| 51 | isoxazole-3-carboxylic acid | [(3S)-1-[(3R)-5-oxotetrahydrofuran-3-carbonyl]-3-piperidyl] 4-[(1R,2S)-1-(4-cyclopropylphenyl)-2-(isoxazole-3-carbonylamino)propoxy]benzoate | 601.24 | 2.44 |
| 52 | thiadiazole-4-carboxylic acid | [(3S)-1-[(3R)-5-oxotetrahydrofuran-3-carbonyl]-3-piperidyl] 4-[(1R,2S)-1-(4-cyclopropylphenyl)-2-(thiadiazole-4-carbonylamino)propoxy]benzoate | 618.21 | 2.45 |
| 53 | 5-methylisoxazole-3-carboxylic acid | [(3S)-1-[(3R)-5-oxotetrahydrofuran-3-carbonyl]-3-piperidyl] 4-[(1R,2S)-1-(4-cyclopropylphenyl)-2-[(5-methylisoxazole-3-carbonyl)amino]propoxy]benzoate | 615.26 | 2.49 |
| 54 | isoxazole-5-carboxylic acid | [(3S)-1-[(3R)-5-oxotetrahydrofuran-3-carbonyl]-3-piperidyl] 4-[(1R,2S)-1-(4-cyclopropylphenyl)-2-(isoxazole-5-carbonylamino)propoxy]benzoate | 601.24 | 2.39 |

TABLE 2-continued

| Example (Compound) | R—CO₂H | Name | Mass¹ Ion | R_t¹ (min) |
|---|---|---|---|---|
| 55 | (thiazole-4-carboxylic acid structure) | [(3S)-1-[(3R)-5-oxotetrahydrofuran-3-carbonyl]-3-piperidyl] 4-[(1R,2S)-1-(4-cyclopropylphenyl)-2-(thiazole-4-carbonylamino)propoxy]benzoate | 617.22 | 2.44 |
| 56 | (3-methyl-1,2,4-oxadiazole-5-carboxylic acid structure) | [(3S)-1-[(3R)-5-oxotetrahydrofuran-3-carbonyl]-3-piperidyl] 4-[(1R,2S)-1-(4-cyclopropylphenyl)-2-[(3-methyl-1,2,4-oxadiazole-5-carbonyl)amino]propoxy]benzoate | 616.25 | 2.45 |
| 57 | (1-methylpyrazole-3-carboxylic acid structure) | [(3S)-1-[(3R)-5-oxotetrahydrofuran-3-carbonyl]-3-piperidyl] 4-[(1R,2S)-1-(4-cyclopropylphenyl)-2-[(1-methylpyrazole-3-carbonyl)amino]propoxy]benzoate | 614.27 | 2.38 |
| 58 | (2,2-difluoropropanoic acid structure) | [(3S)-1-[(3R)-5-oxotetrahydrofuran-3-carbonyl]-3-piperidyl] 4-[(1R,2S)-1-(4-cyclopropylphenyl)-2-(2,2-difluoropropanoylamino)propoxy]benzoate | 598.25 | 2.46 |

¹UPLC-MS method 2 used.
²Compound 31: ¹H NMR (300 MHz, DMSO-d⁶), mixture of rotamers, δ = 9.22 (d, J = 8.7, 1H), 7.77 (dd, J = 8.9, 7.7, 2H), 7.24 (d, J = 8.1, 2H), 7.05-6.84 (m, 4H), 5.53-5.38 (m, 1H), 5.06-4.78 (m, 1H), 4.50-4.30 (m, 2H), 4.20 (ddd, J = 14.7, 8.7, 5.4, 1H), 3.94-3.47 (m, 5H), 2.80-2.52 (m, 5H), 2.02-1.39 (m, 5H), 1.29 (d, J = 6.7, 3H), 0.89 (dd, J = 8.5, 2.4, 2H), 0.69-0.47 (m, 2H).
³Compound 34: ¹H NMR (300 MHz, DMSO-d₆) Mixture of rotamers, δ = 7.82-7.72 (m, 2H), 7.69 (d, J = 8.7, 1H), 7.21 (d, J = 8.1, 2H), 7.08-7.00 (m, 2H), 7.00-6.88 (m, 2H), 5.40 (t, J = 5.0, 1H), 4.99-4.83 (m, 0H), 4.45 (td, J = 8.4, 5.1, 1H), 4.20 (ddd, J = 15.4, 8.8, 5.5, 2H), 3.92-3.41 (m, 7H), 3.18 (s, 3H), 2.78-2.54 (m, 1H), 2.07 (s, 2H), 1.99-1.38 (m, 5H), 1.16 (d, J = 6.8, 3H), 1.01-0.77 (m, 2H), 0.62 (t, J = 5.7, 2H).
⁴Compound 37 can be crystallized from ethyl acetate followed by slurry in heptane at 60° C. for 4 days to give a fully crystalline solid Mpt 146° C.
¹H NMR (300 MHz, DMSO-d₆) Mixture of rotamers δ = 7.84-7.65 (m, 2H), 7.58 (d, J = 9.3, 1H), 7.22 (d, J = 8.1, 2H), 7.08-6.88 (m, 4H), 5.34 (dd, J = 7.1, 3.8, 1H), 5.09-4.83 (m, 1H), 4.45 (td, J = 8.3, 6.2, 1H), 4.20 (ddd, J = 16.0, 8.7, 5.3, 2H), 4.13-4.04 (m, 1H), 3.85 (dt, J = 13.3, 7.0, 1H), 3.79-3.46 (m, 5H), 3.31 (s, 1H), 2.83-2.39 (m, 2H), 2.00-1.43 (m, 7H), 1.34 (q, J = 3.4, 2H), 1.19 (d, J = 6.7, 3H), 0.90 (dq, J = 8.4, 1.3, 2H), 0.61 (td, J = 10.0, 8.8, 5.5, 2H).
⁵Compound 42: ¹H NMR (300 MHz, DMSO-d₆) Mixture of rotamers, δ = 8.88 (d, J = 8.7, 1H), 7.83-7.69 (m, 2H), 7.24 (d, J = 8.2, 2H), 7.11-6.79 (m, 4H), 5.47 (dd, J = 6.2, 4.1, 1H), 5.12-4.75 (m, 1H), 4.53-4.31 (m, 2H), 4.20 (ddd, J = 14.5, 8.8, 5.4, 1H), 3.92-3.51 (m, 4H), 3.49-3.37 (m, 1H), 2.80-2.52 (m, 5H), 2.01-1.40 (m, 2H), 1.27 (d, J = 6.7, 3H), 1.01-0.79 (m, 2H), 0.73-0.51 (m, 2H).

Example 37 Alternative Method: [(3S)-1-[(3R)-5-oxotetrahydrofuran-3-carbonyl]-3-piperidyl] 4-[(1R,2S)-1-(4-cyclopropylphenyl)-2-[[(2R)-tetrahydrofuran-2-carbonyl]amino]propoxy]benzoate (compound 37)

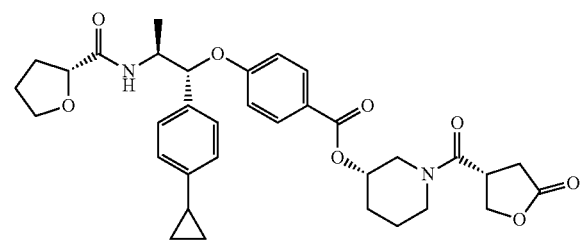 [SMILES: C[C@H](NC(=O)[C@H]1CCCO1)[C@H](Oc1ccc(C(=O)O[C@H]2CCCN(C(=O)[C@H]3COC(=O)C3)C2)cc1)c1ccc(C2CC2)cc1]

Oxalyl chloride (24 mL, 284 mmol) was added to a solution of the lactone from Preparation 33 (7.38 g, 56.7 mmol) in dichloromethane (250 mL) followed by catalytic DMF (0.09 mL). The reaction mixture was stirred at room temperature for 1.5 hr and then evaporated under reduced pressure to give a yellow gum. This gum was dissolved in toluene (2×200 mL) and evaporated under reduced pressure, process repeated to remove the excess oxalyl chloride to give the intermediate (3R)-5-oxotetrahydrofuran-3-carbonyl chloride (8.4 g, 100%).

The intermediate (3R)-5-oxotetrahydrofuran-3-carbonyl chloride (8.4 g, 56.7 mmol) was dissolved in dichloromethane (100 mL) and added to an ice cooled solution of the amine from Preparation 43 (20.0 g, 37.8 mmol) in dichloromethane (400 mL) and 4-methylmorpholine (19.3 mL, 151 mmol). This reaction mixture was stirred at 5° C. for 2.5 hr before being evaporated under reduced pressure. The residue was dissolved in ethyl acetate (300 mL) and washed with 2M aqueous hydrochloric acid (3×100 mL), saturated aqueous sodium hydrogen carbonate (1×50 mL), saturated brine (50 mL) and dried over magnesium sulphate, filtered and the filtrate evaporated under reduced pressure to give a dark brown amorphous solid (25 g). This solid was purified by column chromatography on silica gel (250 g) eluting with 100% ethyl acetate. The resulting cream coloured solid was recrystallized twice from hot ethyl acetate to a white crystalline solid (15.5 g). This solid was suspended in heptane and heated to 90° C. for 5 hrs and then filtered off and dried to constant weight under vacuum at 7 mmHg and 80° C. to give the title compound.

¹H NMR (300 MHz, DMSO-d₆) Mixture of rotamers, δ=7.84-7.65 (m, 2H), 7.58 (d, J=9.3, 1H), 7.22 (d, J=8.1, 2H), 7.08-6.88 (m, 4H), 5.34 (dd, J=7.1, 3.8, 1H), 5.09-4.83

(m, 1H), 4.45 (td, J=8.3, 6.2, 1H), 4.20 (ddd, J=16.0, 8.7, 5.3, 2H), 4.13-4.04 (m, 1H), 3.85 (dt, J=13.3, 7.0, 1H), 3.79-3.46 (m, 5H), 3.31 (s, 1H), 2.83-2.39 (m, 2H), 2.00-1.43 (m, 7H), 1.34 (q, J=3.4, 2H), 1.19 (d, J=6.7, 3H), 0.90 (dq, J=8.4, 1.3, 2H), 0.61 (td, J=10.0, 8.8, 5.5, 2H).

UPLC-MS method 1: Mass ion 604.29 (M$^+$), R$_t$=0.755 min

UPLC-MS method 2: Mass ion 604.29 (M$^+$), R$_t$=2.21 min

Characterization of Polymorph F of Compound 37

DSC

Polymorph F of compound 37 has a differential scanning calorimetry (DSC) curve comprising an endo thermo event with an onset at about 144° C. (±2° C.) and no weight loss associated with the melting process; see FIG. 1.

XRPD

Figure 2:
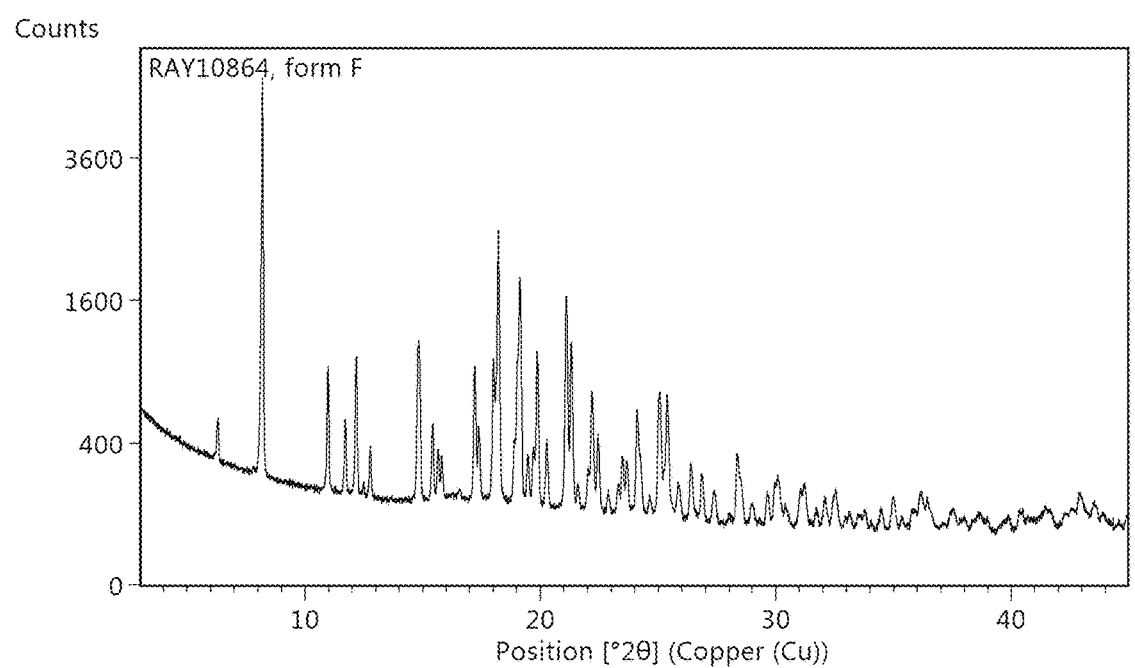
FIG. 2 shows the XRPD (X Ray Powder Diffractogram) pattern of polymorph F of compound 37.

Polymorph F of compound 37 has an XRPD pattern essentially similar as shown in FIG. 2. Polymorph F of compound 37 is characterized by an XRPD pattern exhibiting one or more reflection peaks at approximately 2θ=6.3, 8.2, 14.8, 17.2, 17.4, 21.1 and/or 21.3 (±0.1 degrees) respectively (Bold primary).

Single X-Ray Crystallography

Figure 3:
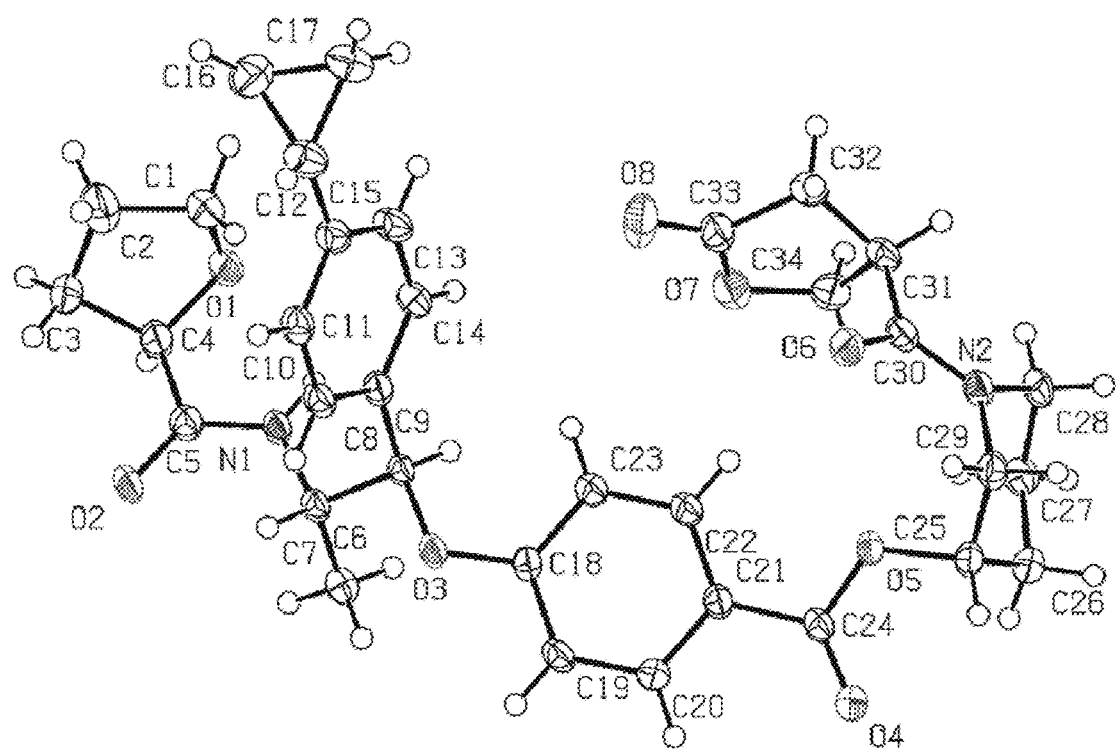
FIG. 3 shows the ORTEP drawing of the absolute crystal structure of polymorph F of compound 37. The structure only has one molecule in the asymmetric unit cell

Polymorph F of compound 37 is characterized by having single crystal parameters which are substantially the same as those provided in Table 3. Polymorph F of compound 37 has a structure obtained by single crystal X-Ray crystallography (XRC) as shown in FIG. 3.

TABLE 3

The crystal parameters from the single crystal structure determination.

| | Form F |
|---|---|
| Chemical formula | C$_{34}$H$_{40}$N$_2$O$_8$ |
| M$_r$ | 604.68 |
| Crystal system, space group | Monoclinic, P2$_1$ |
| Temperature (K) | 120 (2) |
| a, b, c (Å) | 10.9572 (6), 9.6783 (4), 14.6238 (6) |
| β (°) | 102.449 (4) |
| V (Å$^3$) | 1514.34 (12) |
| Z | 2 |
| Radiation type | Cu Kα |
| μ (mm$^{-1}$) | 0.77 |
| Crystal description | Rod |
| Crystal colour | Colourless |
| Crystal size (mm) | 0.55 × 0.15 × 0.11 |
| Diffractometer | SuperNova, Dual, Cu at zero, Atlas diffractometer |
| Absorption correction | Multi-scan CrysAlis PRO, Agilent Technologies, Version 1.171.36.28 (release 01-02-2013 CrysAlis171.NET) (compiled Feb 1 2013, 16:14:44) Empirical absorption correction using spherical harmonics, implemented in SCALE3 ABSPACK scaling algorithm. |
| No. of measured, independent and observed [I > 2σ(I)] reflections | 17432, 5906, 5148 |
| R$_{int}$ | 0.052 |
| (sin θ/λ)$_{max}$ (Å$^{-1}$) | 0.631 |
| R[F$^2$ > 2σ(F$^2$)], wR(F$^2$), S | 0.050, 0.141, 1.11 |
| No. of reflections | 5906 |
| No. of parameters | 398 |
| No. of restraints | 1 |
| H-atom treatment | H-atom parameters constrained |
| Δρ$_{max}$, Δρ$_{min}$ (e Å$^{-3}$) | 0.26, −0.29 |
| Absolute structure | Classical Flack method preferred over Parsons because s.u. lower |
| Absolute structure parameter | 0.1 (3) |

Compound 37 is a single enantiomer, the absolute configuration of the molecule can be determined by analysis of anomalous X-ray scattering by the crystal. The differences in intensities of the anomalous scattering are then compared with calculated scattering intensities for each enantiomer. These measured and calculated intensities can then be fit to a parameter, for instance, the Flack factor (See Flack, H. D.; Bernardinelli, G. Acta Cryst. 1999, A55, 908; Flack, H. D.; Bernardinelli, G. Reporting and evaluating absolute-structure and absolute-configuration determinations, J. Appl. Cryst. 2000, 33, 1143). The Flack factor (absolute structure parameter), x(u) should be close to 0 if the configuration of the solved structure is correct, within statistical fluctuations, usually |x|<2u or x will be close to 1 if the inverse model is correct. The measured Flack factor for the structure of form F of compound 37 is shown in table 3 is 0.1 with a standard uncertainty of 0.3. This structure contains 5 chiral centers located at C4, C6, C8, C25 and C31, which has been assigned as R, S, R, S and R configuration respectively. This is consistent with the proposed configuration of the molecule.

Coordinate for polymorph F of compound 37 data.

| Atom | x | y | z |
|---|---|---|---|
| O | 5.570414 | 9.768308 | −0.773260 |
| O | 6.694541 | 3.522901 | 8.290236 |
| O | 6.498150 | 7.901364 | 3.789618 |
| O | 9.577783 | 2.677018 | 7.166688 |
| O | 5.145490 | 4.864314 | 9.222004 |
| O | 7.993789 | 2.420543 | 4.211591 |
| O | 6.444739 | 6.580276 | −2.167699 |
| N | 8.183500 | 1.201077 | 8.166714 |
| N | 5.932253 | 7.743608 | 0.188496 |
| H | 6.092742 | 6.908371 | 0.057120 |
| O | 9.881556 | 3.393212 | 3.557140 |
| C | 5.798154 | 8.551746 | −0.866794 |
| C | 5.890725 | 4.601064 | 8.308086 |
| C | 6.379705 | 7.042899 | 4.842338 |
| C | 6.065248 | 5.419848 | 7.085721 |
| C | 5.812917 | 8.238169 | 1.557945 |
| H | 6.177416 | 9.146961 | 1.599357 |
| C | 6.647561 | 7.326473 | 2.467579 |
| H | 6.264539 | 6.424456 | 2.460439 |
| C | 8.895762 | 1.648214 | 7.114281 |
| C | 10.793604 | 7.116454 | 1.242357 |
| C | 8.926682 | 8.368826 | 2.144851 |
| H | 8.584313 | 9.168254 | 2.474719 |
| C | 8.101428 | 7.252918 | 2.056316 |
| C | 7.045481 | 5.813755 | 4.913737 |
| H | 7.587371 | 5.532116 | 4.211163 |
| C | 7.183304 | 0.126786 | 8.141010 |
| H | 7.349833 | −0.490690 | 8.870717 |
| H | 7.255329 | −0.364872 | 7.308488 |
| C | 6.755336 | 2.681857 | 9.479044 |
| H | 6.700408 | 3.230617 | 10.288718 |
| C | 6.890834 | 5.020134 | 6.036143 |
| H | 7.343124 | 4.210061 | 6.091835 |
| C | 9.332014 | 2.501841 | 4.145475 |
| C | 10.249978 | 8.303014 | 1.749296 |
| H | 10.786774 | 9.058889 | 1.819268 |
| C | 5.566172 | 7.461001 | 5.891915 |
| H | 5.133589 | 8.282689 | 5.846219 |
| C | 8.840156 | 0.860401 | 5.807664 |
| H | 8.879523 | −0.107429 | 5.961887 |
| C | 7.592738 | 1.263018 | 5.000845 |
| H | 7.310613 | 0.536178 | 4.422506 |
| H | 6.861141 | 1.491426 | 5.594892 |
| C | 5.401994 | 6.651896 | 7.002897 |
| H | 4.848532 | 6.926759 | 7.698331 |
| C | 5.776981 | 0.709419 | 8.272386 |
| H | 5.558760 | 1.199141 | 7.464140 |
| H | 5.138819 | −0.014517 | 8.363778 |
| C | 4.367455 | 8.269140 | 2.000624 |
| H | 3.852019 | 8.780154 | 1.372305 |
| H | 4.307272 | 8.673692 | 2.868846 |
| H | 4.025530 | 7.372929 | 2.040608 |
| C | 9.964731 | 5.999578 | 1.165245 |
| H | 10.303963 | 5.197247 | 0.839662 |

-continued

| Atom | x | y | z |
|---|---|---|---|
| C | 8.644558 | 6.070230 | 1.566513 |
| H | 8.109623 | 5.312419 | 1.507965 |
| C | 5.876332 | 7.889750 | -2.243383 |
| H | 4.976547 | 7.829745 | -2.624658 |
| C | 8.123728 | 2.010183 | 9.380512 |
| H | 8.819856 | 2.685728 | 9.359092 |
| H | 8.269993 | 1.448842 | 10.157342 |
| C | 12.214464 | 7.123229 | 0.816814 |
| H | 12.767776 | 7.810388 | 1.243785 |
| C | 9.941995 | 1.329798 | 4.876610 |
| H | 10.725136 | 1.604662 | 5.379264 |
| H | 10.196054 | 0.628122 | 4.256859 |
| C | 5.651646 | 1.641440 | 9.470476 |
| H | 4.790141 | 2.086641 | 9.441916 |
| H | 5.693756 | 1.121715 | 10.287290 |
| C | 7.864164 | 6.741904 | -2.269087 |
| H | 8.272472 | 5.937637 | -2.624658 |
| H | 8.246487 | 6.922888 | -1.395153 |
| C | 12.950438 | 5.875696 | 0.431255 |
| H | 13.890995 | 5.817626 | 0.662591 |
| H | 12.466999 | 5.035619 | 0.476951 |
| C | 6.782864 | 8.677564 | -3.202997 |
| H | 6.399942 | 8.704663 | -4.094067 |
| H | 6.911520 | 9.585388 | -2.887410 |
| C | 12.559010 | 6.842558 | -0.629747 |
| H | 11.835806 | 6.591890 | -1.225221 |
| H | 13.259801 | 7.373897 | -1.039582 |
| C | 8.096632 | 7.914914 | -3.202997 |
| H | 8.314795 | 7.605208 | -4.096923 |
| H | 8.819784 | 8.474319 | -2.880270 |

Example 59: N-[(3R)-1-[(3R)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide (Compound 59)

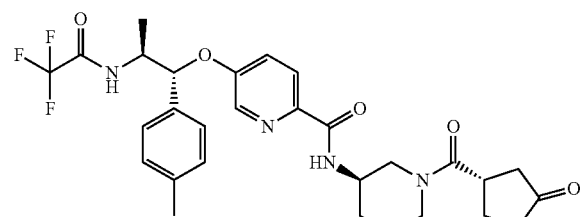

O-(7-Azabenzotriazol-1-yl)-N, N, N',N'-tetramethyluronium hexafluorophosphate (15 mg, 0.038 mmol) was added to a solution of the acid from Preparation 33 (6 mg, 0.039 mmol), the amine from Preparation 17 (9 mg, 0.019 mmol) and triethylamine (20 μL, 0.095 mmol) in N,N-dimethylformamide (0.5 mL). The reaction was shaken for 0.25 hr at room temperature and purified by preparative reverse phase hplc using a gradient of acetonitrile in 50 mM aqueous ammonium bicarbonate solution (5% to 95%) to give the title compound as an amorphous solid.

UPLC-MS method 2: Mass ion 576.22 (M$^+$), R$_t$=2.30 min

Example 60: N-[(3R)-1-[(3S)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide (Compound 60)

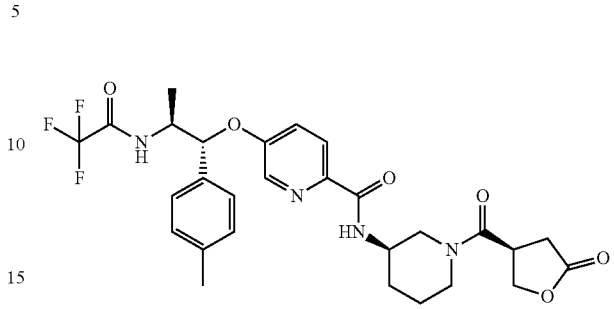

Using a procedure similar to that described for Example 59, but using the acid from Preparation 34, the title compound was prepared as an amorphous solid.

UPLC-MS method 2: Mass ion 576.22 (M$^+$), R$_t$=2.30 min

Example 61: N-[(3R)-1-[(2S)-5-oxotetrahydrofuran-2-carbonyl]-3-piperidyl]-5-[(1R,2S)-1-(p-tolyl)-2-[(2,2,2-trifluoroacetyl)amino]propoxy]pyridine-2-carboxamide (Compound 61)

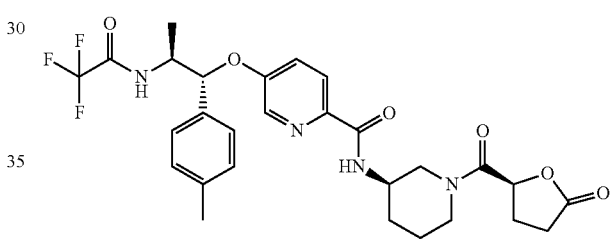

Using a procedure similar to that described for Example 59, but using (2S)-5-oxotetrahydrofuran-2-carboxylic acid instead of the acid from Preparation 33, the title compound was prepared as an amorphous solid.

UPLC-MS method 2: Mass ion 576.22 (M$^+$), R$_t$=2.29 min

Example 62: N-[(3R)-1-[(2R)-5-oxotetrahydrofuran-2-carbonyl]-3-piperidyl]-5-[(1R,2S)-1-(p-tolyl)-2-[(2,2,2-trifluoroacetyl)amino]propoxy]pyridine-2-carboxamide (Compound 62)

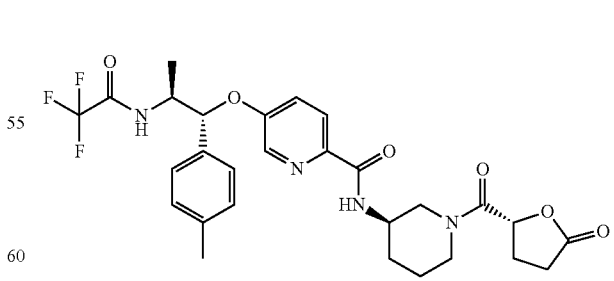

Using a procedure similar to that described for Example 59, but using (2R)-5-oxotetrahydrofuran-2-carboxylic acid instead of the acid from Preparation 33, the title compound was prepared as an amorphous solid.

UPLC-MS method 2: Mass ion 576.22 (M$^+$), R$_t$=2.29 min

Example 63: N-[(3S)-1-[(3S)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide (Compound 63)

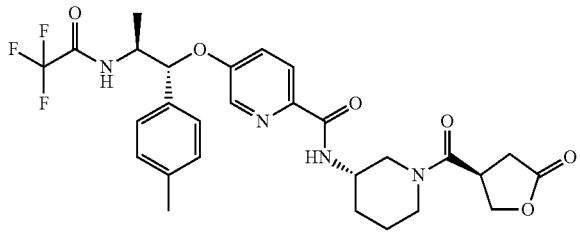 [SMILES: Cc1ccc([C@@H](Oc2ccc(C(=O)N[C@H]3CCCN(C(=O)[C@@H]4COC(=O)C4)C3)nc2)[C@H](C)NC(=O)C(F)(F)F)cc1]

Using a procedure similar to that described for Example 59, but using the acid from Preparation 34 and the amine from Preparation 16, the title compound was prepared as an amorphous solid.

UPLC-MS method 2: Mass ion 576.22 (M+), $R_t$=2.30 min

Example 64: N-[(3S)-1-[(2S)-5-oxotetrahydrofuran-2-carbonyl]-3-piperidyl]-5-[(1R,2S)-1-(p-tolyl)-2-[(2,2,2-trifluoroacetyl)amino]propoxy]pyridine-2-carboxamide (Compound 64)

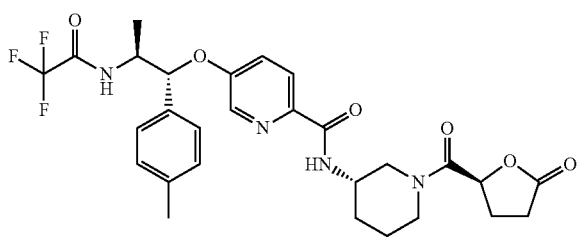 [SMILES: Cc1ccc([C@@H](Oc2ccc(C(=O)N[C@H]3CCCN(C(=O)[C@@H]4CCC(=O)O4)C3)nc2)[C@H](C)NC(=O)C(F)(F)F)cc1]

Using a procedure similar to that described for Example 59, but using (2S)-5-oxotetrahydrofuran-2-carboxylic acid and the amine from Preparation 16, the title compound was prepared as an amorphous solid.

UPLC-MS method 2: Mass ion 576.22 (M+), $R_t$=2.29 min

Example 65: N-[(3R)-1-[(3R)-5-oxotetrahydrofuran-3-carbonyl]pyrrolidin-3-yl]-5-[(1R,2S)-1-(p-tolyl)-2-[(2,2,2-trifluoroacetyl)amino]propoxy]pyridine-2-carboxamide (Compound 65)

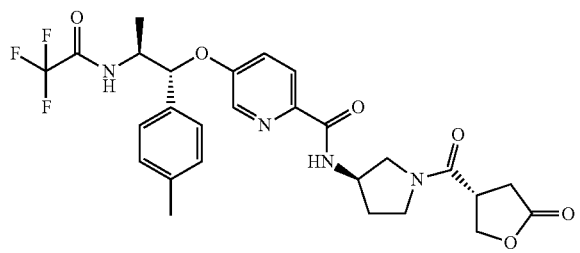 [SMILES: Cc1ccc([C@@H](Oc2ccc(C(=O)N[C@@H]3CCN(C(=O)[C@H]4COC(=O)C4)C3)nc2)[C@H](C)NC(=O)C(F)(F)F)cc1]

Using a procedure similar to that described for Example 2, but using the carbamate from Preparation 32 instead of the one from Preparation 25, via intermediate amine 5-[(1R,2S)-1-(p-tolyl)-2-[(2,2,2-trifluoroacetyl)amino]propoxy]-N-[(3R)-pyrrolidin-3-yl]pyridine-2-carboxamide, the title compound was prepared as an amorphous solid.

UPLC-MS method 2: Mass ion 562.20 (M+), $R_t$=2.21 min

Example 66: 5-[(1R,2S)-1-(4-ethylphenyl)-2-[(2,2,2-trifluoroacetyl)amino]propoxy]-N-[(3S)-1-[(3R)-5-oxotetrahydrofuran-3-carbonyl]-3-piperidyl]pyridine-2-carboxamide (Compound 66)

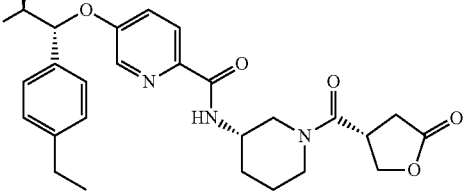

Using a procedure similar to that described for Example 59, but using the amine from Preparation 21 instead of the one from Preparation 17, the title compound was prepared as an amorphous solid.

UPLC-MS method 2: Mass ion 590.24 (M+), $R_t$=2.38 min

Example 67: 5-[(1R,2S)-1-(4-bromophenyl)-2-[(2,2,2-trifluoroacetyl)amino]propoxy]-N-[(3S)-1-[(3R)-5-oxotetrahydrofuran-3-carbonyl]-3-piperidyl]pyridine-2-carboxamide (Compound 67)

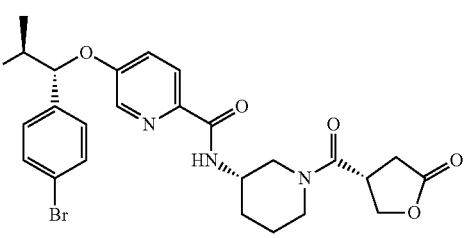

Using a procedure similar to that described for Example 2, but using the carbamate from Preparation 24 instead of the one from Preparation 25 to prepare intermediate amine 5-[(1R,2S)-1-(4-bromophenyl)-2-[(2,2,2-trifluoroacetyl)amino]propoxy]-N-[(3S)-3-piperidyl]pyridine-2-carboxamide, the title compound was prepared as an amorphous solid.

UPLC-MS method 2: Mass ion 640.11 (M+), $R_t$=2.34 min $^1$H NMR (600 MHz, DMSO-$d_6$) mixture of rotamers, b=9.57 (d, J=8.5, 1H), 8.49 (dd, J=25.5, 8.4, 1H), 8.26 (dd, J=10.3, 2.9, 1H), 7.91 (dd, J=14.8, 8.7, 1H), 7.62-7.52 (m, 2H), 7.42 (ddd, J=10.5, 8.8, 2.9, 1H), 7.37-7.29 (m, 2H), 5.46 (dd, J=9.5, 6.2, 1H), 4.61 (t, J=8.5, 0.55H), 4.45 (dd, J=8.8, 8.0, 0.45H), 4.34-4.10 (m, 3H), 3.91-3.67 (m, 3H), 3.08-2.94 (m, 1H), 2.82-2.54 (m, 3H), 1.83 (s, 1H), 1.70 (dddd, J=27.2, 17.8, 13.0, 5.5, 2H), 1.56-1.34 (m, 0H), 1.54-1.34 (m, 1H), 1.30 (dd, J=6.8, 1.6, 3H).

Example 68: N-[(3S)-1-[(3R)-5-oxotetrahydrofuran-3-carbonyl]-3-piperidyl]-5-[(1R,2S)-1-(4-phenylphenyl)-2-[(2,2,2-trifluoroacetyl)amino]propoxy]pyridine-2-carboxamide (Compound 68)

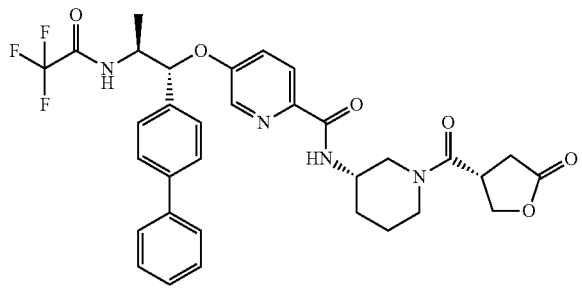 [SMILES: C[C@H](NC(=O)C(F)(F)F)[C@H](Oc1ccc(C(=O)N[C@H]2CCCN(C(=O)[C@H]3COC(=O)C3)C2)nc1)c1ccc(-c2ccccc2)cc1]

[1,1'-Bis(diphenylphosphino)ferrocene]dichloropalladium (II) (1.7 mg, 0.002 mmol) was added to a solution of the bromide from Preparation 24 (24 mg, 0.0413 mmol), phenyl boronic acid (5.5 mg, 0.045 mmol), and aqueous sodium carbonate (2M, 50 µL, 0.1 mmol) in toluene:ethanol 4:1 (250 µL). After flushing the vial with argon it was sealed and reaction heated at 90° C. for 2 hr. The reaction was allowed to cool and diluted with ethyl acetate (50 mL) and washed with 10% aqueous citric acid solution (2×20 mL). The ethyl acetate layer was dried over magnesium sulphate, filtered and evaporated under reduced pressure. The resulting intermediate carbamate was subjected to a procedure similar to that described for Example 2 to give the title compound as an amorphous solid.

UPLC-MS method 2: Mass ion 638.24 (M$^+$), $R_t$=2.43 min

Example 69: N-[(3S)-1-[(3R)-5-oxotetrahydrofuran-3-carbonyl]-3-piperidyl]-4-[(1R,2S)-1-(p-tolyl)-2-[(2,2,2-trifluoroacetyl)amino]propoxy]benzamide (Compound 69)

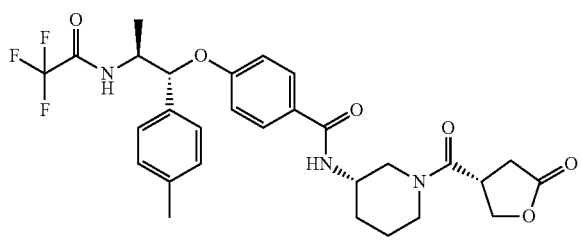 [SMILES: Cc1ccc([C@@H](Oc2ccc(C(=O)N[C@H]3CCCN(C(=O)[C@H]4COC(=O)C4)C3)cc2)[C@H](C)NC(=O)C(F)(F)F)cc1]

Using a procedure similar to that described for Example 2, but using the carbamate from Preparation 38 instead of the one from Preparation 25 to prepare intermediate amine N-[(3S)-3-piperidyl]-4-[(1R,2S)-1-(p-tolyl)-2-[(2,2,2-trifluoroacetyl)amino]propoxy]benzamide, the title compound was prepared as an amorphous solid.

UPLC-MS method 2: Mass ion 575.22 (M$^+$), $R_t$=2.30 min

Example 70: [(3S)-1-[(3R)-5-oxotetrahydrofuran-3-carbonyl]-3-piperidyl] 4-[(1R,2S)-1-(p-tolyl)-2-[(2,2,2-trifluoroacetyl)amino]propoxy]benzoate (Compound 70)

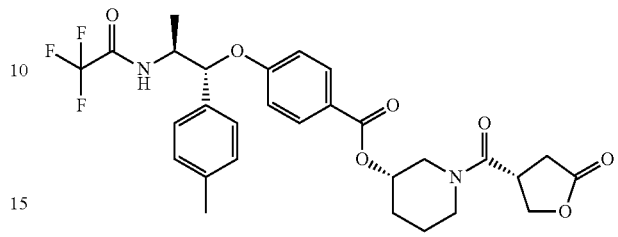

Using a procedure similar to that described for Example 2, but using the carbamate from Preparation 39 instead of the one from Preparation 25 to prepare intermediate amine [(3S)-3-piperidyl] 4-[(1R,2S)-1-(p-tolyl)-2-[(2,2,2-trifluoroacetyl)amino]propoxy]benzoate, the title compound was prepared as an amorphous solid.

UPLC-MS method 2: Mass ion 576.21 (M$^+$), $R_t$=2.45 min

Example 71: N-[(3S)-1-[[(3S)-5-oxotetrahydrofuran-3-yl]carbamoyl]-3-piperidyl]-5-[(1R,2S)-1-(p-tolyl)-2-[(2,2,2-trifluoroacetyl)amino]propoxy]pyridine-2-carboxamide (Compound 71)

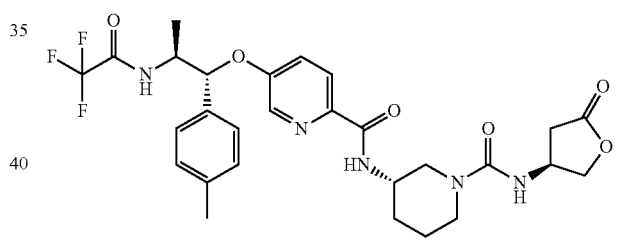

A solution of triethylamine (0.420 mL, 3.0 mmol) and (4S)-4-amino-tetrahydrofuran-2-one (206 mg, 1.5 mmol) in dichloromethane (3 mL) was added drop-wise to a solution of triphosgene (200 mg, 0.675 mmol) in dichloromethane (5 mL) cooled to 0° C. The reaction mixture was stirred at room temperature for 1 hr and then filtered and the filtrate evaporated under reduced pressure. The resulting residue was dissolved in ethyl acetate (10 mL) and stirred for 0.2 hr before filtering. The filtrate was evaporated under reduced pressure to give the crude intermediate isocyanate. This crude (4S)-4-isocyanatotetrahydrofuran-2-one (14 mg, 0.053 mmol) was added to a solution of the amine from Preparation 16 (10 mg, 0.0215 mmol) and triethylamine (7.5 µL, 0.053 mmol) in N,N-dimethylformamide (0.3 mL) and the resulting mixture stirred at room temperature for 0.3 hr. The crude reaction mixture was purified by reverse phase hplc using a gradient of acetonitrile in 50 mM aqueous ammonium bicarbonate solution (5% to 95%) to give the title compound as an amorphous solid (8 mg, 63%).

UPLC-MS method 2: Mass ion 591.23 (M$^+$), $R_t$=2.26 min

Example 72: N-[(3S)-1-[[(3R)-5-oxotetrahydrofuran-3-yl]carbamoyl]-3-piperidyl]-5-[(1R,2S)-1-(p-tolyl)-2-[(2,2,2-trifluoroacetyl)amino]propoxy]pyridine-2-carboxamide (Compound 72)

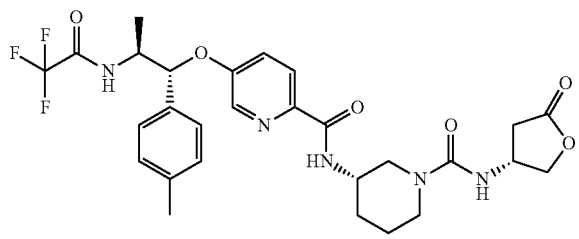 [SMILES: Cc1ccc([C@@H](Oc2ccc(C(=O)N[C@H]3CCCN(C(=O)N[C@H]4COC(=O)C4)C3)nc2)[C@H](C)NC(=O)C(F)(F)F)cc1]

Using a procedure similar to that described for Example 71, but using (4R)-4-amino-tetrahydrofuran-2-one instead of (4S)-4-amino-tetrahydrofuran-2-one, the title compound was prepared as an amorphous solid.

UPLC-MS method 2: Mass ion 591.23 (M$^+$), R$_t$=2.26 min

Example 73: [(3S)-2-oxotetrahydrofuran-3-yl] (3S)-3-[[5-[(1R,2S)-1-(p-tolyl)-2-[(2,2,2-trifluoroacetyl)amino]propoxy]pyridine-2-carbonyl]amino]piperidine-1-carboxylate (Compound 73)

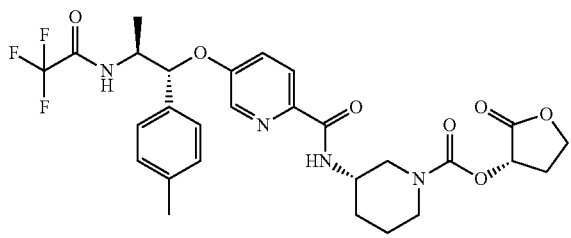 [SMILES: Cc1ccc([C@@H](Oc2ccc(C(=O)N[C@H]3CCCN(C(=O)O[C@H]4CCOC4=O)C3)nc2)[C@H](C)NC(=O)C(F)(F)F)cc1]

A solution of pyridine (0.192 mL, 2.4 mmol) and triphosgene (267 mg, 0.9 mmol) in dichloromethane (5 mL) was added drop-wise to a solution of (3S)-3-hydroxy-tetrahydrofuran-2-one (204 mg, 2 mmol) in dichloromethane (5 mL) cooled to 0° C. The reaction mixture was stirred at room temperature for 2 hr and then evaporated under reduced pressure. The resulting residue was dissolved in ethyl acetate (10 mL) and stirred for 0.2 hr before filtering. The filtrate was evaporated under reduced pressure to give the crude intermediate carbonochloridate. This crude [(3S)-2-oxotetrahydrofuran-3-yl] carbonochloridate (11 mg, 0.064 mmol) was added to a solution of the amine from Preparation 16 (12 mg, 0.026 mmol) and triethylamine (11 □L, 0.078 mmol) in N,N-dimethylformamide (0.5 mL) and the resulting mixture stirred at room temperature for 0.3 hr. The crude reaction mixture was purified by reverse phase hplc using a gradient of acetonitrile in 50 mM aqueous ammonium bicarbonate solution (5% to 95%) to give the title compound as an amorphous solid (10 mg, 52%).

UPLC-MS method 2: Mass ion 592.21 (M$^+$), R$_t$=2.39 min

Example 74: [(3R)-2-oxotetrahydrofuran-3-yl] (3S)-3-[[5-[(1R,2S)-1-(p-tolyl)-2-[(2,2,2-trifluoroacetyl)amino]propoxy]pyridine-2-carbonyl]amino]piperidine-1-carboxylate (Compound 74)

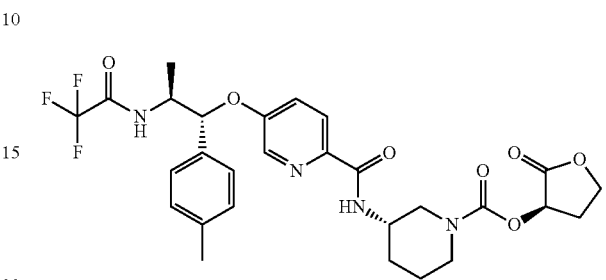

Using a procedure similar to that described for Example 73, but using (3R)-3-hydroxy-tetrahydrofuran-2-one instead of (3S)-3-hydroxy-tetrahydrofuran-2-one, the title compound was prepared as an amorphous solid.

UPLC-MS method 2: Mass ion 592.21 (M$^+$), R$_t$=2.39 min

Example 75: [(3S)-5-oxotetrahydrofuran-3-yl] (3S)-3-[[5-[(1R,2S)-1-(p-tolyl)-2-[(2,2,2-trifluoroacetyl)amino]propoxy]pyridine-2-carbonyl]amino]piperidine-1-carboxylate (Compound 75)

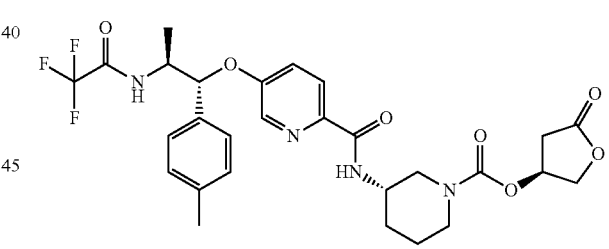

Using a procedure similar to that described for Example 73, but using (4S)-4-hydroxy-tetrahydrofuran-2-one instead of (3S)-3-hydroxy-tetrahydrofuran-2-one, the title compound was prepared as an amorphous solid.

UPLC-MS method 2: Mass ion 592.21 (M$^+$), R$_t$=2.37 min $^1$H NMR (300 MHz, DMSO-d$_6$) 5=9.50 (d, J=8.4, 1H), 8.34 (d, J=8.0, 1H), 8.23 (d, J=2.8, 1H), 7.88 (d, J=8.7, 1H), 7.38 (dd, J=8.8, 2.8, 1H), 7.25 (d, J=7.9, 2H), 7.15 (d, J=7.8, 2H), 5.41 (d, J=6.1, 1H), 5.24 (d, J=6.3, 1H), 4.48 (dd, J=10.7, 4.6, 1H), 4.27 (dd, J=13.5, 8.6, 2H), 3.93-3.61 (m, 3H), 3.14-2.80 (m, 3H), 2.25 (s, 3H), 1.79 (s, 1H), 1.64 (s, 2H), 1.44 (d, J=11.2, 1H), 1.30 (d, J=6.8, 3H).

Example 76: [(3₄)-5-oxotetrahydrofuran-3-yl] (3S)-3-[[5-[(1R,2S)-1-(p-tolyl)-2-[(2,2,2-trifluoroacetyl)amino]propoxy]pyridine-2-carbonyl]amino]piperidine-1-carboxylate (Compound 76)

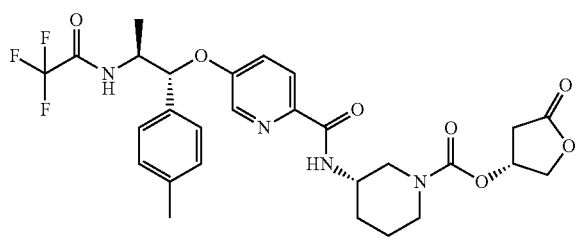 [SMILES: Cc1ccc([C@@H](Oc2ccc(C(=O)N[C@H]3CCCN(C(=O)O[C@H]4COC(=O)C4)C3)nc2)[C@H](C)NC(=O)C(F)(F)F)cc1]

Using a procedure similar to that described for Example 73, but using (4R)-4-hydroxy-tetrahydrofuran-2-one instead of (3S)-3-hydroxy-tetrahydrofuran-2-one, the title compound was prepared as an amorphous solid.

UPLC-MS method 2: Mass ion 592.21 (M$^+$), R$_t$=2.37 min

Example 77: [(3S)-1-[(3S)-5-oxotetrahydrofuran-3-carbonyl]-3-piperidyl] 4-[(1R,2S)-1-(4-cyclopropylphenyl)-2-[[(2R)-tetrahydrofuran-2-carbonyl]amino]propoxy]benzoate (Compound 77)

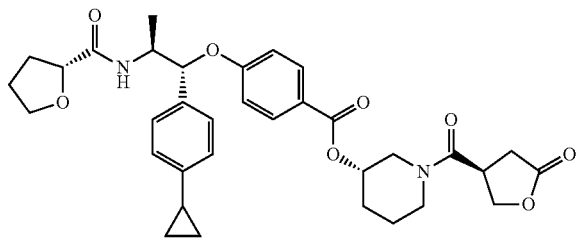 [SMILES: C[C@H](NC(=O)[C@H]1CCCO1)[C@H](Oc1ccc(C(=O)O[C@H]2CCCN(C(=O)[C@@H]3COC(=O)C3)C2)cc1)c1ccc(C2CC2)cc1]

EDAC (253 mg, 1.32 mmol) was added to a solution of the amine from preparation 43 (500 mg, 0.94 mmol), the acid from preparation 34 (147 mg, 1.13 mmol) and Oxyma® (ethyl-2-cyano-2-hydroxyimino-acetate) (53. mg, 0.37 mmol) in ethyl acetate (5 mL). To the resulting mixture triethylamine (0.32 mL, 2.2681 mmol) was added and the mixture stirred at room temperature for 4 hrs.

The reaction mixture was evaporated under reduced pressure. The resulting residue was dissolved in ethyl acetate (20 mL) and washed with 1M aqueous hydrochloric acid (2×10 mL) followed by saturated aqueous sodium hydrogen carbonate (1×10 mL). The ethyl acetate solution was evaporated under reduced pressure to give the title compound as a white amorphous solid (0.54 g, 95%). UPLC-MS method 1: Mass ion 604.29 (MH$^+$), Rt=0.764 min

Example 78: [(3S)-1-[(3R)-5-oxotetrahydrofuran-3-carbonyl]-3-piperidyl] 4-[(1R,2S)-1-(4-cyclopropylphenyl)-2-[[(2S)-tetra hydrofuran-2-carbonyl]amino]propoxy]benzoate (Compound 78)

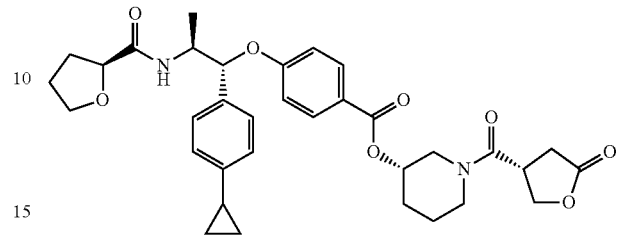

Using a procedure similar to that described for Example 77, but using the amine from Preparation 44 and the acid from Preparation 33, the title compound was prepared as an amorphous solid.

UPLC-MS method 2: Mass ion 604.29 (MH$^+$), R$_t$=0.775 min

Example 79: [(3S)-1-[(3R)-5-oxotetrahydrofuran-3-carbonyl]-3-piperidyl] 4-[(1R,2S)-1-(4-cyclopropylphenyl)-2-[[(2R)-tetrahydrofuran-2-carbonyl]amino]propoxy]benzoate (Compound 79)

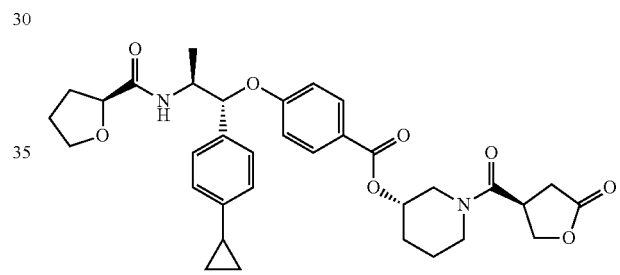

Using a procedure similar to that described for Example 77, but using the amine from Preparation 44, the title compound was prepared as an amorphous solid.

UPLC-MS method 2: Mass ion 604.29 (MH$^+$), R$_t$=0.774 min

Example 80: N-[(3S)-1-[(3S)-5-oxotetrahydrofuran-3-carbonyl]-3-piperidyl]-5-[(1S,2S)-1-(p-tolyl)-2-[(2,2,2-trifluoroacetyl)amino]propoxy]pyridine-2-carboxamide (Compound 80)

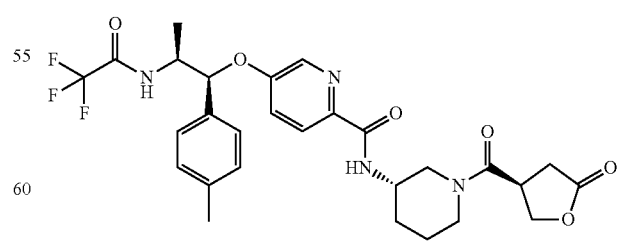

Using a procedure similar to that described for Example 77, but using the amine from Preparation 53, the title compound was prepared as an amorphous solid (35 mg, 29%).

$^1$H NMR (DMSO, 400 MHz): δ=9.11 (br s, 1H), 8.20 (d, J=2.9 Hz, 1H), 8.10 (d, J=7.8 Hz, 1H), 7.89 (d, J=8.8 Hz, 1H), 7.37 (d, J=8.6 Hz, 1H), 7.25 (d, J=8.3 Hz, 2H), 7.14 (d, J=7.8 Hz, 2H), 5.41 (d, J=6.4 Hz, 1H), 4.38-4.42 (m, 1H), 4.20-4.30 (m, 2H), 3.80-3.92 (m, 2H), 3.70-3.80 (m, 2H), 3.02-3.19 (m, 2H), 2.50-2.60 (m, 2H), 2.26 (s, 3H), 1.80-1.90 (m, 2H), 1.60-1.70 (m, 2H), 1.31 (d, J=6.8 Hz, 3H) LCMS (ESI): m/z 565 [M+H]$^+$; 99.6%; RT=2.7 min (KINETEX-1.7u XB-C18 column, 0.05% FA in water with ACN) and Chiral HPLC~96.9% SFC METHOD: Injection volume: 10, Solvent: 0.5% DEA in Methanol, column: Chiralpak LuxCellulose-2(4.6*250) mm, 5u, column Temperature: 30, Flow: 4, Pressure: 100, RT: 2.9 min.

Example 81: N-[(3S)-1-[(3R)-5-oxotetrahydrofuran-3-carbonyl]-3-piperidyl]-5-[(1S,2S)-1-(p-tolyl)-2-[(2,2,2-trifluoroacetyl)amino]propoxy]pyridine-2-carboxamide (Compound 81)

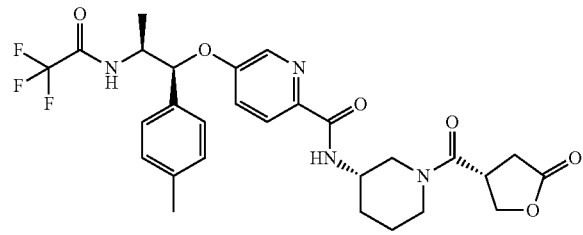 [SMILES: Cc1ccc([C@H](Oc2ccc(C(=O)N[C@H]3CCCN(C(=O)[C@H]4COC(=O)C4)C3)nc2)[C@H](C)NC(=O)C(F)(F)F)cc1]

Using a procedure similar to that described for Example 77, but using the amine from Preparation 53 and the acid from Preparation 33, the title compound was prepared as an amorphous solid (35 mg, 29%).

$^1$H NMR (DMSO, 400 MHz): δ=9.11 (m, 1H), 8.20 (d, J=2.9 Hz, 1H), 8.10 (d, J=7.8 Hz, 1H), 7.89 (d, J=8.8 Hz, 1H), 7.37 (d, J=8.6 Hz, 1H), 7.25 (d, J=8.3 Hz, 2H), 7.14 (d, J=7.8 Hz, 2H), 5.41 (d, J=6.4 Hz, 1H), 4.50 (s, 1H), 4.20-4.30 (m, 2H), 3.80-3.92 (m, 2H), 3.70-3.80 (m, 2H), 3.02-3.19 (m, 2H), 2.55-2.60 (m, 2H), 2.26 (s, 3H), 1.80-1.90 (m, 2H), 1.60-1.70 (m, 2H), 1.31 (d, J=6.8 Hz, 3H) LCMS (ESI): m/z 565 [M+H]$^+$; 98%; RT=3.11 min (KINETEX-1.7u XB-C18 column, 0.05% FA in water with ACN) and Chiral HPLC~93% SFC METHOD: Injection volume: 10, Solvent: 0.5% DEA in Methanol, column: Chiralpak LuxCellulose-2(4.6*250) mm, 5u, column Temperature: 30, Flow: 4, Pressure: 100, RT: 2.67 min.

Glucocorticoid Receptor Binding Assay

GR binding was measured by the use of a commercial kit (A-15897, Life Technologies) with a fluorescence polarization read-out. 4 nM recombinant, full-length receptor protein was incubated with increasing concentrations of GR ligand, 2.5 nM fluorescently labeled tracer (Fluormone GS1, Kd=0.75 nM+/−0.25 nM) and 100 uM stabilizing peptide for 2h at room temperature. Test compounds were diluted in DMSO over seven orders of magnitude, further diluted in assay buffer and distributed into 384-well plates. The sensitivity limit of this assay was 2-4 nM. Displacement of the tracer by 10 μM dexamethasone was used to define the assay window.

Data were processed by sigmoidal curve fitting.

Absolute (Abs) $IC_{50}$ and Emax were determined from the curve fits.

Glucocorticoid receptor binding assay Abs $IC_{50}$ ranges
* Indicates Abs $IC_{50}$<100 nM
** Indicates 100 nM<Abs $IC_{50}$<300 nM
*** Indicates 300 nM<Abs $IC_{50}$
Results are shown in Table 4.

Inhibition of TNF Alpha Release from Human PBMCs

PBMC were isolated from fresh buffy coats by density centrifugation using lymphoprep (Medinor AB, cat no 1019818) tubes. Isolated PBMCs were washed in assay medium (RPMI1640 with 25 mM HEPES, 1% pen/strep, 200 mM L glutamine and 10% Foetal calf serum). Surplus PBMCs were frozen in medium containing extra 10% foetal calf serum and 5% DMSO. On the assay day, fresh cells or cryopreserved cells after thawing were washed in serum free medium (RPMI1640 with 25 mM HEPES, 1% pen/strep, 200 mM L glutamine and 0.5% human serum albumin) and counted, in order to determine the fraction of living cells (generally >95%).

Test compounds were diluted in DMSO over seven orders of magnitude, further diluted in serum-free medium and distributed into wells of 384 well tissue culture plates. LPS was added to a final concentration of 1 μg/ml to the cells. Immediately thereafter titrated test compounds were added and incubated for 18 hours at 37° C.

The level of TNF-a in the culture supernatant was quantitated by AlphaLISA (Perkin Elmer). 2-(3,5-dichloro-4-pyridinyl)-1-(7-methoxyspiro[1,3-benzodioxole-2,1'-cyclopentan]-4-yl)-ethanone (CAS 185406-34-2) at 100×IC50 was used to define the assay window.

Data were processed by sigmoidal curve fitting. $EC_{50}$ and Emax were determined from the curve fits.

Inhibition of TNF alpha release; $EC_{50}$ ranges
* Indicates $EC_{50}$<100 nM
** Indicates 100 nM<$EC_{50}$<300 nM
*** Indicates 300 nM<$EC_{50}$
Results are shown in Table 4.

Human Liver Microsomes (HLM) Assay

Incubations of test compounds in DMSO, diluted with phosphate buffer, pH 7.4, at 0.5 μM were carried out with human liver microsomes (0.5 mg/mL). The percentage of organic solvent in the incubations was 1%. The human liver microsomal suspension in phosphate buffer was mixed with NADPH (1 mM) and preheated to 37° C. before test compound was added. Aliquots were taken at 0, 5, 10, 20 and 30 minutes, and reactions were terminated by addition of methanol containing analytical internal standard (IS).

The results were expressed as apparent clearance ($Cl_{app}$) (mL/min/kg) and hepatic extraction ratio ($E_h$) (%) calculated from the rate constant (k) (min$^{-1}$) of test compound depletion.

* Indicates extraction ratio ($E_h$)>90%
** Indicates 50%<extraction ratio ($E_h$)<90%
*** Indicates extraction ratio ($E_h$)<50%
Results are shown in Table 4.

Human Whole Blood Stability Assay

Incubations of test compounds in DMSO, diluted with phosphate buffer, pH 7.4, at 0.1 μM were carried out with fresh sodium heparin stabilized human whole blood. The percentage of organic solvent in the incubations was 1%. The incubations were performed at 37° C. with aliquots taken at 0, 15, 30, 60 and 120 minutes, and reactions were terminated by addition of acetonitrile containing analytical internal standard (IS).

Test compound depletion, using a compound specific LC/MS/MS method, was determined.

The results were expressed as half-life (T½) in minutes calculated from the rate constant (k) (min$^{-1}$) of test compound depletion.

Some compounds of the present invention were tested in the Human Whole blood stability assay.

Keratinocyte Stability Assay

Incubations of test compounds in DMSO, diluted with growing medium (keratinocyte EpiLife medium, Cascade Biologics Cat. no. M-EPI-500-CA, without growth supplements or antibiotics), pH ~7.4, at 1 µM were carried out with plated human keratinocytes. The percentage of organic solvent in the incubations was 0.01%. The incubations were performed at 37° C. with aliquots taken at 0, 1, 3 and 6 hours, and reactions were terminated by addition of acetonitrile containing analytical internal standard (IS). The results were expressed as half-life (T½) in minutes calculated from the observed rate constant (k) (min$^{-1}$) of test compound depletion.

Some compounds of the present invention were tested in the Keratinocyte stability assay.

TABLE 4

| Compound | GR binding ABS IC50 (nM) | TNF alpha release EC50 (nM) | HLM assay $E_h$ (%) |
|---|---|---|---|
| Dexamethasone | * | * | |
| 1 | * | * | * |
| 2 | * | * | * |
| 3 | * | * | * |
| 4 | * | * | * |
| 5 | * | * | * |
| 6 | * | * | * |
| 7 | * | * | * |
| 8 | * | * | * |
| 9 | ** | * | * |
| 10 | ** | * | * |
| 11 | *** | * | * |
| 12 | * | * | * |
| 13 | ** | * | * |
| 14 | ** | * | * |
| 15 | *** | * | ** |
| 16 | *** | * | * |
| 17 | ** | * | * |
| 18 | ** | * | * |
| 19 | * | * | * |
| 20 | ** | * | * |
| 21 | * | * | n.a. |
| 22 | * | * | * |
| 23 | * | * | * |
| 24 | * | * | * |
| 25 | * | * | * |
| 26 | * | * | * |
| 27 | * | * | n.a. |
| 28 | * | * | * |
| 29 | * | * | * |
| 30 | * | ** | * |
| 31 | * | * | * |
| 32 | * | * | * |
| 33 | * | ** | * |
| 34 | * | * | * |
| 35 | * | ** | * |
| 36 | * | * | * |
| 37 | * | * | * |
| 38 | * | ** | * |
| 39 | * | * | * |
| 40 | * | * | * |
| 41 | * | * | * |
| 42 | * | * | * |
| 43 | * | * | * |
| 44 | * | * | * |
| 45 | * | * | * |
| 46 | * | * | ** |
| 47 | * | * | * |
| 48 | * | * | * |
| 49 | * | * | * |
| 50 | * | * | * |
| 51 | * | * | * |
| 52 | * | * | * |
| 53 | * | * | * |
| 54 | * | * | * |
| 55 | * | * | * |
| 56 | * | * | * |
| 57 | * | * | * |
| 58 | * | * | * |
| 59 | * | * | ** |
| 60 | * | * | n.a. |
| 61 | * | ** | n.a. |
| 62 | * | * | n.a. |
| 63 | * | * | n.a. |
| 64 | * | * | n.a. |
| 65 | ** | * | n.a. |
| 66 | * | * | * |
| 67 | * | * | n.a. |
| 68 | * | * | n.a. |
| 69 | * | * | n.a. |
| 70 | * | * | n.a. |
| 71 | * | * | n.a. |
| 72 | * | ** | n.a. |
| 73 | * | n.a | n.a. |
| 74 | * | * | n.a. |
| 75 | * | ** | n.a. |
| 76 | * | ** | n.a. |
| 77 | * | * | n.a. |
| 78 | * | * | n.a. |
| 79 | * | * | n.a. |
| 80 | * | * | n.a. |
| 81 | * | * | n.a. |

The following are further embodiments of the invention:

Embodiment 1

A compound according to formula (I)

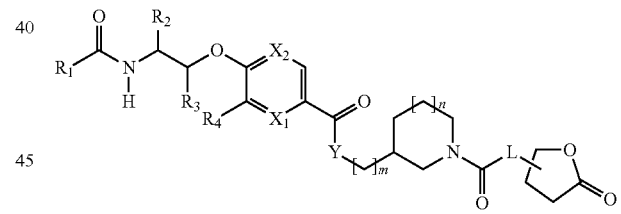

(I)

wherein $R_1$ is selected from the group consisting of 5- and 6-membered heteroaryl, $(C_1-C_6)$alkyl, $(C_3-C_6)$cycloalkyl, (4-6)-membered heterocycloalkyl and phenyl, wherein said 5- and 6-membered heteroaryl, $(C_1-C_6)$alkyl, $(C_3-C_6)$cycloalkyl, (4-6)-membered heterocycloalkyl and phenyl is optionally substituted with one or more substituents independently selected from $(C_1-C_4)$alkyl, $(C_1-C_4)$alkoxy, halogen, hydroxyl and cyano;

$R_2$ is selected from $(C_1-C_3)$alkyl and halo$(C_1-C_3)$alkyl;

$R_3$ is selected from phenyl, 5-membered heteroaryl and 6-membered heteroaryl, wherein said phenyl, 5-membered heteroaryl and 6-membered heteroaryl are optionally substituted with one or more substituents independently selected from $R_5$;

$R_4$ is selected from hydrogen, halogen, $(C_1-C_4)$alkyl and halo$(C_1-C_4)$alkyl;

$R_5$ is selected from halogen, cyano, $(C_1-C_6)$alkyl, $(C_3-C_6)$cycloalkyl, $(C_1-C_6)$alkoxy, halo$(C_1-C_6)$alkyl, halo$(C_1-C_6)$ alkoxy, hydroxy($C_1$-$C_6$)alkyl, phenyl, 5-membered heteroaryl, 6-membered heteroaryl and —$S(O)_2R_a$, wherein $R_a$ represents ($C_1$-$C_4$)alkyl;

$X_1$ is selected from CH, C($R_b$) and N, wherein $R_b$ represents halogen, ($C_1$-$C_4$)alkyl or halo($C_1$-$C_4$)alkyl; $X_2$ is selected from CH and N;

Y is selected from —NH— and —O—;

m is 0 or 1; n is 0 or 1;

L represents a bond, —O—, —NH— or —N($R_c$)—, wherein $R_c$ represents ($C_1$-$C_4$)alkyl;

or pharmaceutically acceptable salts, hydrates or solvates thereof.

Embodiment 2

The compound according to embodiment 1 of general formula (Ia).

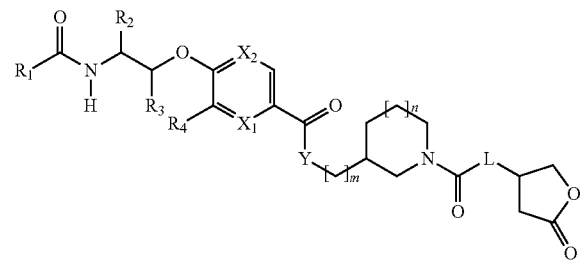

(Ia)

wherein $R_1$, $R_2$, $R_3$, $R_4$, $R_5$, $X_1$, $X_2$, Y, L, m, n and L are as indicated in embodiment 1, or pharmaceutically acceptable salts, hydrates or solvates thereof.

Embodiment 3

The compound according to any one of embodiments 1-2 of general formula (Ib)

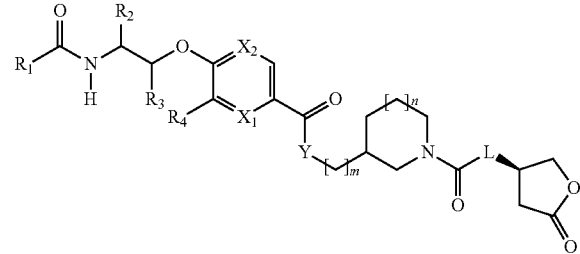

(Ib)

wherein $R_1$, $R_2$, $R_3$, $R_4$, $R_5$, $X_1$, $X_2$, Y, L, m, n and L are as indicated in embodiment 1, or pharmaceutically acceptable salts, hydrates or solvates thereof.

Embodiment 4

The compound according to any one of embodiments 1-3 of general formula (Ic)

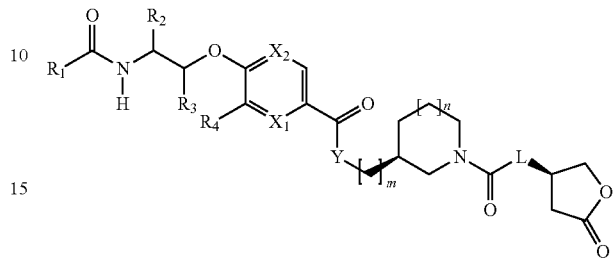

(Ic)

wherein $R_1$, $R_2$, $R_3$, $R_4$, $R_5$, $X_1$, $X_2$, Y, L, m, n and L are as indicated in embodiment 1, or pharmaceutically acceptable salts, hydrates or solvates thereof.

Embodiment 5

The compound according to any one of embodiments 1-3 of general formula (Id).

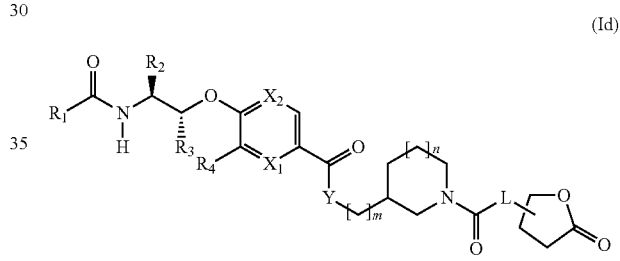

(Id)

wherein $R_1$, $R_2$, $R_3$, $R_4$, $R_5$, $X_1$, $X_2$, Y, L, m, n and L are as indicated in embodiment 1, or pharmaceutically acceptable salts, hydrates or solvates thereof.

Embodiment 6

The compound according to any one of embodiments 1-5 of general formula (Ie).

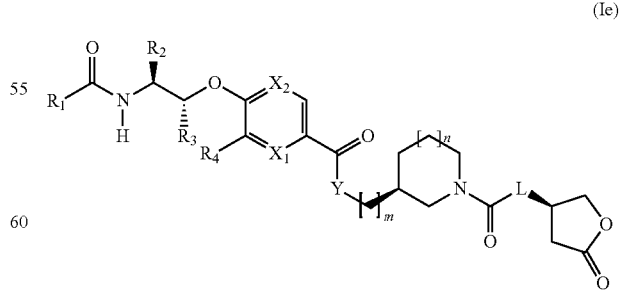

(Ie)

wherein $R_1$, $R_2$, $R_3$, $R_4$, $R_5$, $X_1$, $X_2$, Y, L, m, n and L are as indicated in embodiment 1, or pharmaceutically acceptable salts, hydrates or solvates thereof.

Embodiment 7

The compound according to any one of embodiments 1-6 of general formula (Ih),

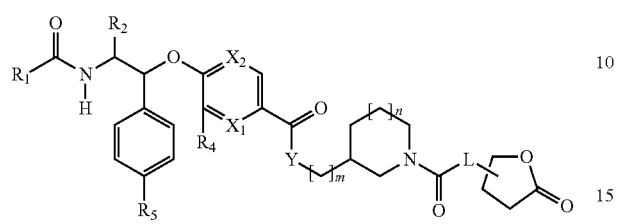

(Ih)

wherein $R_1$, $R_2$, $R_3$, $R_4$, $R_5$, $X_1$, $X_2$, Y, L, m, n and L are as indicated in embodiment 1, or pharmaceutically acceptable salts, hydrates or solvates thereof.

Embodiment 8

The compound according to any one of embodiments 1-7, wherein $R_1$ is selected from the group consisting of 5-membered heteroaryl, $(C_1-C_6)$alkyl, $(C_3-C_6)$cycloalkyl and (4-6)-membered heterocycloalkyl, wherein said 5-membered heteroaryl, $(C_1-C_6)$alkyl, $(C_3-C_6)$cycloalkyl and (4-6)-membered heterocycloalkyl is optionally substituted with one or more substituents independently selected from $(C_1-C_4)$alkyl, $(C_1-C_4)$alkoxy, halogen and hydroxyl.

Embodiment 9

The compound according to any one of embodiments 1-7 wherein $R_1$ is 5-membered heteroaryl optionally substituted with one or more substituents independently selected from $(C_1-C_4)$alkyl, $(C_1-C_4)$alkoxy, halogen, hydroxyl and cyano; $R_2$ is methyl; $R_3$ is phenyl wherein said phenyl is substituted with one or more substituents independently selected from $R_5$; $R_4$ is hydrogen and $X_2$ is CH.

Embodiment 10

The compound according to any one of embodiments 1-7 wherein $R_1$ is $(C_1-C_6)$alkyl, optionally substituted with one or more substituents independently selected from $(C_1-C_4)$alkyl, $(C_1-C_4)$alkoxy, halogen, hydroxyl and cyano; $R_2$ is methyl; $R_3$ is phenyl wherein said phenyl is substituted with one or more substituents independently selected from $R_5$; $R_4$ is hydrogen and $X_2$ is CH.

Embodiment 11

The compound according to any one of embodiments 1-7 wherein $R_1$ is (4-6)-membered heterocycloalkyl optionally substituted with one or more substituents independently selected from $(C_1-C_4)$alkyl, $(C_1-C_4)$alkoxy, halogen, hydroxyl and cyano; $R_2$ is methyl; $R_3$ is phenyl wherein said phenyl is substituted with one or more substituents independently selected from $R_5$; $R_4$ is hydrogen and $X_2$ is CH.

Embodiment 12

The compound according to any one of embodiments 1-7, wherein $R_1$ is selected from the group consisting of imidazolyl, thiadiazolyl, thiazolyl, oxadiazolyl, pyrazolyl, tetrahydrofuranyl, triazolyl, oxazolyl, isoxazolyl, isothiazolyl, methyl, ethyl, propyl, isopropyl, cyclopropyl and cyclobutyl, wherein said imidazolyl, thiadiazolyl, thiazolyl, oxadiazolyl, pyrazolyl, tetrahydrofuranyl, triazolyl, oxazolyl, isoxazolyl, isothiazolyl, methyl, ethyl, propyl, isopropyl, cyclopropyl and cyclobutyl is optionally substituted with one or more substituents independently selected from methyl, methoxy, hydroxyl and fluoro.

Embodiment 13

The compound according to any one of embodiments 1-8, wherein $R_2$ is $(C_1-C_3)$alkyl.

Embodiment 14

The compound according to any one of embodiments 1-13, wherein $R_2$ is methyl.

Embodiment 15

The compound according to any one of embodiments 1-14, wherein $R_3$ is phenyl which is substituted with one or more substituents independently selected from $R_5$.

Embodiment 16

The compound according to any one of embodiments 1-15, wherein $R_3$ is phenyl which is substituted with one or more substituents independently selected from from halogen, $(C_1-C_6)$alkyl, $(C_3-C_6)$cycloalkyl and phenyl.

Embodiment 17

The compound according to any one of embodiments 1-16, wherein $R_5$ is selected from halogen, $(C_1-C_6)$alkyl, $(C_3-C_6)$cycloalkyl and phenyl.

Embodiment 18

The compound according to any one of embodiments 1-17, wherein $R_5$ is selected from bromo, methyl, ethyl, cyclopropyl and phenyl.

Embodiment 19

The compound according to any one of embodiments 1-18, wherein $R_4$ is hydrogen.

Embodiment 20

The compound according to any one of embodiments 1-19, wherein $X_1$ is selected from CH and N.

Embodiment 21

The compound according to any one of embodiments 1-20, wherein $X_1$ is CH.

Embodiment 22

The compound according to any one of embodiments 1-20, wherein $X_1$ is N.

Embodiment 23

The compound according to any one of embodiments 1-22, wherein $X_2$ is CH.

Embodiment 24

The compound according to any one of embodiments 1-23, wherein $X_1$ is N, $X_2$ is CH and Y is —NH—.

Embodiment 25

The compound according to any one of embodiments 1-23, wherein $X_1$ is CH, $X_2$ is CH and Y is —O—.

Embodiment 26

The compound according to any one of embodiments 1-25, wherein m is 0 and n is 1.

Embodiment 27

The compound according to any one of embodiments 1-26, wherein L represents a bond, —O— or —NH—.

Embodiment 28

The compound according to any one of embodiments 1-27, wherein L represents a bond.

Embodiment 29

The compound according to any one of embodiments 1-28 wherein wherein $X_1$ is CH, $X_2$ is CH, Y is —O—, m is 0, n is 1 and L represents a bond.

Embodiment 30

The compound according to any one of embodiments 1-28 wherein wherein $X_1$ is CH, $X_2$ is CH, Y is NH, m is 0, n is 1 and L represents a bond.

Embodiment 31

The compound according to any one of embodiments 1-28 wherein $X_1$ is N, $X_2$ is CH, Y is NH, m is 0, n is 1 and L represents a bond.

Embodiment 32

The compound according to any one of embodiments 1-31 selected from
N-[(3S)-1-[(3R)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide,
5-[(1R,2S)-1-(4-cyclopropylphenyl)-2-[(2,2,2-trifluoroacetyl)amino]propoxy]-N-[(3S)-1-[(3R)-5-oxotetrahydrofuran-3-carbonyl]-3-piperidyl]pyridine-2-carboxamide,
5-[(1R,2S)-1-(4-cyclopropylphenyl)-2-(2,2-difluoropropanoylamino)propoxy]-N-[(3S)-1-[(3R)-5-oxotetrahydrofuran-3-carbonyl]-3-piperidyl]pyridine-2-carboxamide,
N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isothiazole-3-carboxamide,
N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isothiazole-5-carboxamide,
N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]oxazole-2-carboxamide,
N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]thiazole-4-carboxamide,
N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]-3-methylisoxazole-5-carboxamide,
N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]oxazole-5-carboxamide,
5-[(1R,2S)-1-(4-cyclopropylphenyl)-2-[[(2S)-2-hydroxybutanoyl]amino]propoxy]-N-[(3S)-1-[(3R)-5-oxotetrahydrofuran-3-carbonyl]-3-piperidyl]pyridine-2-carboxamide,
5-[(1R,2S)-1-(4-cyclopropylphenyl)-2-[[(2R)-2-hydroxypropanoyl]amino]propoxy]-N-[(3S)-1-[(3R)-5-oxotetrahydrofuran-3-carbonyl]-3-piperidyl]pyridine-2-carboxamide,
N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isoxazole-5-carboxamide,
5-[(1R,2S)-1-(4-cyclopropylphenyl)-2-[[(2R)-2-hydroxybutanoyl]amino]propoxy]-N-[(3S)-1-[(3R)-5-oxotetrahydrofuran-3-carbonyl]-3-piperidyl]pyridine-2-carboxamide,
5-[(1R,2S)-1-(4-cyclopropylphenyl)-2-[(2-methoxyacetyl)amino]propoxy]-N-[(3S)-1-[(3R)-5-oxotetrahydrofuran-3-carbonyl]-3-piperidyl]pyridine-2-carboxamide,
5-[(1R,2S)-1-(4-cyclopropylphenyl)-2-[(2-hydroxy-2-methyl-propanoyl)amino]propoxy]-N-[(3S)-1-[(3R)-5-oxotetrahydrofuran-3-carbonyl]-3-piperidyl]pyridine-2-carboxamide,
5-[(1R,2S)-1-(4-cyclopropylphenyl)-2-(3-hydroxypropanoylamino)propoxy]-N-[(3S)-1-[(3R)-5-oxotetrahydrofuran-3-carbonyl]-3-piperidyl]pyridine-2-carboxamide,
5-[(1R,2S)-1-(4-cyclopropylphenyl)-2-[(1-hydroxycyclobutanecarbonyl)amino]propoxy]-N-[(3S)-1-[(3R)-5-oxotetrahydrofuran-3-carbonyl]-3-piperidyl]pyridine-2-carboxamide,
5-[(1R,2S)-1-(4-cyclopropylphenyl)-2-[(1-hydroxycyclopropanecarbonyl)amino]propoxy]-N-[(3S)-1-[(3R)-5-oxotetrahydrofuran-3-carbonyl]-3-piperidyl]pyridine-2-carboxamide,
N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]oxazole-4-carboxamide,
5-[(1R,2S)-1-(4-cyclopropylphenyl)-2-[[(2S)-tetrahydrofuran-2-carbonyl]amino]propoxy]-N-[(3S)-1-[(3R)-5-oxotetrahydrofuran-3-carbonyl]-3-piperidyl]pyridine-2-carboxamide,
5-[(1R,2S)-1-(4-cyclopropylphenyl)-2-[(2-hydroxyacetyl)amino]propoxy]-N-[(3S)-1-[(3R)-5-oxotetrahydrofuran-3-carbonyl]-3-piperidyl]pyridine-2-carboxamide,
5-[(1R,2S)-1-(4-cyclopropylphenyl)-2-[[(2R)-tetrahydrofuran-2-carbonyl]amino]propoxy]-N-[(3S)-1-[(3R)-5-oxotetrahydrofuran-3-carbonyl]-3-piperidyl]pyridine-2-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isoxazole-3-carboxamide,

[(3S)-1-[(3R)-5-oxotetrahydrofuran-3-carbonyl]-3-piperidyl] 4-[(1R,2S)-1-(4-cyclopropylphenyl)-2-[(2,2,2-trifluoroacetyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-(1,2,5-thiadiazole-3-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-[(5-methylthiazole-2-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-(thiazole-5-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-[(4-methyl-1,2,5-oxadiazole-3-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(5-methylthiazole-4-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(4-methylthiazole-5-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(5-methyl-1,3,4-oxadiazole-2-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(4-methylthiadiazole-5-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(4-methyloxazole-5-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(2-methoxyacetyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(2-methylpyrazole-3-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(2-methylthiazole-5-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[[(2R)-tetrahydrofuran-2-carbonyl]amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(3-methyltriazole-4-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-(1,2,4-oxadiazole-3-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-[(1-methylimidazole-2-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(3-methylisoxazole-5-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(5-methyl-1,2,4-oxadiazole-3-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(1-methylimidazole-4-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-(isothiazole-3-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-[(3-methylisoxazole-4-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-(thiazole-2-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-(isothiazole-5-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-[(5-methylisothiazole-4-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-(oxazole-2-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-(oxazole-5-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-(isoxazole-3-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-(thiadiazole-4-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-[(5-methylisoxazole-3-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-(isoxazole-5-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-(thiazole-4-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-[(3-methyl-1,2,4-oxadiazole-5-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(1-methylpyrazole-3-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-(2,2-difluoropropanoylamino)propoxy]benzoate, N-[(3R)-1-[(3R)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide, N-[(3R)-1-[(3S)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide, N-[(3R)-1-[(2S)-5-oxotetrahydrofuran-2-carbonyl]-3-piperidyl]-5-[(1R,2S)-1-(p-tolyl)-2-[(2,2,2-trifluoroacetyl)amino]propoxy]pyridine-2-carboxamide, N-[(3R)-1-[(2R)-5-oxotetrahydrofuran-2-carbonyl]-3-piperidyl]-5-[(1R,2S)-1-(p-tolyl)-2-[(2,2,2-trifluoroacetyl)amino]propoxy]pyridine-2-carboxamide, N-[(3S)-1-[(3S)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide, N-[(3S)-1-[(2S)-5-oxotetrahydrofuran-2-carbonyl]-3-piperidyl]-5-[(1R,2S)-1-(p-tolyl)-2-[(2,2,2-trifluoroacetyl)amino]propoxy]pyridine-2-carboxamide, N-[(3R)-1-[(3R)-5-oxotetrahydrofuran-3-carbonyl]pyrrolidin-3-yl]-5-[(1R,2S)-1-(p-tolyl)-2-[(2,2,2-trifluoroacetyl)amino]propoxy]pyridine-2-carboxamide, 5-[(1R,2S)-1-(4-ethylphenyl)-2-[(2,2,2-trifluoroacetyl)amino]propoxy]-N-[(3S)-1-[(3R)-5-oxotetrahydrofuran-3-carbonyl]-3-piperidyl]pyridine-2-carboxamide, 5-[(1R,2S)-1-(4-bromophenyl)-2-[(2,2,2-trifluoroacetyl)amino]propoxy]-N-[(3S)-1-[(3R)-5-oxotetrahydrofuran-3-carbonyl]-3-piperidyl]pyridine-2-carboxamide,
N-[(3S)-1-[(3R)-5-oxotetrahydrofuran-3-carbonyl]-3-piperidyl]-5-[(1R,2S)-1-(4-phenylphenyl)-2-[(2,2,2-trifluoroacetyl)amino]propoxy]pyridine-2-carboxamide,
N-[(3S)-1-[(3R)-5-oxotetrahydrofuran-3-carbonyl]-3-piperidyl]-4-[(1R,2S)-1-(p-tolyl)-2-[(2,2,2-trifluoroacetyl)amino]propoxy]benzamide,
[(3S)-1-[(3R)-5-oxotetrahydrofuran-3-carbonyl]-3-piperidyl] 4-[(1R,2S)-1-(p-tolyl)-2-[(2,2,2-trifluoroacetyl)amino]propoxy]benzoate,
N-[(3S)-1-[[(3S)-5-oxotetrahydrofuran-3-yl]carbamoyl]-3-piperidyl]-5-[(1R,2S)-1-(p-tolyl)-2-[(2,2,2-trifluoroacetyl)amino]propoxy]pyridine-2-carboxamide,
N-[(3S)-1-[[(3R)-5-oxotetrahydrofuran-3-yl]carbamoyl]-3-piperidyl]-5-[(1R,2S)-1-(p-tolyl)-2-[(2,2,2-trifluoroacetyl)amino]propoxy]pyridine-2-carboxamide,
[(3S)-2-oxotetrahydrofuran-3-yl] (3S)-3-[[5-[(1R,2S)-1-(p-tolyl)-2-[(2,2,2-trifluoroacetyl)amino]propoxy]pyridine-2-carbonyl]amino]piperidine-1-carboxylate,
[(3R)-2-oxotetrahydrofuran-3-yl] (3S)-3-[[5-[(1R,2S)-1-(p-tolyl)-2-[(2,2,2-trifluoroacetyl)amino]propoxy]pyridine-2-carbonyl]amino]piperidine-1-carboxylate,
[(3S)-5-oxotetrahydrofuran-3-yl] (3S)-3-[[5-[(1R,2S)-1-(p-tolyl)-2-[(2,2,2-trifluoroacetyl)amino]propoxy]pyridine-2-carbonyl]amino]piperidine-1-carboxylate,
[(34)-5-oxotetrahydrofuran-3-yl] (3S)-3-[[5-[(1R,2S)-1-(p-tolyl)-2-[(2,2,2-trifluoroacetyl)amino]propoxy]pyridine-2-carbonyl]amino]piperidine-1-carboxylate,
[(3S)-1-[(3S)-5-oxotetrahydrofuran-3-carbonyl]-3-piperidyl] 4-[(1R,2S)-1-(4-cyclopropylphenyl)-2-[[(2R)-tetrahydrofuran-2-carbonyl]amino]propoxy]benzoate,
[(3S)-1-[(3R)-5-oxotetrahydrofuran-3-carbonyl]-3-piperidyl] 4-[(1R,2S)-1-(4-cyclopropylphenyl)-2-[[(2S)-tetrahydrofuran-2-carbonyl]amino]propoxy]benzoate,
[(3S)-1-[(3R)-5-oxotetrahydrofuran-3-carbonyl]-3-piperidyl] 4-[(1R,2S)-1-(4-cyclopropylphenyl)-2-[[(2R)-tetrahydrofuran-2-carbonyl]amino]propoxy]benzoate,
N-[(3S)-1-[(3S)-5-oxotetrahydrofuran-3-carbonyl]-3-piperidyl]-5-[(1S,2S)-1-(p-tolyl)-2-[(2,2,2-trifluoroacetyl)amino]propoxy]pyridine-2-carboxamide or
N-[(3S)-1-[(3R)-5-oxotetrahydrofuran-3-carbonyl]-3-piperidyl]-5-[(1S,2S)-1-(p-tolyl)-2-[(2,2,2-trifluoroacetyl)amino]propoxy]pyridine-2-carboxamide or pharmaceutically acceptable salts, hydrates or solvates thereof.

Embodiment 33

A compound according to any one of embodiments 1-32 for use in therapy.

Embodiment 34

A compound according to any one of embodiments 1-32 for use in the prophylaxis, treatment or amelioration of inflammatory, allergic or proliferative dermatological diseases or conditions.

Embodiment 35

The compound according to embodiment 34 for use in the prophylaxis, treatment or amelioration of atopic dermatitis, psoriasis or eczema.

Embodiment 36

A pharmaceutical composition comprising a compound according to any one of embodiments 1-32 together with a pharmaceutically acceptable vehicle or excipient or pharmaceutically acceptable carrier(s).

Embodiment 37

The pharmaceutical composition according to embodiment 36 together with one or more other therapeutically active compound(s).

Embodiment 38

The use of a compound according to embodiments 1-32 in the manufacture of a medicament for the prophylaxis, treatment or amelioration of inflammatory, allergic or proliferative dermatological diseases or conditions.

Embodiment 39

A method of preventing, treating or ameliorating inflammatory, allergic or proliferative dermatological diseases or conditions, the method comprising administering to a person suffering from at least one of said diseases or disorders an effective amount of one or more compounds according to according to any one of embodiments 1-32, optionally together with a pharmaceutically acceptable carrier or one or more excipients, optionally in combination with other therapeutically active compounds.

Embodiment 40

A compound according to any one of embodiments 1-32 for use in treatment of a disease, disorder or condition, which disease, disorder or condition is responsive of modulation of the glucocorticoid receptor.

Embodiment 41

A compound according to general formula (VI)

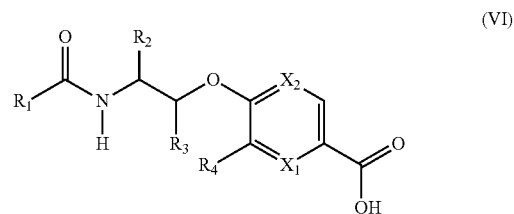

(VI)

wherein
$R_1$ is selected from the group consisting of 5- and 6-membered heteroaryl, $(C_1-C_6)$alkyl, $(C_3-C_6)$cycloalkyl, (4-6)-membered heterocycloalkyl and phenyl, wherein said 5- and 6-membered heteroaryl, $(C_1-C_6)$alkyl, $(C_3-C_6)$cycloalkyl, (4-6)-membered heterocycloalkyl and phenyl is optionally substituted with one or more substituents independently selected from $(C_1-C_4)$alkyl, $(C_1-C_4)$alkoxy, halogen, hydroxyl and cyano;
$R_2$ is selected from $(C_1-C_3)$alkyl and halo$(C_1-C_3)$alkyl;
$R_3$ is selected from phenyl, 5-membered heteroaryl and 6-membered heteroaryl, wherein said phenyl, 5-membered heteroaryl and 6-membered heteroaryl are optionally substituted with one or more substituents independently selected from $R_5$;
$R_4$ is selected from hydrogen, halogen, $(C_1-C_4)$alkyl and halo$(C_1-C_4)$alkyl;

$R_5$ is selected from halogen, cyano, $(C_1-C_6)$alkyl, $(C_3-C_6)$cycloalkyl, $(C_1-C_6)$alkoxy, halo$(C_1-C_6)$alkyl, halo$(C_1-C_6)$alkoxy, hydroxy$(C_1-C_6)$alkyl, phenyl, 5-membered heteroaryl, 6-membered heteroaryl and —S(O)$_2$R$_a$, wherein R$_a$ represents $(C_1-C_4)$alkyl;
$X_1$ is selected from CH, C(R$_b$) and N, wherein R$_b$ represents halogen, $(C_1-C_4)$alkyl or halo$(C_1-C_4)$alkyl;
$X_2$ is selected from CH and N.

Embodiment 42

The compound according to embodiment 41 selected from
5-[(1R,2S)-1-(p-Tolyl)-2-[(2,2,2-trifluoroacetyl)amino]propoxy]pyridine-2-carboxylic acid,
5-[(1R,2S)-1-(4-Ethylphenyl)-2-[(2,2,2-trifluoroacetyl)amino]propoxy]pyridine-2-carboxylic acid,
4-[(1R,2S)-1-(p-tolyl)-2-[(2,2,2-trifluoroacetyl)amino]propoxy]benzoic acid,
5-[(1R,2S)-1-(4-bromophenyl)-2-[(2,2,2-trifluoroacetyl)amino]propoxy]pyridine-2-carboxylic acid,
4-[(1R,2S)-1-(4-bromophenyl)-2-[(2,2,2-trifluoroacetyl)amino]propoxy]benzoic acid,
5-[(1S,2S)-1-(p-tolyl)-2-[(2,2,2-trifluoroacetyl)amino]propoxy]pyridine-2-carboxylic acid.

Embodiment 43

A compound according to general formula (II)

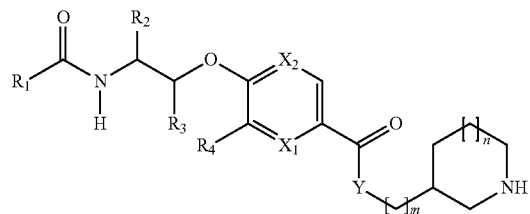

(II)

wherein
$R_1$ is selected from the group consisting of 5- and 6-membered heteroaryl, $(C_1-C_6)$alkyl, $(C_3-C_6)$cycloalkyl, (4-6)-membered heterocycloalkyl and phenyl, wherein said 5- and 6-membered heteroaryl, $(C_1-C_6)$alkyl, $(C_3-C_6)$cycloalkyl, (4-6)-membered heterocycloalkyl and phenyl is optionally substituted with one or more substituents independently selected from $(C_1-C_4)$alkyl, $(C_1-C_4)$alkoxy, halogen, hydroxyl and cyano;
$R_2$ is selected from $(C_1-C_3)$alkyl and halo$(C_1-C_3)$alkyl;
$R_3$ is selected from phenyl, 5-membered heteroaryl and 6-membered heteroaryl, wherein said phenyl, 5-membered heteroaryl and 6-membered heteroaryl are optionally substituted with one or more substituents independently selected from $R_5$;
$R_4$ is selected from hydrogen, halogen, $(C_1-C_4)$alkyl and halo$(C_1-C_4)$alkyl;
$R_5$ is selected from halogen, cyano, $(C_1-C_6)$alkyl, $(C_3-C_6)$cycloalkyl, $(C_1-C_6)$alkoxy, halo$(C_1-C_6)$alkyl, halo$(C_1-C_6)$alkoxy, hydroxy$(C_1-C_6)$alkyl, phenyl, 5-membered heteroaryl, 6-membered heteroaryl and —S(O)$_2$R$_a$, wherein R$_a$ represents $(C_1-C_4)$alkyl;
$X_1$ is selected from CH, C(R$_b$) and N, wherein R$_b$ represents halogen, $(C_1-C_4)$alkyl or halo$(C_1-C_4)$alkyl;
$X_2$ is selected from CH and N;
Y is selected from —NH— and —O—;
m is 0 or 1; n is 0 or 1,
or a pharmaceutically acceptable salt thereof.

Embodiment 44

The compound according to embodiment 43 selected from
N-[(3S)-3-piperidyl]-5-[(1R,2S)-1-(p-tolyl)-2-[(2,2,2-trifluoroacetyl)amino]propoxy]pyridine-2-carboxamide,
N-[(3R)-3-piperidyl]-5-[(1R,2S)-1-(p-tolyl)-2-[(2,2,2-trifluoroacetyl)amino]propoxy]pyridine-2-carboxamide,
5-[(1R,2S)-1-(4-ethylphenyl)-2-[(2,2,2-trifluoroacetyl)amino]propoxy]-N-[(3S)-3-piperidyl]pyridine-2-carboxamide,
5-[(1R,2S)-1-(4-cyclopropylphenyl)-2-[(2,2,2-trifluoroacetyl)amino]propoxy]-N-[(3S)-3-piperidyl]pyridine-2-carboxamide,
5-[(1R,2S)-1-(4-cyclopropylphenyl)-2-[[(2R)-tetrahydrofuran-2-carbonyl]amino]propoxy]-N-[(3S)-3-piperidyl]pyridine-2-carboxamide,
N-[(1S,2R)-2-(4-cyclopropylphenyl)-1-methyl-2-[[6-[[(3S)-3-piperidyl]carbamoyl]-3-pyridyl]oxy]ethyl]isoxazole-3-carboxamide,
5-[(1R,2S)-1-(p-tolyl)-2-[(2,2,2-trifluoroacetyl)amino]propoxy]-N-[(3R)-pyrrolidin-3-yl]pyridine-2-carboxamide,
5-[(1R,2S)-1-(4-bromophenyl)-2-[(2,2,2-trifluoroacetyl)amino]propoxy]-N-[(3S)-3-piperidyl]pyridine-2-carboxamide,
N-[(3S)-3-piperidyl]-4-[(1R,2S)-1-(p-tolyl)-2-[(2,2,2-trifluoroacetyl)amino]propoxy]benzamide,
[(3S)-3-piperidyl] 4-[(1R,2S)-1-(p-tolyl)-2-[(2,2,2-trifluoroacetyl)amino]propoxy]benzoate,
[(3S)-3-piperidyl] 4-[(1R,2S)-1-(4-cyclopropylphenyl)-2-[[(2S)-tetrahydrofuran-2-carbonyl]amino]propoxy]benzoate hydrochloride,
tert-butyl (3S)-3-[[5-[(1S,2S)-1-(p-tolyl)-2-[(2,2,2-trifluoroacetyl)amino]propoxy]pyridine-2-carbonyl]amino]piperidine-1-carboxylate.

Embodiment 45

A compound according to general formula (Va)

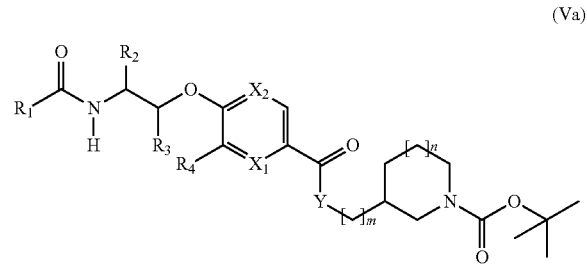

(Va)

wherein
$R_1$ is selected from the group consisting of 5- and 6-membered heteroaryl, $(C_1-C_6)$alkyl, $(C_3-C_6)$cycloalkyl, (4-6)-membered heterocycloalkyl and phenyl, wherein said 5- and 6-membered heteroaryl, $(C_1-C_6)$alkyl, $(C_3-C_6)$cycloalkyl, (4-6)-membered heterocycloalkyl and phenyl is optionally substituted with one or more substituents independently selected from $(C_1-C_4)$alkyl, $(C_1-C_4)$alkoxy, halogen, hydroxyl and cyano;

R$_2$ is selected from (C$_1$-C$_3$)alkyl and halo(C$_1$-C$_3$)alkyl;

R$_3$ is selected from phenyl, 5-membered heteroaryl and 6-membered heteroaryl, wherein said phenyl, 5-membered heteroaryl and 6-membered heteroaryl are optionally substituted with one or more substituents independently selected from R$_5$;

R$_4$ is selected from hydrogen, halogen, (C$_1$-C$_4$)alkyl and halo(C$_1$-C$_4$)alkyl;

R$_5$ is selected from halogen, cyano, (C$_1$-C$_6$)alkyl, (C$_3$-C$_6$)cycloalkyl, (C$_1$-C$_6$)alkoxy, halo(C$_1$-C$_6$)alkyl, halo(C$_1$-C$_6$)alkoxy, hydroxy(C$_1$-C$_6$)alkyl, phenyl, 5-membered heteroaryl, 6-membered heteroaryl and —S(O)$_2$R$_a$, wherein R$_a$ represents (C$_1$-C$_4$)alkyl;

X$_1$ is selected from CH, C(R$_b$) and N, wherein R$_b$ represents halogen, (C$_1$-C$_4$)alkyl or halo(C$_1$-C$_4$)alkyl;

X$_2$ is selected from CH and N;

Y is selected from —NH— and —O—;

m is 0 or 1; n is 0 or 1.

Embodiment 46

The compound according to embodiment 45 selected from

Tert-butyl (3S)-3-[[5-[(1R,2S)-1-(p-tolyl)-2-[(2,2,2-trifluoroacetyl)amino]propoxy]pyridine-2-carbonyl]amino]piperidine-1-carboxylate, tert-butyl (3S)-3-[[5-[(1R,2S)-1-(4-bromophenyl)-2-[(2,2,2-trifluoroacetyl)amino]propoxy]pyridine-2-carbonyl]amino]piperidine-1-carboxylate, tert-butyl (3S)-3-[[5-[(1R,2S)-1-(4-cyclopropylphenyl)-2-[(2,2,2-trifluoroacetyl)amino]propoxy]pyridine-2-carbonyl]amino]piperidine-1-carboxylate, tert-butyl (3S)-3-[[5-[(1R,2S)-1-(4-cyclopropylphenyl)-2-[[(2R)-tetrahydrofuran-2-carbonyl]amino]propoxy]pyridine-2-carbonyl]amino]piperidine-1-carboxylate, tert-butyl (3S)-3-[[5-[(1R,2S)-1-(4-cyclopropylphenyl)-2-(isoxazole-3-carbonylamino)propoxy]pyridine-2-carbonyl]amino]piperidine-1-carboxylate, tert-butyl (3S)-3-[4-[(1R,2S)-1-(4-bromophenyl)-2-[(2,2,2-trifluoroacetyl)amino]propoxy]benzoyl]oxypiperidine-1-carboxylate, tert-butyl (3S)-3-[4-[(1R,2S)-1-(4-cyclopropylphenyl)-2-[(2,2,2-trifluoroacetyl)amino]propoxy]benzoyl]oxypiperidine-1-carboxylate, tert-butyl (3R)-3-[[5-[(1R,2S)-1-(p-tolyl)-2-[(2,2,2-trifluoroacetyl)amino]propoxy]pyridine-2-carbonyl]amino]pyrrolidine-1-carboxylate, tert-butyl (3S)-3-[[4-[(1R,2S)-1-(p-tolyl)-2-[(2,2,2-trifluoroacetyl)amino]propoxy]benzoyl]amino]piperidine-1-carboxylate and tert-butyl (3S)-3-[4-[(1R,2S)-1-(p-tolyl)-2-[(2,2,2-trifluoroacetyl)amino]propoxy]benzoyl]oxypiperidine-1-carboxylate, tert-butyl (3S)-3-[[5-[(1S,2S)-1-(p-tolyl)-2-[(2,2,2-trifluoroacetyl)amino]propoxy]pyridine-2-carbonyl]amino]piperidine-1-carboxylate.

The invention claimed is:

1. A compound according to formula (I)

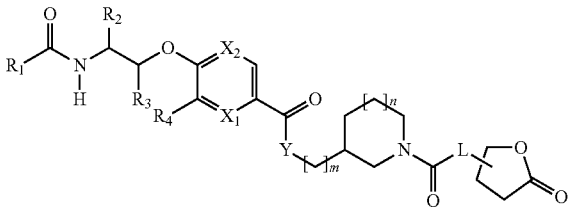

wherein

R$_1$ is a 5- or 6-membered heteroaryl, (C$_1$-C$_6$)alkyl, (C$_3$-C$_6$)cycloalkyl, (4-6)-membered heterocycloalkyl, or phenyl, wherein said 5- and 6-membered heteroaryl, (C$_1$-C$_6$)alkyl, (C$_3$-C$_6$)cycloalkyl, (4-6)-membered heterocycloalkyl, or phenyl is optionally substituted with one or more substituents independently chosen from (C$_1$-C$_4$)alkyl, (C$_1$-C$_4$)alkoxy, halogen, hydroxyl, and cyano;

R$_2$ is (C$_1$-C$_3$)alkyl or halo(C$_1$-C$_3$)alkyl;

R$_3$ is phenyl, a 5-membered heteroaryl, or 6-membered heteroaryl, wherein said phenyl, a 5-membered heteroaryl, or 6-membered heteroaryl are optionally substituted with one or more substituents independently selected from R$_5$;

R$_4$ is a hydrogen, halogen, (C$_1$-C$_4$)alkyl, or halo(C$_1$-C$_4$)alkyl;

R$_5$ is a halogen, cyano, (C$_1$-C$_6$)alkyl, (C$_3$-C$_6$)cycloalkyl, (C$_1$-C$_6$)alkoxy, halo(C$_1$-C$_6$)alkyl, halo(C$_1$-C$_6$)alkoxy, hydroxy(C$_1$-C$_6$)alkyl, phenyl, 5-membered heteroaryl, 6-membered heteroaryl, or —S(O)$_2$R$_a$, wherein R$_a$ represents (C$_1$-C$_4$)alkyl;

X$_1$ is CH, C(R$_b$), or N, wherein R$_b$ represents halogen, (C$_1$-C$_4$)alkyl, or halo(C$_1$-C$_4$)alkyl;

X$_2$ is CH or N;

Y is —NH— or —O—;

m is 0 or 1; n is 0 or 1;

L is a bond, —O—, —NH—, or —N(R$_c$)—, wherein R$_c$ represents (C$_1$-C$_4$)alkyl;

or pharmaceutically acceptable salts, hydrates or solvates thereof.

2. The compound according to claim 1, wherein R$_1$ is a 5-membered heteroaryl, (C$_1$-C$_6$)alkyl, (C$_3$-C$_6$)cycloalkyl, or (4-6)-membered heterocycloalkyl, wherein said 5-membered heteroaryl, (C$_1$-C$_6$)alkyl, (C$_3$-C$_6$)cycloalkyl, or (4-6)-membered heterocycloalkyl is optionally substituted with one or more substituents independently chosen from (C$_1$-C$_4$)alkyl, (C$_1$-C$_4$)alkoxy, halogen, or hydroxyl.

3. The compound according to claim 1, wherein R$_2$ is (C$_1$-C$_3$)alkyl.

4. The compound according to claim 1, wherein R$_3$ is phenyl which is substituted with one or more substituents independently selected from halogen, (C$_1$-C$_6$)alkyl, (C$_3$-C$_6$)cycloalkyl, and phenyl.

5. The compound according to claim 1, wherein R$_4$ is hydrogen.

6. The compound according to claim 1, wherein X$_1$ is CH or N.

7. The compound according to claim 1, wherein X$_2$ is CH.

8. The compound according to claim 1, wherein the compound is:

N-[(3S)-1-[(3R)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide, 5-[(1R,2S)-1-(4-cyclopropylphenyl)-2-[(2,2,2-trifluoroacetyl)amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-(2,2-difluoropropanoylamino)propoxy]-N-[(3S)-1-[(3R)-5-oxotetrahydrofuran-3-carbonyl]-3-piperidyl]pyridine-2-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isothiazole-3-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isothiazole-5-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]oxazole-2-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]thiazole-4-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]-3-methyl-isoxazole-5-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]oxazole-5-carboxamide, 5-[(1R,2S)-1-(4-cyclopropylphenyl)-2-[[(2S)-2-hydroxybutanoyl]amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[[(2R)-2-hydroxypropanoyl]amino]propoxy]-N-[(3S)-1-[(3R)-5-oxotetrahydrofuran-3-carbonyl]-3-piperidyl]pyridine-2-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isoxazole-5-carboxamide, 5-[(1R,2S)-1-(4-cyclopropylphenyl)-2-[[(2R)-2-hydroxybutanoyl]amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[(2-methoxyacetyl)amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[(2-hydroxy-2-methyl-propanoyl)amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-(3-hydroxypropanoylamino)propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[(1-hydroxycyclobutanecarbonyl)amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[(1-hydroxycyclopropanecarbonyl)amino]propoxy]-N-[(3S)-1-[(3R)-5-oxotetrahydrofuran-3-carbonyl]-3-piperidyl]pyridine-2-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]oxazole-4-carboxamide, 5-[(1R,2S)-1-(4-cyclopropylphenyl)-2-[[(2S)-tetrahydrofuran-2-carbonyl]amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[(2-hydroxyacetyl)amino]propoxy]-N-[(3S)-1-[(3R)-5-oxotetrahydrofuran-3-carbonyl]-3-piperidyl]pyridine-2-carboxamide, 5-[(1R,2S)-1-(4-cyclopropylphenyl)-2-[[(2R)-tetrahydrofuran-2-carbonyl]amino]propoxy]-N-[(3S)-1-[(3R)-5-oxotetrahydrofuran-3-carbonyl]-3-piperidyl]pyridine-2-carboxamide, N-[(1S,2R)-2-(4-cyclopropylphenyl)-1-methyl-2-[[6-[[(3S)-1-[(3R)-5-oxotetrahydrofuran-3-carbonyl]-3-piperidyl]carbamoyl]-3-pyridyl]oxy]ethyl]isoxazole-3-carboxamide,

[(3S)-1-[(3R)-5-oxotetrahydrofuran-3-carbonyl]-3-piperidyl] 4-[(1R,2S)-1-(4-cyclopropylphenyl)-2-[(2,2,2-trifluoroacetyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-(1,2,5-thiadiazole-3-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-[(5-methylthiazole-2-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-(thiazole-5-carbonylamino)propoxy]benzoate,

[(3S)-1-[(3R)-5-oxotetrahydrofuran-3-carbonyl]-3-piperidyl] 4-[(1R,2S)-1-(4-cyclopropylphenyl)-2-[(4-methyl-1,2,5-oxadiazole-3-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(5-methylthiazole-4-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(4-methylthiazole-5-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(5-methyl-1,3,4-oxadiazole-2-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(4-methylthiadiazole-5-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(4-methyloxazole-5-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(2-methoxyacetyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(2-methylpyrazole-3-carbonyl)amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[(2-methylthiazole-5-carbonyl)amino]propoxy]benzoate,
[(3S)-1-[(3R)-5-oxotetrahydrofuran-3-carbonyl]-3-piperidyl] 4-[(1R,2S)-1-(4-cyclopropylphenyl)-2-[[(2R)-tetrahydrofuran-2-carbonyl]amino]propoxy]benzoate,
[(3S)-1-[(3R)-5-oxotetrahydrofuran-3-carbonyl]-3-piperidyl] 4-[(1R,2S)-1-(4-cyclopropylphenyl)-2-[(3-methyltriazole-4-carbonyl)amino]propoxy]benzoate,
[(3S)-1-[(3R)-5-oxotetrahydrofuran-3-carbonyl]-3-piperidyl] 4-[(1R,2S)-1-(4-cyclopropylphenyl)-2-(1,2,4-oxadiazole-3-carbonylamino)propoxy]benzoate,
[(3S)-1-[(3R)-5-oxotetrahydrofuran-3-carbonyl]-3-piperidyl] 4-[(1R,2S)-1-(4-cyclopropylphenyl)-2-[(1-methylimidazole-2-carbonyl)amino]propoxy]benzoate,
[(3S)-1-[(3R)-5-oxotetrahydrofuran-3-carbonyl]-3-piperidyl] 4-[(1R,2S)-1-(4-cyclopropylphenyl)-2-[(3-methylisoxazole-5-carbonyl)amino]propoxy]benzoate,
[(3S)-1-[(3R)-5-oxotetrahydrofuran-3-carbonyl]-3-piperidyl] 4-[(1R,2S)-1-(4-cyclopropylphenyl)-2-[(5-methyl-1,2,4-oxadiazole-3-carbonyl)amino]propoxy]benzoate,
[(3S)-1-[(3R)-5-oxotetrahydrofuran-3-carbonyl]-3-piperidyl] 4-[(1R,2S)-1-(4-cyclopropylphenyl)-2-[(1-methylimidazole-4-carbonyl)amino]propoxy]benzoate,
[(3S)-1-[(3R)-5-oxotetrahydrofuran-3-carbonyl]-3-piperidyl] 4-[(1R,2S)-1-(4-cyclopropylphenyl)-2-(isothiazole-3-carbonylamino)propoxy]benzoate,
[(3S)-1-[(3R)-5-oxotetrahydrofuran-3-carbonyl]-3-piperidyl] 4-[(1R,2S)-1-(4-cyclopropylphenyl)-2-[(3-methylisoxazole-4-carbonyl)amino]propoxy]benzoate,
[(3S)-1-[(3R)-5-oxotetrahydrofuran-3-carbonyl]-3-piperidyl] 4-[(1R,2S)-1-(4-cyclopropylphenyl)-2-(thiazole-2-carbonylamino)propoxy]benzoate,
[(3S)-1-[(3R)-5-oxotetrahydrofuran-3-carbonyl]-3-piperidyl] 4-[(1R,2S)-1-(4-cyclopropylphenyl)-2-(isothiazole-5-carbonylamino)propoxy]benzoate,
[(3S)-1-[(3R)-5-oxotetrahydrofuran-3-carbonyl]-3-piperidyl] 4-[(1R,2S)-1-(4-cyclopropylphenyl)-2-[(5-methylisothiazole-4-carbonyl)amino]propoxy]benzoate,
[(3S)-1-[(3R)-5-oxotetrahydrofuran-3-carbonyl]-3-piperidyl] 4-[(1R,2S)-1-(4-cyclopropylphenyl)-2-(oxazole-2-carbonylamino)propoxy]benzoate,
[(3S)-1-[(3R)-5-oxotetrahydrofuran-3-carbonyl]-3-piperidyl] 4-[(1R,2S)-1-(4-cyclopropylphenyl)-2-(oxazole-5-carbonylamino)propoxy]benzoate,
[(3S)-1-[(3R)-5-oxotetrahydrofuran-3-carbonyl]-3-piperidyl] 4-[(1R,2S)-1-(4-cyclopropylphenyl)-2-(isoxazole-3-carbonylamino)propoxy]benzoate,
[(3S)-1-[(3R)-5-oxotetrahydrofuran-3-carbonyl]-3-piperidyl] 4-[(1R,2S)-1-(4-cyclopropylphenyl)-2-(thiadiazole-4-carbonylamino)propoxy]benzoate,
[(3S)-1-[(3R)-5-oxotetrahydrofuran-3-carbonyl]-3-piperidyl] 4-[(1R,2S)-1-(4-cyclopropylphenyl)-2-[(5-methylisoxazole-3-carbonyl)amino]propoxy]benzoate,
[(3S)-1-[(3R)-5-oxotetrahydrofuran-3-carbonyl]-3-piperidyl] 4-[(1R,2S)-1-(4-cyclopropylphenyl)-2-(isoxazole-5-carbonylamino)propoxy]benzoate,
[(3S)-1-[(3R)-5-oxotetrahydrofuran-3-carbonyl]-3-piperidyl] 4-[(1R,2S)-1-(4-cyclopropylphenyl)-2-(thiazole-4-carbonylamino)propoxy]benzoate,
[(3S)-1-[(3R)-5-oxotetrahydrofuran-3-carbonyl]-3-piperidyl] 4-[(1R,2S)-1-(4-cyclopropylphenyl)-2-[(3-methyl-1,2,4-oxadiazole-5-carbonyl)amino]propoxy]benzoate,
[(3S)-1-[(3R)-5-oxotetrahydrofuran-3-carbonyl]-3-piperidyl] 4-[(1R,2S)-1-(4-cyclopropylphenyl)-2-[(1-methylpyrazole-3-carbonyl)amino]propoxy]benzoate,
[(3S)-1-[(3R)-5-oxotetrahydrofuran-3-carbonyl]-3-piperidyl] 4-[(1R,2S)-1-(4-cyclopropylphenyl)-2-(2,2-difluoropropanoylamino)propoxy]benzoate,
N-[(3R)-1-[(3R)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide,
N-[(3R)-1-[(3S)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide,
N-[(3R)-1-[(2S)-5-oxotetrahydrofuran-2-carbonyl]-3-piperidyl]-5-[(1R,2S)-1-(p-tolyl)-2-[(2,2,2-trifluoroacetyl)amino]propoxy]pyridine-2-carboxamide,
N-[(3R)-1-[(2R)-5-oxotetrahydrofuran-2-carbonyl]-3-piperidyl]-5-[(1R,2S)-1-(p-tolyl)-2-[(2,2,2-trifluoroacetyl)amino]propoxy]pyridine-2-carboxamide,
N-[(3S)-1-[(3S)-5-oxotetrahydrofuran-3-carbonyl]-3-piperidyl]-5-[(1R,2S)-1-(p-tolyl)-2-[(2,2,2-trifluoroacetyl)amino]propoxy]pyridine-2-carboxamide,
N-[(3S)-1-[(2S)-5-oxotetrahydrofuran-2-carbonyl]-3-piperidyl]-5-[(1R,2S)-1-(p-tolyl)-2-[(2,2,2-trifluoroacetyl)amino]propoxy]pyridine-2-carboxamide,
N-[(3R)-1-[(3R)-5-oxotetrahydrofuran-3-carbonyl]pyrrolidin-3-yl]-5-[(1R,2S)-1-(p-tolyl)-2-[(2,2,2-trifluoroacetyl)amino]propoxy]pyridine-2-carboxamide,
5-[(1R,2S)-1-(4-ethylphenyl)-2-[(2,2,2-trifluoroacetyl)amino]propoxy]-N-[(3S)-1-[(3R)-5-oxotetrahydrofuran-3-carbonyl]-3-piperidyl]pyridine-2-carboxamide,
5-[(1R,2S)-1-(4-bromophenyl)-2-[(2,2,2-trifluoroacetyl)amino]propoxy]-N-[(3S)-1-[(3R)-5-oxotetrahydrofuran-3-carbonyl]-3-piperidyl]pyridine-2-carboxamide,
N-[(3S)-1-[(3R)-5-oxotetrahydrofuran-3-carbonyl]-3-piperidyl]-5-[(1R,2S)-1-(4-phenylphenyl)-2-[(2,2,2-trifluoroacetyl)amino]propoxy]pyridine-2-carboxamide,
N-[(3S)-1-[(3R)-5-oxotetrahydrofuran-3-carbonyl]-3-piperidyl]-4-[(1R,2S)-1-(p-tolyl)-2-[(2,2,2-trifluoroacetyl)amino]propoxy]benzamide,
[(3S)-1-[(3R)-5-oxotetrahydrofuran-3-carbonyl]-3-piperidyl] 4-[(1R,2S)-1-(p-tolyl)-2-[(2,2,2-trifluoroacetyl)amino]propoxy]benzoate,
N-[(3S)-1-[[(3S)-5-oxotetrahydrofuran-3-yl]carbamoyl]-3-piperidyl]-5-[(1R,2S)-1-(p-tolyl)-2-[(2,2,2-trifluoroacetyl)amino]propoxy]pyridine-2-carboxamide,
N-[(3S)-1-[[(3R)-5-oxotetrahydrofuran-3-yl]carbamoyl]-3-piperidyl]-5-[(1R,2S)-1-(p-tolyl)-2-[(2,2,2-trifluoroacetyl)amino]propoxy]pyridine-2-carboxamide,
[(3S)-2-oxotetrahydrofuran-3-yl] (3S)-3-[[5-[(1R,2S)-1-(p-tolyl)-2-[(2,2,2-trifluoroacetyl)amino]propoxy]pyridine-2-carbonyl]amino]piperidine-1-carboxylate,
[(3R)-2-oxotetrahydrofuran-3-yl] (3S)-3-[[5-[(1R,2S)-1-(p-tolyl)-2-[(2,2,2-trifluoroacetyl)amino]propoxy]pyridine-2-carbonyl]amino]piperidine-1-carboxylate,
[(3S)-5-oxotetrahydrofuran-3-yl] (3S)-3-[[5-[(1R,2S)-1-(p-tolyl)-2-[(2,2,2-trifluoroacetyl)amino]propoxy]pyridine-2-carbonyl]amino]piperidine-1-carboxylate,
[(34)-5-oxotetrahydrofuran-3-yl] (3S)-3-[[5-[(1R,2S)-1-(p-tolyl)-2-[(2,2,2-trifluoroacetyl)amino]propoxy]pyridine-2-carbonyl]amino]piperidine-1-carboxylate,
[(3S)-1-[(3S)-5-oxotetrahydrofuran-3-carbonyl]-3-piperidyl] 4-[(1R,2S)-1-(4-cyclopropylphenyl)-2-[[(2R)-tetrahydrofuran-2-carbonyl]amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[[(2S)-tetrahydrofuran-2-carbonyl]amino]propoxy]benzoate,

[(3S)-1-[(3R)-5-oxotetrahydrofuran-3-carbonyl]-3-piperidyl] 4-[(1R,2S)-1-(4-cyclopropylphenyl)-2-[[(2R)-tetrahydrofuran-2-carbonyl]amino]propoxy]benzoate, N-[(3S)-1-[(3S)-5-oxotetrahydrofuran-3-carbonyl]-3-piperidyl]-5-[(1S,2S)-1-(p-tolyl)-2-[(2,2,2-trifluoroacetyl)amino]propoxy]pyridine-2-carboxamide, or N-[(3S)-1-[(3R)-5-oxotetrahydrofuran-3-carbonyl]-3-piperidyl]-5-[(1S,2S)-1-(p-tolyl)-2-[(2,2,2-trifluoroacetyl)amino]propoxy]pyridine-2-carboxamide or pharmaceutically acceptable salts, hydrates or solvates thereof.

9. A pharmaceutical composition comprising a compound according to claim 1, further comprising at least one pharmaceutically acceptable vehicle or pharmaceutically acceptable excipient or pharmaceutically acceptable carrier.

10. The pharmaceutical composition according to claim 9, further comprising at least one other therapeutically active compound that is capable of preventing, treating or ameliorating atopic dermatitis, psoriasis, or eczema.

11. A method of preventing, treating or ameliorating atopic dermatitis, psoriasis, or eczema, comprising administering to a patient in need thereof a therapeutically effective amount of at least one compound according to claim 1.

12. A method of preventing, treating or ameliorating atopic dermatitis, psoriasis, or eczema, comprising administering to a patient in need thereof a therapeutically effective amount of a pharmaceutical composition according claim 9.

13. A method of preventing, treating or ameliorating atopic dermatitis, psoriasis, or eczema, comprising administering to a patient in need thereof a therapeutically effective amount of a pharmaceutical composition according claim 10.

14. A compound chosen from:

5-[(1R,2S)-1-(p-Tolyl)-2-[(2,2,2-trifluoroacetyl)amino]propoxy]pyridine-2-carboxylic acid, 5-[(1R,2S)-1-(4-Ethylphenyl)-2-[(2,2,2-trifluoroacetyl)amino]propoxy]pyridine-2-carboxylic acid, 4-[(1R,2S)-1-(p-tolyl)-2-[(2,2,2-trifluoroacetyl)amino]propoxy]benzoic acid, 5-[(1R,2S)-1-(4-bromophenyl)-2-[(2,2,2-trifluoroacetyl)amino]propoxy]pyridine-2-carboxylic acid, 4-[(1R,2S)-1-(4-bromophenyl)-2-[(2,2,2-trifluoroacetyl)amino]propoxy]benzoic acid, and 5-[(1S,2S)-1-(p-tolyl)-2-[(2,2,2-trifluoroacetyl)amino]propoxy]pyridine-2-carboxylic acid, N-[(3S)-3-piperidyl]-5-[(1R,2S)-1-(p-tolyl)-2-[(2,2,2-trifluoroacetyl)amino]propoxy]-pyridine-2-carboxamide, N-[(3R)-3-piperidyl]-5-[(1R,2S)-1-(p-tolyl)-2-[(2,2,2-trifluoroacetyl)amino]propoxy]-pyridine-2-carboxamide, 5-[(1R,2S)-1-(4-ethylphenyl)-2-[(2,2,2-trifluoroacetyl)amino]propoxy]-N-[(3S)-3-piperidyl]pyridine-2-carboxamide, 5-[(1R,2S)-1-(4-cyclopropylphenyl)-2-[(2,2,2-trifluoroacetyl)amino]propoxy]-N-[(3S)-3-piperidyl]pyridine-2-carboxamide, 5-[(1R,2S)-1-(4-cyclopropylphenyl)-2-[[(2R)-tetrahydrofuran-2-carbonyl]amino]propoxy]-N-[(3S)-3-piperidyl]pyridine-2-carboxamide, N-[(1S,2R)-2-(4-cyclopropylphenyl)-1-methyl-2-[[6-[[(3S)-3-piperidyl]carbamoyl]-3-pyridyl]oxy]ethyl]isoxazole-3-carboxamide, 5-[(1R,2S)-1-(p-tolyl)-2-[(2,2,2-trifluoroacetyl)amino]propoxy]-N-[(3R)-pyrrolidin-3-yl]pyridine-2-carboxamide, 5-[(1R,2S)-1-(4-bromophenyl)-2-[(2,2,2-trifluoroacetyl)amino]propoxy]-N-[(3S)-3-piperidyl]pyridine-2-carboxamide, N-[(3S)-3-piperidyl]-4-[(1R,2S)-1-(p-tolyl)-2-[(2,2,2-trifluoroacetyl)amino]propoxy]-benzamide,

[(3S)-3-piperidyl] 4-[(1R,2S)-1-(p-tolyl)-2-[(2,2,2-trifluoroacetyl)amino]propoxy]-benzoate,

[(3S)-3-piperidyl] 4-[(1R,2S)-1-(4-cyclopropylphenyl)-2-[[(2S)-tetrahydrofuran-2-carbonyl]amino]propoxy]benzoate hydrochloride, tert-butyl (3S)-3-[[5-[(1S,2S)-1-(p-tolyl)-2-[(2,2,2-trifluoroacetyl)amino]propoxy]-pyridine-2-carbonyl]amino]piperidine-1-carboxylate, tert-butyl (3S)-3-[[5-[(1R,2S)-1-(p-tolyl)-2-[(2,2,2-trifluoroacetyl)amino]propoxy]-pyridine-2-carbonyl]amino]piperidine-1-carboxylate, tert-butyl (3S)-3-[[5-[(1R,2S)-1-(4-bromophenyl)-2-[(2,2,2-trifluoroacetyl)amino]propoxy]pyridine-2-carbonyl]amino]piperidine-1-carboxylate, tert-butyl (3S)-3-[[5-[(1R,2S)-1-(4-cyclopropylphenyl)-2-[(2,2,2-trifluoroacetyl)amino]propoxy]pyridine-2-carbonyl]amino]piperidine-1-carboxylate, tert-butyl (3S)-3-[[5-[(1R,2S)-1-(4-cyclopropylphenyl)-2-[[(2R)-tetrahydrofuran-2-carbonyl]amino]propoxy]pyridine-2-carbonyl]amino]piperidine-1-carboxylate, tert-butyl (3S)-3-[[5-[(1R,2S)-1-(4-cyclopropylphenyl)-2-(isoxazole-3-carbonylamino)propoxy]pyridine-2-carbonyl]amino]piperidine-1-carboxylate, tert-butyl (3S)-3-[4-[(1R,2S)-1-(4-bromophenyl)-2-[(2,2,2-trifluoroacetyl)amino]propoxy]benzoyl]oxypiperidine-1-carboxylate, tert-butyl (3S)-3-[4-[(1R,2S)-1-(4-cyclopropylphenyl)-2-[(2,2,2-trifluoroacetyl)amino]propoxy]benzoyl]oxypiperidine-1-carboxylate, tert-butyl (3R)-3-[[5-[(1R,2S)-1-(p-tolyl)-2-[(2,2,2-trifluoroacetyl)amino]propoxy]pyridine-2-carbonyl]amino]pyrrolidine-1-carboxylate, tert-butyl (3S)-3-[[4-[(1R,2S)-1-(p-tolyl)-2-[(2,2,2-trifluoroacetyl)amino]propoxy]benzoyl]amino]piperidine-1-carboxylate and tert-butyl (3S)-3-[4-[(1R,2S)-1-(p-tolyl)-2-[(2,2,2-trifluoroacetyl)amino]propoxy]benzoyl]oxypiperidine-1-carboxylate, or tert-butyl (3S)-3-[[5-[(1S,2S)-1-(p-tolyl)-2-[(2,2,2-trifluoroacetyl)amino]propoxy]pyridine-2-carbonyl]amino]piperidine-1-carboxylate.

15. The method according to claim 11, wherein the atopic dermatitis, psoriasis, or eczema is chosen from atopic eczema, seborrheal eczema, nummular eczema, xerotic eczema, exfoliative dermatitis, an erythematous disease, a burn, an acid burn, bullous dermatoses, a disease of the lichenoid group, rosacea, erythema exudativum multiform, erythema nodosum, balanitis, pruritus, a manifestation of a vascular disease, vulvitis, alopecia, discoid lupus, cutaneous T-cell lymphoma, a rash, and pityriasis rubra pilaris.

16. The method according to claim 12, wherein the atopic dermatitis, psoriasis, or eczema is chosen from atopic eczema, seborrheal eczema, nummular eczema, xerotic eczema, exfoliative dermatitis, an erythematous disease, a burn, an acid burn, bullous dermatoses, a disease of the lichenoid group, rosacea, erythema exudativum multiform, erythema nodosum, balanitis, pruritus, a manifestation of a vascular disease, vulvitis, alopecia, discoid lupus, cutaneous T-cell lymphoma, a rash, and pityriasis rubra pilaris.

17. The method according to claim 13, wherein the atopic dermatitis, psoriasis, or eczema is chosen from atopic eczema, seborrheal eczema, nummular eczema, xerotic eczema, exfoliative dermatitis, an erythematous disease, a burn, an acid burn, bullous dermatoses, a disease of the lichenoid group, rosacea, erythema exudativum multiform, erythema nodosum, balanitis, pruritus, a manifestation of a vascular disease, vulvitis, alopecia, discoid lupus, cutaneous T-cell lymphoma, a rash, and pityriasis rubra pilaris.

* * * * *

UNITED STATES PATENT AND TRADEMARK OFFICE
CERTIFICATE OF CORRECTION

PATENT NO. : 10,494,363 B2
APPLICATION NO. : 15/759622
DATED : December 3, 2019
INVENTOR(S) : Patrick Stephen Johnson, Kevin Neil Dack and Krister Henriksson Page 1 of 2

It is certified that error appears in the above-identified patent and that said Letters Patent is hereby corrected as shown below:

On the Title Page

ABSTRACT, Line 3 of item (57), in formula (I):

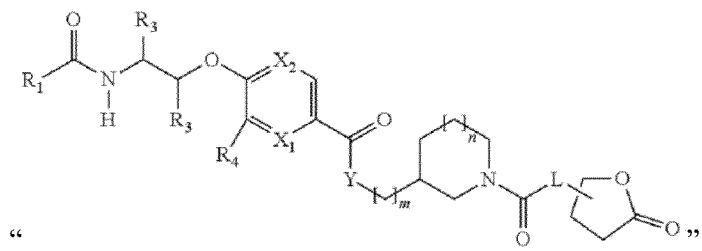

"

Should read:

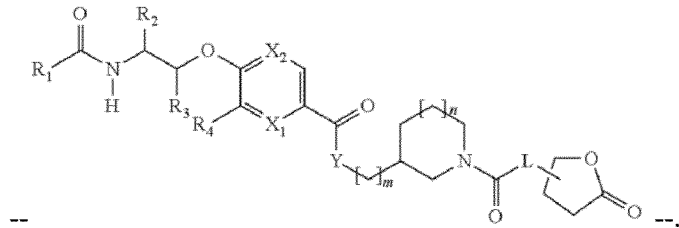

--

Signed and Sealed this
Third Day of March, 2020

Andrei Iancu
*Director of the United States Patent and Trademark Office*

CERTIFICATE OF CORRECTION (continued)
U.S. Pat. No. 10,494,363 B2

In the Specification

Column 2, Lines 43-55, in formula (I):

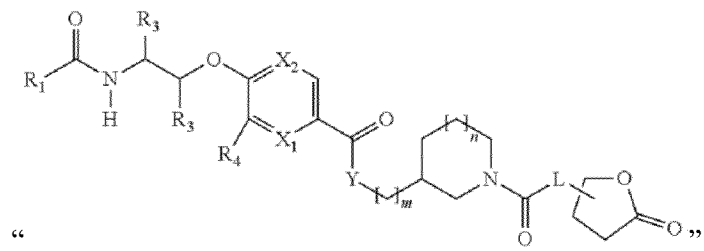

"

Should read:

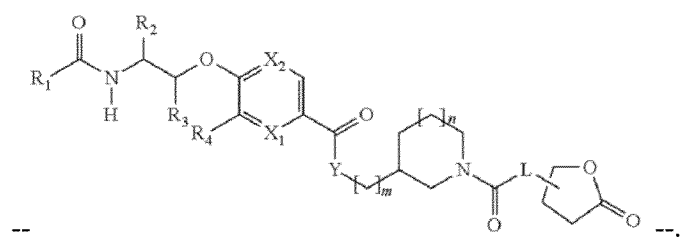

--  --.